US008106215B2

(12) United States Patent
Aissaoui et al.

(10) Patent No.: US 8,106,215 B2
(45) Date of Patent: Jan. 31, 2012

(54) 3-AZA-BICYCLO[3.3.0]OCTANE COMPOUNDS

(75) Inventors: Hamed Aissaoui, Pulversheim (FR); Christoph Boss, Allschwil (CH); Markus Gude, Allschwil (CH); Ralf Koberstein, Lorrach (DE); Thierry Sifferlen, Wentzwiller (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 12/667,193

(22) PCT Filed: Jul. 2, 2008

(86) PCT No.: PCT/IB2008/052656
§ 371 (c)(1),
(2), (4) Date: Dec. 29, 2009

(87) PCT Pub. No.: WO2009/004584
PCT Pub. Date: Jan. 8, 2009

(65) Prior Publication Data
US 2010/0184808 A1    Jul. 22, 2010

(30) Foreign Application Priority Data

Jul. 3, 2007    (WO) ................ PCT/IB2007/052598

(51) Int. Cl.
| C07D 277/20 | (2006.01) |
| C07D 417/04 | (2006.01) |
| C07D 417/14 | (2006.01) |
| C07D 513/14 | (2006.01) |
| C07D 417/00 | (2006.01) |
| C07D 513/02 | (2006.01) |
| A61K 31/44 | (2006.01) |
| A61K 31/415 | (2006.01) |
| A61K 31/425 | (2006.01) |

(52) U.S. Cl. ..... 548/200; 548/154; 548/159; 546/269.7; 546/121; 514/300; 514/399; 514/368; 514/365

(58) Field of Classification Search .................. None
See application file for complete search history.

(56) References Cited

U.S. PATENT DOCUMENTS

| 5,447,952 | A | 9/1995 | Wulfert et al. |
| 2003/0186964 | A1 | 10/2003 | Branch et al. |
| 2004/0058921 | A1 | 3/2004 | Branch et al. |
| 2006/0040937 | A1 | 2/2006 | Branch et al. |
| 2006/0252769 | A1 | 11/2006 | Branch et al. |
| 2010/0069418 | A1 | 3/2010 | Aissaoui et al. |
| 2011/0009461 | A1* | 1/2011 | Aissaoui et al. ............. 514/368 |

FOREIGN PATENT DOCUMENTS

| EP | 58906 | 9/1982 |
| WO | WO 95/29922 | 11/1995 |
| WO | WO 01/96302 | 12/2001 |
| WO | WO 02/44172 | 6/2002 |
| WO | WO 02/090355 | 11/2002 |
| WO | WO 03/041711 | 5/2003 |
| WO | WO 03/062265 | 7/2003 |
| WO | WO 2004/026866 | 4/2004 |
| WO | WO 2004/029050 | 4/2004 |
| WO | WO 2004/041791 | 5/2004 |
| WO | WO 2004041791 | 5/2004 |
| WO | WO 2005/092890 | 10/2005 |
| WO | WO 2008/020405 | 2/2008 |
| WO | WO 2008020405 | 2/2008 |
| WO | WO 2008/038251 | 4/2008 |
| WO | WO 2008038251 | 4/2008 |
| WO | WO 2008/065626 | 6/2008 |
| WO | WO 2008065626 | 6/2008 |

OTHER PUBLICATIONS

Bergmeier, S.C., et al., Tetrahedron 1999, vol. 55, pp. 8025-8038.
Berry, C.R., Cycloaddition Reactions of Thiazollum Azomethine Ylides: Application to Pyrrolo[2,1b]thiazoles, Organic Letters, 2007, vol. 9, No. 21, 4099-4102.
Chemelli, R.M., Narcolepsy in orexin Knock Out Mice: Molecular Genetics of Sleep Regulation, Cell, Aug. 20, 1999, vol. 98, 437-451, Cell Press.
Danheiser, R.L., Reactions of (TrIalkylsllyl)vinylketenes with Lithium Ynolates: A New Benzannulation Strategy, Organic Letters, 2005, vol. 7, No. 18, 3905-3908.
Eissenstat, M.A., Aminoalkylindoles: Structure-Activity Relationships of Novel Cannabinoid Mimetics, Journal of Medicinal Chemistry, 1995, vol. 38, 3094-3105, American Chemical Society, Washington DC, USA.
Goldstein, S.W., et al., A Facile Synthesis of Methyl 2-Substituted-4-benzoxazolecarboxylates, Journal of Heterocyclic Chemistry, 1990, vol. 27, 335-336.
Gould, P.L., Salt Selection for Basic Drugs, International Journal of Pharmaceutics, 1986, vol. 33, 201-217.

(Continued)

*Primary Examiner* — Kamal Saeed
*Assistant Examiner* — Nyeemah A Grazier
(74) *Attorney, Agent, or Firm* — Hoxie & Associates LLC

(57) ABSTRACT

The invention relates to 3-aza-bicyclo[3.3.0]octane derivatives of the formula (I) wherein $R^1$, $R^2$, $R^3$, and A are as described in the description and their use as orexin receptor antagonists.

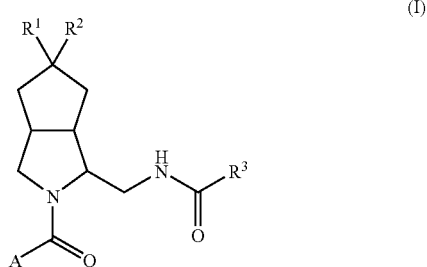

(I)

15 Claims, No Drawings

OTHER PUBLICATIONS

Greene, T.W., et al., Protective Groups in Organic Synthesis, Wiley Interscience, 1999.

Ishikawa, T., et al, Hetercycles, 1994, vol. 39, Issue 1, pp. 371-380.

Reetz, M.T., et al., Direct Geminal Dialkylatlon of Ketones Using Organotitanium Reagents. A Simple Entry Into Synthetic Tetrahydrocannabinoids J. Org. Chem., 1983 vol. 48, pp. 254-255.

Jao, E., et al., Tetrahedron Letters, 2003, vol. 44, pp. 5033, 5035.

Kawase, et al., The Syntheses of Benzofuran-carboxylic Acids and the Acetylation of Their Esters, Bulletin of the Chemical Society of Japan, 1967, vol. 40, No. 5, 1224-1231, Japan.

Mohamadi, F., et al., Total Synthesis and Biological Properties of Novel Antineoplastic (Chloromethyl)furanoindolines: An Asymmetric Hydroboration Mediated Synthesis of the Alkylation Subunits, Journal of Medicinal Chemistry, 1994, vol. 37, 232-239.

Reetz, M. T., et al., Angewandte Chemie, 1980, vol. 92 (11), pp. 931-933.

Reetz, M. T., et al., Chemische Berichte, 1985, vol. 118 (3), pp. 1050-1057.

Remington, The Science and Practice of Pharmacy, $21^{st}$ Edition (2005).

Sakurai, T. et al., Orexin & Orexin Receptors: A Family of Hypothalamic Neuropeptides and GProtein-Couples Receptors that Regulate Feeding Behavior, Cell, Feb. 20, 1998, vol. 92, 573-585, Cell Press.

Eicher, T., et al., The Chemistry of Heterocycles: Structures, Reactions, Synthesis, and Applications, $2^{nd}$ Edition 2003, Wiley, ISBN 978-3-527-30720-3.

* cited by examiner

3-AZA-BICYCLO[3.3.0]OCTANE COMPOUNDS

CROSS REFERENCE TO RELATED APPLICATIONS

This application is a United States Application under 35 U.S.C. 371 claiming benefit of PCT Application No. PCT/IB2008/052656, filed on Jul. 2, 2008, which claims the benefit of PCT Application No. PCT/IB2007/052598, filed on Jul. 3, 2007, the contents of each of which are incorporated herein by reference.

The present invention relates to novel 3-aza-bicyclo[3.3.0] octane compounds of formula (I) and their use as pharmaceuticals. The invention also concerns related aspects including processes for the preparation of the compounds, pharmaceutical compositions containing one or more compounds of formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451).

Orexin receptors are found in the mammalian brain and may have numerous implications in pathologies as known from the literature.

The present invention provides 3-aza-bicyclo[3.3.0]octane derivatives, which are non-peptide antagonists of human orexin receptors. These compounds are in particular of potential use in the treatment of e.g. eating disorders, drinking disorders, sleep disorders, or cognitive dysfunctions in psychiatric and neurologic disorders.

Up to now, several low molecular weight compounds are known having a potential to antagonise either specifically $OX_1$ or $OX_2$, or both receptors at the same time. Piperidine derivatives useful as orexin receptor antagonists are disclosed in WO01/96302. Morpholine derivatives useful as orexin receptor antagonists are disclosed in WO02/44172. N-Aroyl cyclic amine derivatives useful as orexin receptor antagonists are disclosed in WO02/90355.

The present invention describes for the first time 3-aza-bicyclo[3.3.0]octane compounds as orexin receptor antagonists.

i) A first aspect of the invention consists of a compound of the formula (I)

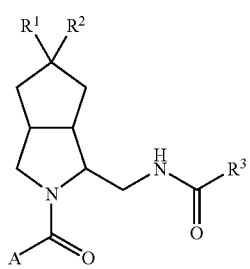

(I)

wherein
$R^1$ represents hydrogen, $(C_{1-4})$alkyl or fluorine;
$R^2$ represents hydrogen, $(C_{1-4})$alkyl or fluorine;
$R^3$ represents aryl, which is unsubstituted, mono-, di-, or tri-substituted, wherein the substituents are independently selected from the group consisting of $(C_{1-4})$alkyl, $(C_{1-4})$alkoxy, trifluoromethyl, trifluoromethoxy, and halogen;
or heteroaryl, which is unsubstituted, mono-, di-, or tri-substituted, wherein the substituents are independently selected from the group consisting of $(C_{1-4})$alkyl, $(C_{1-4})$alkoxy, halogen, and trifluoromethyl;
A represents

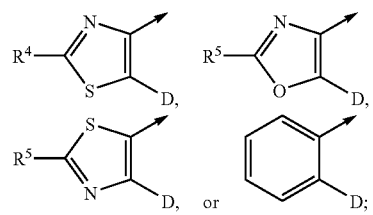

$R^4$ represents $(C_{1-4})$alkyl, or —$NR^6R^7$;
$R^5$ represents $(C_{1-4})$alkyl;
$R^6$ represents hydrogen, or $(C_{1-4})$alkyl;
$R^7$ represents hydrogen, or $(C_{1-4})$alkyl; and
D represents aryl, which is unsubstituted, mono-, di-, or tri-substituted, wherein the substituents are independently selected from the group consisting of $(C_{1-4})$alkyl, $(C_{1-4})$alkoxy, trifluoromethyl, and halogen.

ii) Another embodiment of the invention relates to compounds of formula (I) according to embodiment i), wherein $R^1$ represents hydrogen, or $(C_{1-4})$alkyl; and $R^2$ represents hydrogen, or $(C_{1-4})$alkyl.

The following paragraphs provide definitions of the various chemical moieties for the compounds according to the invention and are intended to apply uniformly throughout the specification and claims, unless an otherwise expressly set out definition provides a broader or narrower definition.

The term "halogen" means fluorine, chlorine, or bromine, preferably fluorine or chlorine.

The term "$(C_{1-4})$alkyl" means a straight-chain or branched-chain alkyl group with 1 to 4 carbon atoms. Examples of $(C_{1-4})$alkyl groups are methyl, ethyl, propyl, isopropyl, n-butyl, isobutyl, sec.-butyl and tert.-butyl. Preferred are methyl and ethyl. Most preferred is methyl.

The term "$(C_{1-4})$alkoxy" means a group of the formula $(C_{1-4})$alkyl-O— in which the term "$(C_{1-4})$alkyl" has the previously given significance. Examples of $(C_{1-4})$alkoxy groups are methoxy, ethoxy, n-propoxy, isopropoxy, n-butoxy, isobutoxy, sec.-butoxy and tert.-butoxy. Preferred are methoxy and ethoxy. Most preferred is methoxy.

The term "aryl" means a phenyl, a naphthyl, a 2,3-dihydro-benzofuranyl-, a benzo[1,3]dioxolyl-, a 2,3-dihydro-benzo[1,4]dioxinyl-, or a 4H-benzo[1,3]dioxinyl group. The aryl group is unsubstituted, mono-, di-, or tri-substituted, wherein the substituents are independently selected from the group consisting of $(C_{1-4})$alkyl, $(C_{1-4})$alkoxy, trifluoromethyl, trifluoromethoxy, and halogen. 2,3-Dihydro-benzofuranyl-, benzo[1,3]dioxolyl-, 2,3-dihydro-benzo[1,4]dioxinyl- and 4H-benzo[1,3]dioxinyl groups are preferably unsubstituted.

"D" representing "aryl" preferably means phenyl, which is unsubstituted, mono-, di-, or tri-substituted (preferred: mono- or di-substituted), wherein the substituents are independently selected from the group consisting of $(C_{1-4})$alkyl, $(C_{1-4})$ alkoxy, trifluoromethyl, and halogen. Examples of "D" representing "aryl" are phenyl, 3-methylphenyl, 4-methylphenyl, 3,4-dimethylphenyl, 4-ethylphenyl, 3-methoxyphenyl, 4-methoxyphenyl, 3-fluorophenyl, 4-fluorophenyl, 3,4-difluorophenyl, 3-chlorophenyl, 4-chlorophenyl, 3-trifluoromethylphenyl and 4-trifluoromethylphenyl.

"$R^3$" representing "aryl" preferably means phenyl, which is unsubstituted, mono-, di-, or tri-substituted (preferred: monosubstituted), wherein the substituents are independently selected from the group consisting ($C_{1-4}$)alkyl, ($C_{1-4}$)alkoxy, trifluoromethyl, trifluoromethoxy, and halogen (especially methyl, methoxy, fluoro, chloro, bromo, trifluoromethyl and trifluoromethoxy). Additionally, in another embodiment $R^3$ representing "aryl" means 2,3-dihydro-benzofuranyl; benzo[1,3]dioxolyl; 2,3-dihydro-benzo[1,4]dioxinyl; or 4H-benzo[1,3]dioxinyl (especially 2,3-dihydro-benzo[1,4]dioxinyl). Examples of $R^3$ representing "aryl" are 2,3-dihydro-benzo[1,4]dioxine-5-yl, 3-methylphenyl, 3-bromophenyl, 3-chlorophenyl, 3-fluorophenyl, 3-methoxyphenyl, 3-trifluoromethoxyphenyl, and 3-trifluoromethylphenyl. In addition to the above-listed examples, a further example is 2,3-dihydro-benzofuranyl.

The term "heteroaryl" means a 5- to 10-membered monocyclic or bicyclic aromatic ring containing 1, 2 or 3 heteroatoms, each independently selected from oxygen, nitrogen and sulfur. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl and imidazo[2,1-b]thiazolyl. In addition to the above-listed examples, a further example is pyrrolo[2,1-b]thiazolyl. The above-mentioned heteroaryl groups are unsubstituted, mono-, di-, or tri-substituted, wherein the substituents are independently selected from the group consisting of ($C_{1-4}$)alkyl, ($C_{1-4}$)alkoxy, halogen, and trifluoromethyl. Preferred heteroaryl groups are isoxazolyl, pyridyl, indazolyl, benzofuranyl, benzoxazolyl, benzisoxazolyl, benzoisothiazolyl, and imidazo[2,1-b]thiazolyl; and, in addition to the above-listed preferred heteroaryl groups, benzothiazolyl, pyrrolo[2,1-b]thiazolyl, and imidazo[1,2-a]pyridinyl, wherein the latter three groups form a particular sub-embodiment; wherein said groups are unsubstituted, mono-, di-, or tri-substituted (preferred unsubstituted, mono-, or di-substituted, most preferred unsubstituted, or mono-substituted) wherein the substituents are independently selected from the group consisting of ($C_{1-4}$)alkyl, ($C_{1-4}$)alkoxy, halogen, and trifluoromethyl (preferred ($C_{1-4}$)alkyl, ($C_{1-4}$)alkoxy, and halogen). If substituted, isoxazolyl, indazolyl, benzofuranyl, benzoxazolyl, and imidazo[2,1-b]thiazolyl groups are preferably mono- or di-substituted (preferred mono-substituted) with methyl. If substituted, pyridyl groups are preferably mono- or di-substituted (preferred mono-substituted) with substituents independently selected from the group consisting of methyl, methoxy, chloro, bromo and trifluoromethyl. If substituted, pyrrolo[2,1-b]thiazolyl groups are preferably mono- or di-substituted (preferred mono-substituted) with methyl. Benzothiazolyl and imidazo[1,2-a]pyridinyl groups are preferably unsubstituted. Examples of $R^3$ representing "heteroaryl" are 4-bromo-pyridine-2-yl, 5-bromo-pyridine-3-yl, 4-chloro-pyridine-2-yl, 5-chloro-pyridine-3-yl, 4-methyl-pyridine-2-yl, 5-methyl-pyridine-3-yl, 6-methyl-pyridine-2-yl, 2-methyl-pyridine-4-yl, 6-methoxy-pyridine-2-yl, 6-trifluoromethyl-pyridine-2-yl, 3,5-dimethyl-isoxazole-4-yl, 1-methyl-1H-indazole-3-yl, 2-methyl-benzofuran-4-yl, benzofuran-4-yl, benzo[d]isoxazole-3-yl, 2-methyl-benzoxazole-4-yl, benzo[d]isothiazole-3-yl, imidazo[2,1-b]thiazole-5-yl, imidazo[2,1-b]thiazole-6-yl, and 6-methyl-imidazo[2,1-b]-thiazole-5-yl. In addition to the above-listed examples of $R^3$ representing "heteroaryl", further examples are benzothiazol-7-yl, 3-methyl-benzofuran-4-yl, 6-methyl-pyrrolo[2,1-b]thiazol-7-yl, and imidazo[1,2-a]pyridin-3-yl.

Examples of "—$NR^6R^7$" groups are —$NH_2$ (preferred) and —$N(CH_3)_2$.

The term "acyl" as used in the specification means an aryl-CO—, an alkyl-CO—, or a heteroaryl-CO— group, such as for example A-CO—, or $R^3$—CO—, wherein A and $R^3$ have the meaning given for formula (I).

iii) A further embodiment of the invention relates to compounds of formula (I) according to embodiments i) or ii), wherein the configuration of the 3-aza-bicyclo[3.3.0]octane moiety is such that the —$CH_2$—NH—CO—$R^3$ substituent and the cyclopentane ring of the 3-aza-bicyclo[3.3.0]octane moiety are in trans relation (relative configuration (1S*,2S*,5R*)).

iv) A further embodiment of the invention relates to compounds of formula (I) according to embodiments i) or ii), wherein the configuration of the 3-aza-bicyclo[3.3.0]octane moiety is such that the —$CH_2$—NH—CO—$R^3$ substituent and the cyclopentane ring of the 3-aza-bicyclo[3.3.0]octane moiety are in cis relation (relative configuration (1R*,2S*,5S*)).

v) A further embodiment of the invention relates to compounds of formula (I) according to embodiments i) to iv), wherein the absolute configuration of the carbon center of the 3-aza-bicyclo[3.3.0]octane moiety to which the —$CH_2$—NH—CO—$R^3$ group is attached is (2S) as depicted in formula ($I_{E1}$)

Formula ($I_{E1}$)

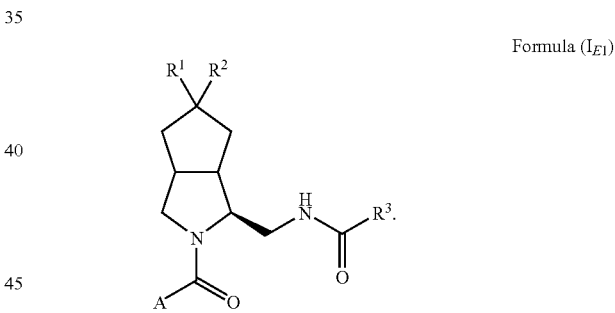

vi) A further embodiment of the invention relates to compounds of formula (I) according to embodiments i), ii), iii) or v), wherein the absolute configuration is as depicted in formula ($I_{E2}$)

Formula ($I_{E2}$)

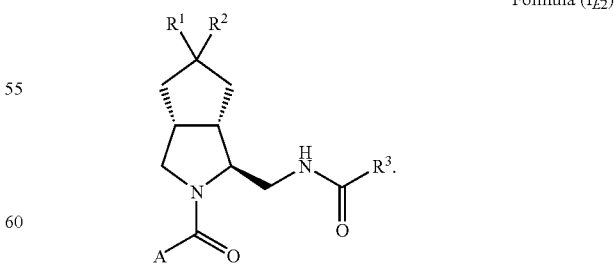

vii) A further embodiment of the invention relates to 3-aza-bicyclo[3.3.0]octane derivatives according to any one of embodiments i) to vi), wherein $R^1$ represents hydrogen, or methyl; and $R^2$ represents hydrogen.

viii) A further embodiment of the invention relates to 3-aza-bicyclo[3.3.0]octane derivatives according to any one of embodiments i) to vii), wherein A represents

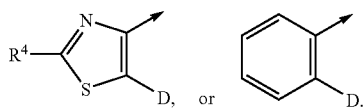

ix) A further embodiment of the invention relates to 3-aza-bicyclo[3.3.0]octane derivatives according to any one of embodiments i) to viii), wherein A represents

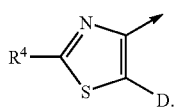

x) A further embodiment of the invention relates to 3-aza-bicyclo[3.3.0]octane derivatives according to any one of embodiments i) to ix), wherein
$R^4$ represents methyl, or —$NH_2$ (especially methyl).

xi) A further embodiment of the invention relates to 3-aza-bicyclo[3.3.0]octane derivatives according to any one of embodiments i) to viii), wherein A represents

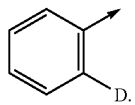

xii) A further embodiment of the invention relates to 3-aza-bicyclo[3.3.0]octane derivatives according to any one of embodiments i) to xi), wherein D represents phenyl, which is unsubstituted, mono-, di-, or tri-substituted, wherein the substituents are independently selected from the group consisting of ($C_{1-4}$)alkyl, ($C_{1-4}$)alkoxy, trifluoromethyl, and halogen (especially the phenyl is mono-, or disubstituted, wherein said substituents are preferably in position(s)$_3$, and/or 4).

xiii) A further embodiment of the invention relates to 3-aza-bicyclo[3.3.0]octane derivatives according to any one of embodiments i) to xii), wherein $R^3$ represents phenyl, which is unsubstituted, mono-, di-, or tri-substituted, wherein the substituents are independently selected from the group consisting of ($C_{1-4}$)alkyl, ($C_{1-4}$)alkoxy, trifluoromethyl, trifluoromethoxy, and halogen; 2,3-dihydro-benzofuranyl; benzo[1,3]dioxolyl; 2,3-dihydro-benzo[1,4]dioxinyl; 4H-benzo[1,3]dioxinyl; or an isoxazolyl, a pyridyl, an indazolyl, a benzofuranyl, a benzoxazolyl, a benzisoxazolyl, or an imidazo[2,1-b]thiazolyl group, wherein said groups are unsubstituted, mono-, di-, or tri-substituted, wherein the substituents are independently selected from the group consisting of ($C_{1-4}$)alkyl, ($C_{1-4}$)alkoxy, halogen, and trifluoromethyl.

xiv) A further embodiment of the invention relates to 3-aza-bicyclo[3.3.0]octane derivatives according to any one of embodiments i) to xiii), wherein $R^3$ represents phenyl, which is unsubstituted, mono-, di-, or tri-substituted, wherein the substituents are independently selected from the group consisting of ($C_{1-4}$)alkyl, ($C_{1-4}$)alkoxy, trifluoromethyl, trifluoromethoxy, and halogen; 2,3-dihydro-benzofuranyl; benzo[1,3]dioxolyl; 2,3-dihydro-benzo[1,4]dioxinyl; 4H-benzo[1,3]dioxinyl; or an isoxazolyl, a pyridyl, an indazolyl, a benzofuranyl, a benzoxazolyl, a benzisoxazolyl, or a benzoisothiazolyl group, wherein said groups are unsubstituted, mono-, di-, or tri-substituted, wherein the substituents are independently selected from the group consisting of ($C_{1-4}$)alkyl, ($C_{1-4}$)alkoxy, halogen, and trifluoromethyl.

xv) A further embodiment of the invention relates to 3-aza-bicyclo[3.3.0]octane derivatives according to any one of embodiments i) to xiii), wherein $R^3$ represents an isoxazolyl, a pyridyl, an indazolyl, a benzofuranyl, a benzoxazolyl, a benzisoxazolyl, a benzoisothiazolyl, or an imidazo[2,1-b]thiazolyl group, wherein said groups are unsubstituted, mono-, di-, or tri-substituted, wherein the substituents are independently selected from the group consisting of ($C_{1-4}$)alkyl, ($C_{1-4}$)alkoxy, halogen, and trifluoromethyl.

xvi) A further embodiment of the invention relates to 3-aza-bicyclo[3.3.0]octane derivatives according to any one of embodiments i) to xiii), wherein $R^3$ represents phenyl, which is unsubstituted, mono-, di-, or tri-substituted, wherein the substituents are independently selected from the group consisting of ($C_{1-4}$)alkyl, ($C_{1-4}$)alkoxy, trifluoromethyl, trifluoromethoxy, and halogen; or a 2,3-dihydro-benzofuranyl-, a benzo[1,3]dioxolyl-, a 2,3-dihydro-benzo[1,4]dioxinyl-, or a 4H-benzo[1,3]dioxinyl-group (especially a 2,3-dihydro-benzo[1,4]dioxinyl-group), said groups being unsubstituted.

xvii) A further embodiment of the invention relates to 3-aza-bicyclo[3.3.0]octane derivatives according to any one of embodiments i) to xiii) or xv), wherein $R^3$ represents

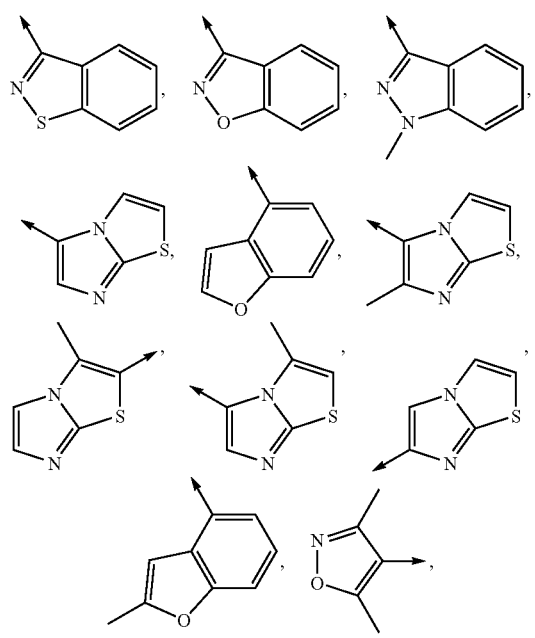

or pyridyl, which is mono-substituted, wherein the substituent is selected from the group consisting of methyl, methoxy, chloro, bromo and trifluoromethyl.

xviii) A further embodiment of the invention relates to 3-aza-bicyclo[3.3.0]octane derivatives according to any one of embodiments i) to xiv), wherein $R^3$ represents

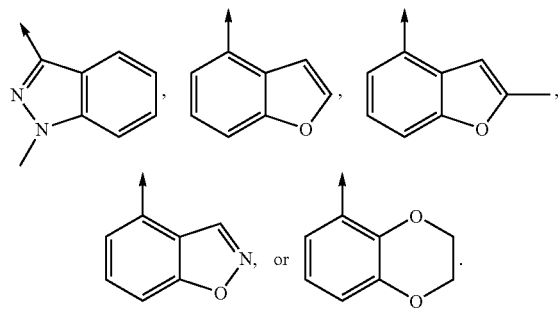

xix) A further embodiment of the invention relates to 3-aza-bicyclo[3.3.0]octane derivatives according to any one of embodiments i) to xiii), xv), or xvii), wherein $R^3$ represents

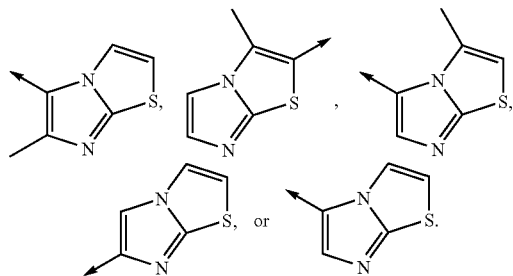

xx) A further embodiment of the invention relates to 3-aza-bicyclo[3.3.0]octane derivatives according to any one of embodiments i) to xiii), xv), xvii), or xix), wherein $R^3$ represents

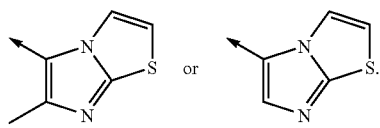

xxi) A further embodiment of the invention relates to 3-aza-bicyclo[3.3.0]octane derivatives according to any one of embodiments i) to vi), ix), x) or xii), wherein $R^1$ and $R^2$ both represent fluorine.

xxii) A further embodiment of the invention relates to 3-aza-bicyclo[3.3.0]octane derivatives according to any one of embodiments i) to xii), wherein $R^3$ represents phenyl, which is unsubstituted, mono-, di-, or tri-substituted, wherein the substituents are independently selected from the group consisting of $(C_{1-4})$alkyl, $(C_{1-4})$alkoxy, trifluoromethyl, trifluoromethoxy, and halogen; 2,3-dihydro-benzofuranyl; benzo[1,3]dioxolyl; 2,3-dihydro-benzo[1,4]dioxinyl; 4H-benzo[1,3]dioxinyl; or an isoxazolyl, a pyridyl, an indazolyl, a benzofuranyl, a benzoxazolyl, a benzisoxazolyl, a benzothiazolyl, a benzoisothiazolyl, a pyrrolo[2,1-b]thiazolyl, an imidazo[1,2-a]pyridinyl, or an imidazo[2,1-b]thiazolyl group, wherein said groups are unsubstituted, mono-, di-, or tri-substituted, wherein the substituents are independently selected from the group consisting of $(C_{1-4})$alkyl, $(C_{1-4})$alkoxy, halogen, and trifluoromethyl.

xxiii) A further embodiment of the invention relates to 3-aza-bicyclo[3.3.0]octane derivatives according to any one of embodiments i) to xii), xxi) or xxii), wherein $R^3$ represents

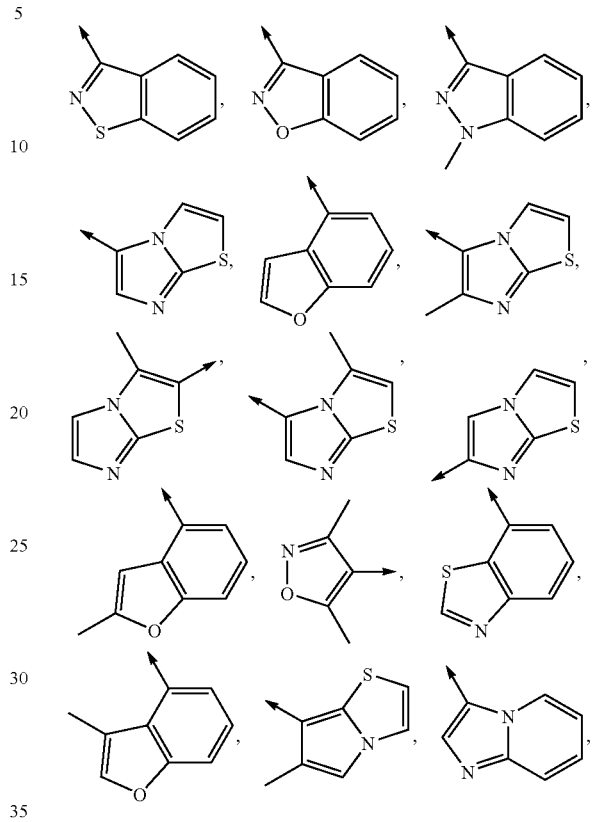

or pyridyl, which is mono-substituted, wherein the substituent is selected from the group consisting of methyl, methoxy, chloro, bromo and trifluoromethyl.

xxiv) A further embodiment of the invention relates to 3-aza-bicyclo[3.3.0]octane derivatives according to embodiment xxi), wherein $R^3$ represents a group selected from the group consisting of 2,3-dihydro-benzofuran-4-yl, 2,3-dihydro-benzo[1,4]dioxin-5-yl, 1-methyl-1H-indazole-3-yl, benzothiazol-7-yl, 2-methyl-benzofuran-4-yl, 3-methyl-benzofuran-4-yl, 6-methyl-pyrrolo[2,1-b]thiazol-7-yl, imidazo[1,2-a]pyridin-3-yl, and 6-methyl-imidazo[2,1-b]-thiazole-5-yl.

xxv) A further embodiment of the invention relates to 3-aza-bicyclo[3.3.0]octane derivatives of formula (I) according to embodiments i) to vi) wherein at least one, preferably all of the following characteristics are present:

$R^1$ represents hydrogen, or methyl;
$R^2$ represents hydrogen;
$R^3$ represents phenyl, which is unsubstituted, mono-, or di-substituted, wherein the substituents are independently selected from the group consisting of $(C_{1-4})$alkyl, $(C_{1-4})$alkoxy, trifluoromethyl, trifluoromethoxy, and halogen; 2,3-dihydro-benzo[1,4]dioxinyl; an isoxazolyl, an indazolyl, a benzofuranyl, a benzoxazolyl, a benzisoxazolyl, a benzoisothiazolyl, or an imidazo[2,1-b]thiazolyl group, wherein said groups are unsubstituted, or mono-substituted, wherein the substituent is selected from the group consisting of $(C_{1-4})$alkyl; or pyridyl which is unsubstituted, or mono-substituted, wherein the substituent is selected from the group consisting of $(C_{1-4})$alkyl, $(C_{1-4})$alkoxy, halogen, and trifluoromethyl;

A represents

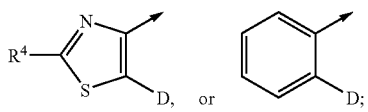

R[4] represents (C$_{1-4}$)alkyl, or —NH$_2$;

D represents aryl, which is unsubstituted, mono-, or di-substituted, wherein the substituents are independently selected from the group consisting of (C$_{1-4}$)alkyl, (C$_{1-4}$) alkoxy, trifluoromethyl, and halogen.

xxvi) A further embodiment of the invention relates to 3-aza-bicyclo[3.3.0]octane derivatives of formula (I) according to embodiments i) to vi) wherein at least one, preferably all of the following characteristics are present:

R[1] and R[2] both represent hydrogen; or R[1] represents methyl and R[2] represents hydrogen; or R[1] and R[2] both represent fluorine;

R[3] represents phenyl, which is unsubstituted, mono-, or di-substituted, wherein the substituents are independently selected from the group consisting of (C$_{1-4}$)alkyl, (C$_{1-4}$)alkoxy, trifluoromethyl, trifluoromethoxy, and halogen; 2,3-dihydro-benzo[1,4]dioxinyl; 2,3-dihydro-benzofuranyl; an isoxazolyl, an indazolyl, a benzofuranyl, a benzoxazolyl, a benzisoxazolyl, a benzothiazolyl, benzoisothiazolyl, a pyrrolo[2,1-b]thiazolyl, an imidazo[1,2-a]pyridinyl, or an imidazo[2,1-b]thiazolyl group, wherein said groups are unsubstituted, or mono-substituted, wherein the substituent is selected from the group consisting of (C$_{1-4}$)alkyl; or pyridyl which is unsubstituted, or mono-substituted, wherein the substituent is selected from the group consisting of (C$_{1-4}$)alkyl, (C$_{1-4}$)alkoxy, halogen, and trifluoromethyl;

A represents

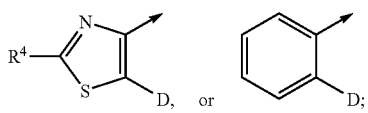

R[4] represents (C$_{1-4}$)alkyl, or —NH$_2$;

D represents aryl, which is unsubstituted, mono-, or di-substituted, wherein the substituents are independently selected from the group consisting of (C$_{1-4}$)alkyl, (C$_{1-4}$) alkoxy, trifluoromethyl, and halogen.

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference to a compound of formula (I) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

xxvii) Examples of compounds of formula (I) according to embodiment i) are selected from the group consisting of:

2,3-Dihydro-benzo[1,4]dioxine-5-carboxylic acid-(1S,2S,5R)-[3-(2-methyl-5-m-tolyl-thiazole-4-carbonyl)-3-aza-bicyclo[3.3.0]oct-2-ylmethyl]-amide;

Benzo[d]isothiazole-3-carboxylic acid-(1S,2S,5R)-[3-(2-methyl-5-m-tolyl-thiazole-4-carbonyl)-3-aza-bicyclo[3.3.0]oct-2-ylmethyl]-amide;

(1S,2S,5R)-3-Bromo-N-[7-methyl-3-(2-methyl-5-m-tolyl-thiazole-4-carbonyl)-3-aza-bicyclo[3.3.0]oct-2-ylmethyl]-benzamide;

(1S,2S,5R)-3-Chloro-N-[7-methyl-3-(2-methyl-5-m-tolyl-thiazole-4-carbonyl)-3-aza-bicyclo[3.3.0]oct-2-ylmethyl]-benzamide;

(1S,2S,5R)-3-Fluoro-N-[7-methyl-3-(2-methyl-5-m-tolyl-thiazole-4-carbonyl)-3-aza-bicyclo[3.3.0]oct-2-ylmethyl]-benzamide;

(1S,2S,5R)-3-Methoxy-N-[7-methyl-3-(2-methyl-5-m-tolyl-thiazole-4-carbonyl)-3-aza-bicyclo[3.3.0]oct-2-ylmethyl]-benzamide;

(1S,2S,5R)—N-[7-methyl-3-(2-methyl-5-m-tolyl-thiazole-4-carbonyl)-3-aza-bicyclo[3.3.0]oct-2-ylmethyl]-3-trifluoromethyl-benzamide;

(1S,2S,5R)-3-Methyl-N-[7-methyl-3-(2-methyl-5-m-tolyl-thiazole-4-carbonyl)-3-aza-bicyclo[3.3.0]oct-2-ylmethyl]-benzamide;

(1S,2S,5R)—N-[7-methyl-3-(2-methyl-5-m-tolyl-thiazole-4-carbonyl)-3-aza-bicyclo[3.3.0]oct-2-ylmethyl]-3-trifluoromethoxy-benzamide;

6-Trifluoromethyl-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;

6-Methoxy-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;

4-Bromo-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;

4-Chloro-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;

4-Methyl-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;

(1S,2S,5R)-5-Bromo-N-[7-methyl-3-(2-methyl-5-m-tolyl-thiazole-4-carbonyl)-3-aza-bicyclo[3.3.0]oct-2-ylmethy]-nicotinamide;

(1S,2S,5R)-5-Chloro-N-[7-methyl-3-(2-methyl-5-m-tolyl-thiazole-4-carbonyl)-3-aza-bicyclo[3.3.0]oct-2-ylmethy]-nicotinamide;

(1S,2S,5R)-5-Methyl-N-[7-methyl-3-(2-methyl-5-m-tolyl-thiazole-4-carbonyl)-3-aza-bicyclo[3.3.0]oct-2-ylmethy]-nicotinamide;

Benzofuran-4-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;

2-Methyl-benzofuran-4-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;

2-Methyl-benzoxazole-4-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;

2,3-Dihydro-benzo[1,4]dioxine-5-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;

1-Methyl-indazole-3-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
3,5-Dimethyl-isoxazole-4-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
Benzo[d]isoxazole-3-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
(1S,2S,5R)-2-Methyl-N-[7-methyl-3-(2-methyl-5-m-tolyl-thiazole-4-carbonyl)-3-aza-bicyclo[3.3.0]oct-2-ylmethyl]-isonicotinamide;
Benzo[d]isoxazole-3-carboxylic acid-(1S,2S,5R)-[3-(2-methyl-5-m-tolyl-thiazole-4-carbonyl)-3-aza-bicyclo[3.3.0]oct-2-ylmethyl]-amide; and
Benzo[d]isothiazole-3-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
wherein it is well understood that in case the above-listed compounds contain a (1S,2S,5R)-7-methyl-3-aza-bicyclo[3.3.0]oct-2-ylmethyl moiety, such moiety may be in absolute (1S,2S,5R,7R)- or in absolute (1S,2S,5R,7S)-configuration.

xxviii) In addition to the compounds listed in embodiment xxvii), further examples of compounds of formula (I) according to embodiment i) are selected from the group consisting of:

Imidazo[2,1-b]thiazole-5-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
Imidazo[2,1-b]thiazole-5-carboxylic acid-(1S,2S,5R)-[3-(2-methyl-5-m-tolyl-thiazole-4-carbonyl)-3-aza-bicyclo[3.3.0]oct-2-ylmethyl]-amide;
Imidazo[2,1-b]thiazole-6-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
6-Methyl-imidazo[2,1-b]thiazole-5-carboxylic acid-(1S,2S,5R)-[3-(2-methyl-5-m-tolyl-thiazole-4-carbonyl)-3-aza-bicyclo[3.3.0]oct-2-ylmethyl]-amide;
6-Methyl-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
6-Methyl-imidazo[2,1-b]thiazole-5-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
6-Methyl-imidazo[2,1-b]thiazole-5-carboxylic acid-(1S,2S,5R)-{3-[5-(3-methoxy-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[5-(3-methoxy-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S,2S,5R)-{3-[2-methyl-5-(3-trifluoromethyl-phenyl)-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{7-methyl-3-[2-methyl-5-(3-trifluoromethyl-phenyl)-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[5-(3-fluoro-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[5-(3-fluoro-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S,2S,5R)-[7-methyl-3-(2-methyl-5-p-tolyl-thiazole-4-carbonyl)-3-aza-bicyclo[3.3.0]oct-2-ylmethyl]-amide;
6-Methyl-imidazo[2,1-b]thiazole-5-carboxylic acid-(1S,2S,5R)-[3-(2-methyl-5-p-tolyl-thiazole-4-carbonyl)-3-aza-bicyclo[3.3.0]oct-2-ylmethyl]-amide;
6-Methyl-imidazo[2,1-b]thiazole-5-carboxylic acid-(1S,2S,5R)-{3-[5-(3-chloro-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[5-(3-chloro-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S,2S,5R)-{3-[5-(4-methoxy-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[5-(4-methoxy-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S,2S,5R)-{3-[5-(4-ethyl-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S,2S,5R)-{7-methyl-3-[2-methyl-5-(4-trifluoromethyl-phenyl)-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[5-(4-fluoro-phenyl)-2-methyl-thiazole-4-carbonyl]-7-methyl-3-aza-bicyclo[3.3.0]oct-2-ylmethyl}-amide;
6-Methyl-imidazo[2,1-b]-thiazole-5-carboxylic acid-(1S,2S,5R)-{7-methyl-3-[2-methyl-5-phenyl-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[5-(3,4-dimethyl-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S,2S,5R)-{3-[5-(3,4-dimethyl-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[5-(3,4-difluoro-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S,2S,5R)-{3-[5-(3,4-difluoro-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-[3-(2-amino-5-phenyl-thiazole-4-carbonyl)-7-methyl-3-aza-bicyclo[3.3.0]oct-2-ylmethyl]-amide;
6-Methyl-imidazo[2,1-b]thiazole-5-carboxylic acid-(1S,2S,5R)-[3-(biphenyl-2-carbonyl)-7-methyl-3-aza-bicyclo[3.3.0]oct-2-ylmethyl]-amide;
6-Methyl-imidazo[2,1-b]thiazole-5-carboxylic acid-(1S,2S,5R)-[7-methyl-3-(3'-methyl-biphenyl-2-carbonyl)-3-aza-bicyclo[3.3.0]oct-2-ylmethyl]-amide;
6-Methyl-imidazo[2,1-b]-thiazole-5-carboxylic acid-(1S,2S,5R)-[7-methyl-3-(4'-methyl-biphenyl-2-carbonyl)-3-aza-bicyclo[3.3.0]oct-2-ylmethyl]-amide;
6-Methyl-imidazo[2,1-b]-thiazole-5-carboxylic acid-(1S,2S,5R)-[7-methyl-3-(4'-fluoro-biphenyl-2-carbonyl)-3-aza-bicyclo[3.3.0]oct-2-ylmethyl]-amide;
6-Methyl-imidazo[2,1-b]-thiazole-5-carboxylic acid-(1S,2S,5R)-[7-methyl-3-(3'-methoxy-biphenyl-2-carbonyl)-3-aza-bicyclo[3.3.0]oct-2-ylmethyl]-amide;

6-Methyl-imidazo[2,1-b]-thiazole-5-carboxylic acid-(1S,2S,5R)-[7-methyl-3-(4'-chloro-biphenyl-2-carbonyl)-3-aza-bicyclo[3.3.0]oct-2-ylmethyl]-amide;
6-Methyl-imidazo[2,1-b]thiazole-5-carboxylic acid-(1S,2S,5R)-[3-(biphenyl-2-carbonyl)-3-aza-bicyclo[3.3.0]oct-2-ylmethyl]-amide;
6-Methyl-imidazo[2,1-b]-thiazole-5-carboxylic acid-(1S,2S,5R)-[3-(4'-fluoro-biphenyl-2-carbonyl)-3-aza-bicyclo[3.3.0]oct-2-ylmethyl]-amide;
6-Methyl-imidazo[2,1-b]-thiazole-5-carboxylic acid-(1S,2S,5R)-[3-(3'-methyl-biphenyl-2-carbonyl)-3-aza-bicyclo[3.3.0]oct-2-ylmethyl]-amide;
6-Methyl-imidazo[2,1-b]-thiazole-5-carboxylic acid-(1S,2S,5R)-[3-(3'-methoxy-biphenyl-2-carbonyl)-3-aza-bicyclo[3.3.0]oct-2-ylmethyl]-amide;
6-Methyl-imidazo[2,1-b]-thiazole-5-carboxylic acid-(1S,2S,5R)-[3-(2-methyl-5-phenyl-thiazole-4-carbonyl)-3-aza-bicyclo[3.3.0]oct-2-ylmethyl]-amide;
6-Methyl-imidazo[2,1-b]thiazole-5-carboxylic acid-(1S,2S,5R)-{3-[5-(4-fluoro-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[5-(4-ethyl-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[5-(4-chloro-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[2-methyl-5-(4-trifluoromethyl-phenyl)-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[2-amino-5-(3-methyl-phenyl)-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{3-[2-amino-5-(3-fluoro-phenyl)-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-[3-(2-amino-5-phenyl-thiazole-4-carbonyl)-3-aza-bicyclo[3.3.0]oct-2-ylmethyl]-amide;
6-Methyl-imidazo[2,1-b]thiazole-5-carboxylic acid-(1S,2S,5R)-{7-methyl-3-[2-amino-5-(3-methyl-phenyl)-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{7-methyl-3-[2-amino-5-(4-fluoro-phenyl)-thiazole-4-carbonyl]-3-aza-bicyclo[3.3.0]oct-2-ylmethyl}-amide;
6-Methyl-imidazo[2,1-b]thiazole-5-carboxylic acid-(1S,2S,5R)-{7-methyl-3-[2-amino-5-(3-fluoro-phenyl)-thiazole-4-carbonyl]-3-aza-bicyclo[3.3.0]oct-2-ylmethyl}-amide; and
Imidazo[2,1-b]thiazole-6-carboxylic acid-(1S,2S,5R)-[3-(2-methyl-5-m-tolyl-thiazole-4-carbonyl)-3-aza-bicyclo[3.3.0]oct-2-ylmethyl]-amide;
wherein it is well understood that in case the above-listed compounds contain a (1S,2S,5R)-7-methyl-3-aza-bicyclo[3.3.0]oct-2-ylmethyl moiety, such moiety may be in absolute (1S,2S,5R,7R)- or in absolute (1S,2S,5R,7S)-configuration.

xxix) In addition to the compounds listed in embodiments xxvii) and xxviii), further examples of compounds of formula (I) according to embodiment i) are selected from the group consisting of:
2-Methyl-benzofuran-4-carboxylic acid-(1S,2S,5R)-[7,7-difluoro-3-(2-methyl-5-m-tolyl-thiazole-4-carbonyl)-3-aza-bicyclo[3.3.0]oct-3-ylmethyl]-amide;
3-Methyl-benzofuran-4-carboxylic acid-(1S,2S,5R)-[7,7-difluoro-3-(2-methyl-5-m-tolyl-thiazole-4-carbonyl)-3-aza-bicyclo[3.3.0]oct-3-ylmethyl]-amide;
2,3-Dihydro-benzofuran-4-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide;
2,3-Dihydro-benzo[1,4]dioxine-5-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide;
Benzothiazole-7-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide;
6-Methyl-pyrrolo[2,1-b]thiazole-7-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide;
Imidazo[1,2-a]pyridine-3-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide;
1-Methyl-indazole-3-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide; and
6-Methyl-imidazo[2,1-b]-thiazole-5-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide.

The compounds of formula (I) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I).

The compounds according to formula (I) are suitable and/or may be used for the preparation of a medicament for the prevention or treatment of diseases selected from the group consisting of dysthymic disorders including major depression and cyclothymia, affective neurosis, all types of manic depressive disorders, delirium, psychotic disorders, schizophrenia, catatonic schizophrenia, delusional paranoia, adjustment disorders and all clusters of personality disorders; schizoaffective disorders; anxiety disorders including generalized anxiety, obsessive compulsive disorder, posttraumatic stress disorder, panic attacks, all types of phobic anxiety and avoidance; separation anxiety; all psychoactive substance use, abuse, seeking and reinstatement; all types of psychological or physical addictions, dissociative disorders including multiple personality syndromes and psychogenic amnesias; sexual and reproductive dysfunction; psychosexual dysfunction and addiction; tolerance to narcotics or withdrawal from narcotics; increased anaesthetic risk, anaesthetic responsiveness; hypothalamic-adrenal dysfunctions; disturbed biological and circadian rhythms; sleep disturbances associated with diseases such as neurological disorders including neuropathic pain and restless leg syndrome; sleep apnea; narcolepsy; chronic fatigue syndrome; insomnias related to psychiatric disorders; all types of idiopathic insomnias and parasomnias; sleep-wake schedule disorders including jet-lag; all dementias and cognitive dysfunctions in the healthy population and in psychiatric and neurological disorders; mental dysfunctions of aging; all types of amnesia; severe mental retardation; dyskinesias and muscular diseases; muscle spasticity, tremors, movement disorders; spontaneous and medication-induced dyskinesias; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; epilepsy; seizure disorders; absence seizures, complex partial and generalized seizures; Lennox-Gastaut syndrome; migraine and headache; pain disorders; anaesthesia and analgesia; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; dental pain; pain related to infection e.g. by HIV; post-chemotherapy pain; post-stroke pain; postoperative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; appetite, taste, eating, or drinking disorders; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence; asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; ischemic or haemorrhagic stroke; all types of cerebrovascular disorders including subarachnoid haemorrhage, ischemic and hemorrhagic stroke and vascular dementia; chronic renal failure and other renal diseases; gout; kidney cancer; urinary incontinence; and other diseases related to general orexin system dysfunctions.

Compounds of formula (I) are particularly suitable and/or may be used for the preparation of a medicament for the treatment of diseases or disorders selected from the group consisting of all types of sleep disorders, of stress-related syndromes, of psychoactive substance use, abuse, seeking and reinstatement, of cognitive dysfunctions in the healthy population and in psychiatric and neurologic disorders, of eating or drinking disorders.

Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake. Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance. Psychoactive substance use, abuse, seeking and reinstatement are defined as all types of psychological or physical addictions and their related tolerance and dependence components. Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

In a further preferred embodiment of the invention compounds of formula (I) are particularly suitable for the treatment of diseases or disorders selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders.

In another preferred embodiment of the invention compounds of formula (I) are particularly suitable and/or may be used for the preparation of a medicament for the treatment of diseases or disorders selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another preferred embodiment of the invention compounds of formula (I) are particularly suitable and/or may be used for the preparation of a medicament for the treatment of diseases or disorders selected from the group consisting of eating disorders that comprise metabolic dysfunction; dysregulated appetite control; compulsive obesities; emeto-bulimia or anorexia nervosa.

In another preferred embodiment of the invention compounds of formula (I) are particularly suitable and/or may be used for the preparation of a medicament for the treatment of diseases or disorders selected from the group consisting of psychoactive substance use, abuse, seeking and reinstatement that comprise all types of psychological or physical addictions and their related tolerance and dependence components.

Preparation of Compounds of Formula (I):

A further aspect of the invention is a process for the preparation of compounds of formula (I). Compounds according to formula (I) of the present invention can be prepared according to the sequence of reactions outlined in the schemes below wherein A, D, $R^1$, $R^2$, $R^3$, $R^4$, $R^5$, $R^6$ and $R^7$ are as defined for formula (I). Other abbreviations used are defined in the experimental section. In some instances the generic groups A, D, $R^1$, $R^2$, $R^3$, $R^4$, $R^5$, $R^6$ and $R^7$ might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as are necessary are in place.

In general, all chemical transformations can be performed according to well-known standard methodologies as described in the literature or as described in the procedures below. The compounds obtained may also be converted into pharmaceutically acceptable salts thereof in a manner known per se.

3-Aza-bicyclo[3.3.0]octane derivatives of formula (I) are prepared from protected 3-aza-bicyclo[3.3.0]octane derivatives of structure (1) or structure (2) as shown in scheme 1. Compounds of structure (1) are transformed into compounds of structure (2) by replacement of the benzyl protecting group with a Boc group via hydrogenolysis and subsequent reaction with Boc$_2$O. The alcohol (2) is oxidized, for example under Swern conditions, to give the corresponding aldehyde (3). Reductive amination with benzylamine in the presence of a reducing agent such as NaBH(OAc)$_3$ followed by the removal of the benzyl group by hydrogenolysis furnishes the primary amine (4). The use of commercially available, enantiomerically pure 1-phenyl-ethylamine instead of benzylamine in the first step of the above sequence, separation of the so formed diastereoisomers by means known to the person skilled in the art, followed by removal of the 1-phenyl-ethyl group by hydrogenolysis as described leads to the corresponding enantiomerically pure amines (4). Acylation of amine (4) with carboxylic acid derivatives R$^3$—COOH in the presence of a coupling reagent such as TBTU results in the formation of amides (5) which, after removal of the Boc-group under acidic conditions, are acylated with carboxylic acid derivatives A-COOH using amide coupling reagents such as TBTU to give compounds of formula (I).

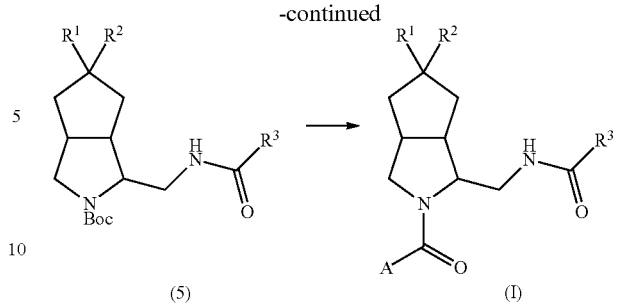

Alternatively, 3-aza-bicyclo[3.3.0]octane derivatives of formula (I) are prepared from amines of structure (4) as shown in scheme 2. Amines of structure (4) are protected by reaction with ethyl trifluoroacetate in aprotic solvents such as THF to give trifluoroacetamide derivatives (6). Removal of the Boc protecting group under acidic conditions such as TFA in DCM yields amine derivatives (7), which are then coupled with a carboxylic acid derivative A-COOH in the presence of a coupling reagent such as TBTU to yield amide derivatives (8).

Scheme 2: Synthesis of compounds of formula (I)

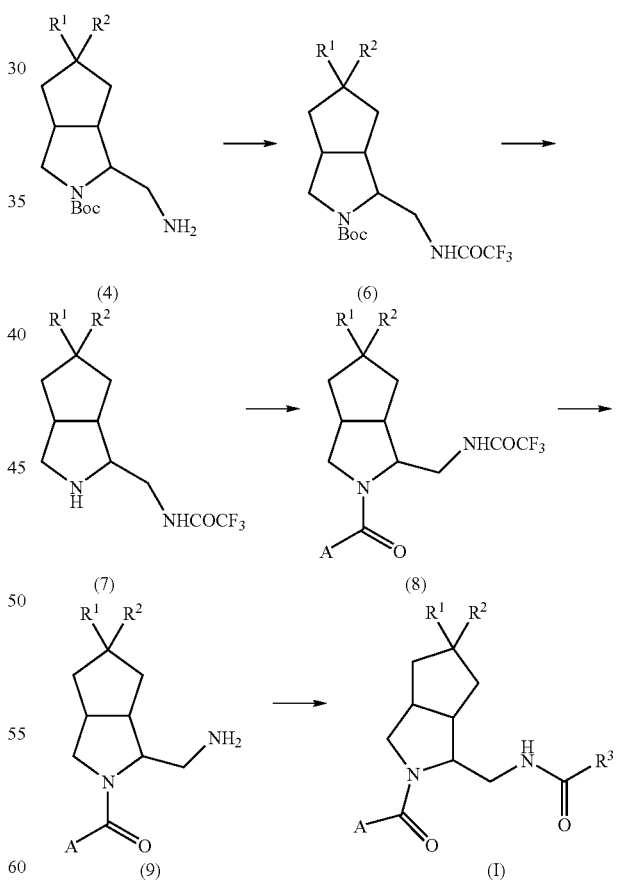

Scheme 1: Synthesis of compounds of formula (I), wherein R$^1$ and R$^2$ are hydrogen

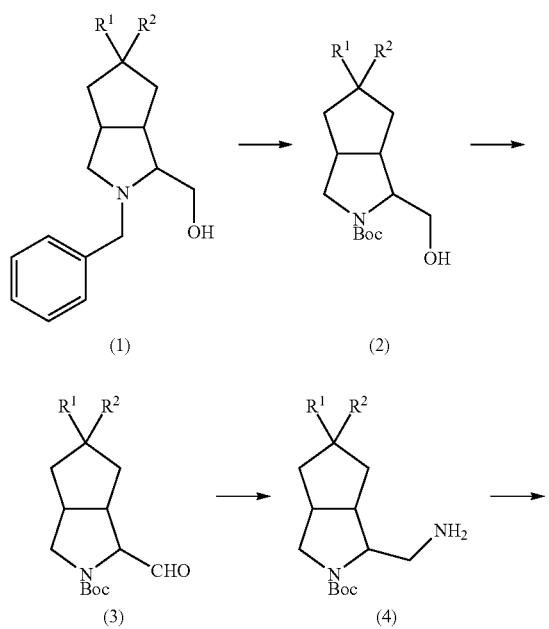

After deprotection of the trifluoroacetamide under basic conditions such as K$_2$CO$_3$ in MeOH/water mixtures, amine derivatives (9) are obtained which are coupled with carboxylic acid derivatives R$^3$—COOH in the presence of a coupling reagent such as TBTU to compounds of formula (I).

3-Aza-bicyclo[3.3.0]octane derivatives of structure (1), wherein $R^1$ and $R^2$ represent hydrogen are prepared as described in the literature (WO03/062265; Jao E. et al *Tetrahedron Letters,* 2003, 44, 5033-5035). Alternatively, 3-aza-bicyclo[3.3.0]octane derivatives of structure (1) are prepared from known compounds of structure (10) in scheme 3 (Bergmeier S. C. et al *Tetrahedron* 1999, 55, 8025-8038) by protecting the amine with a benzyl group using for example benzylbromide as alkylating reagent and reduction of the carboxylic acid to the alcohol using methods well known in the art such as LAH in THF. Alternatively, compounds of structure (10) can be protected with a Boc group and reduced to provide compounds of structure (2)

Scheme 3: Synthesis of compounds of structure (1), wherein $R^1$ and $R^2$ represent hydrogen

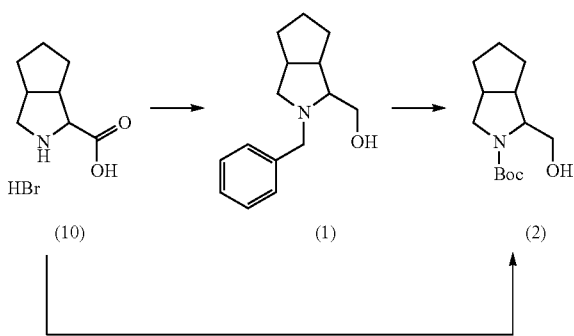

Compounds of structure (1), wherein $R^1$ represents methyl and $R^2$ represents hydrogen, are prepared from the known ketene cycloadduct (11) (Jao E. et al *Tetrahedron Letters,* 2003, 44, 5033-5035) as shown in scheme 5. Hydrogenation of the double bond gives the intermediate (12), which is then transformed to the desired alcohol of structure (1), wherein $R^1$ represents methyl and $R^2$ represents hydrogen, using excess of LAH in aprotic solvents such as THF under reflux conditions.

Scheme 5: Synthesis of compounds of structure (1), wherein $R^1$ represents methyl and $R^2$ represents hydrogen

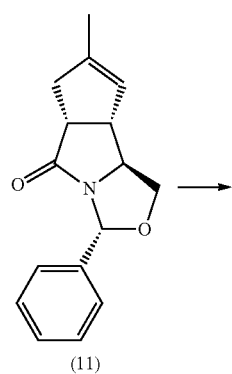

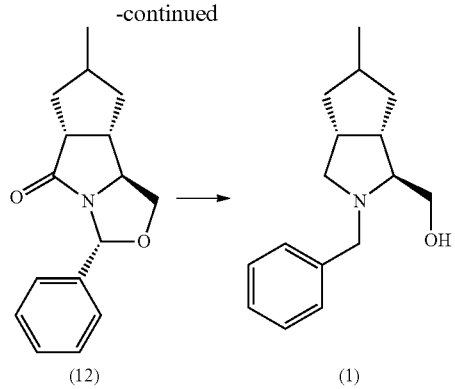

Alternatively, compounds of structure (1) are prepared from the known ketone of structure (13) (WO03/062265) as shown in scheme 6. Transformation of the ketone using well known alkyl Wittig reagents and subsequent reduction of the so formed double bond gives the intermediate (12), wherein $R^2$ represents hydrogen. Alternatively, reaction of the ketone with alkyl-zinc reagents as described in (Reetz M. T. et al *Angewandte Chemie* 1980, 92 (11), 931-933; J. Org. Chem. 1983, 48, 254-255; *Chemische Berichte* 1985, 118(3), 1050-1057) furnishes compounds of structure (12) wherein $R^1$ and $R^2$ represent $(C_{1-4})$alkyl. Compounds of structure (12) can be transformed into compounds of structure (1) as described before.

Scheme 6: Synthesis of compounds of structure (1)

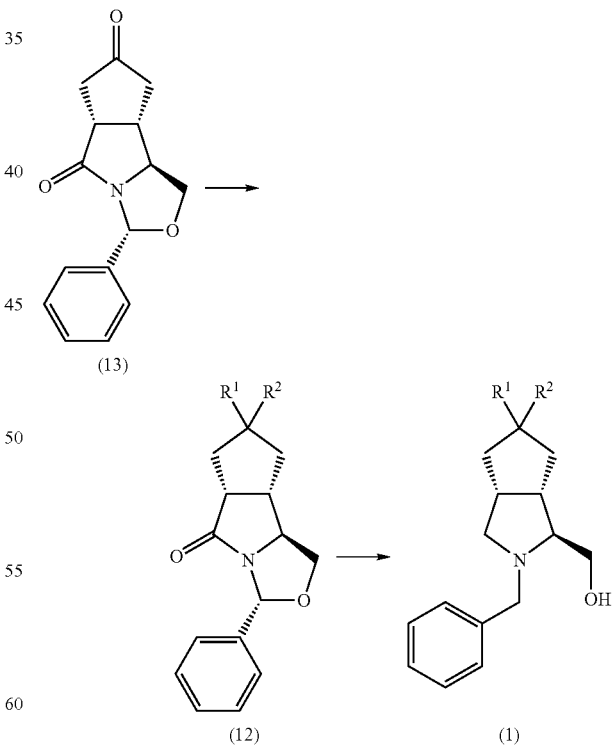

3-Aza-bicyclo[3.3.0]octane derivatives of formula (I), wherein $R^1$ and $R^2$ both represent fluorine are prepared as described in the literature (WO03/062265) or according to scheme 7.

Scheme 7: Synthesis of compounds of structure (I)

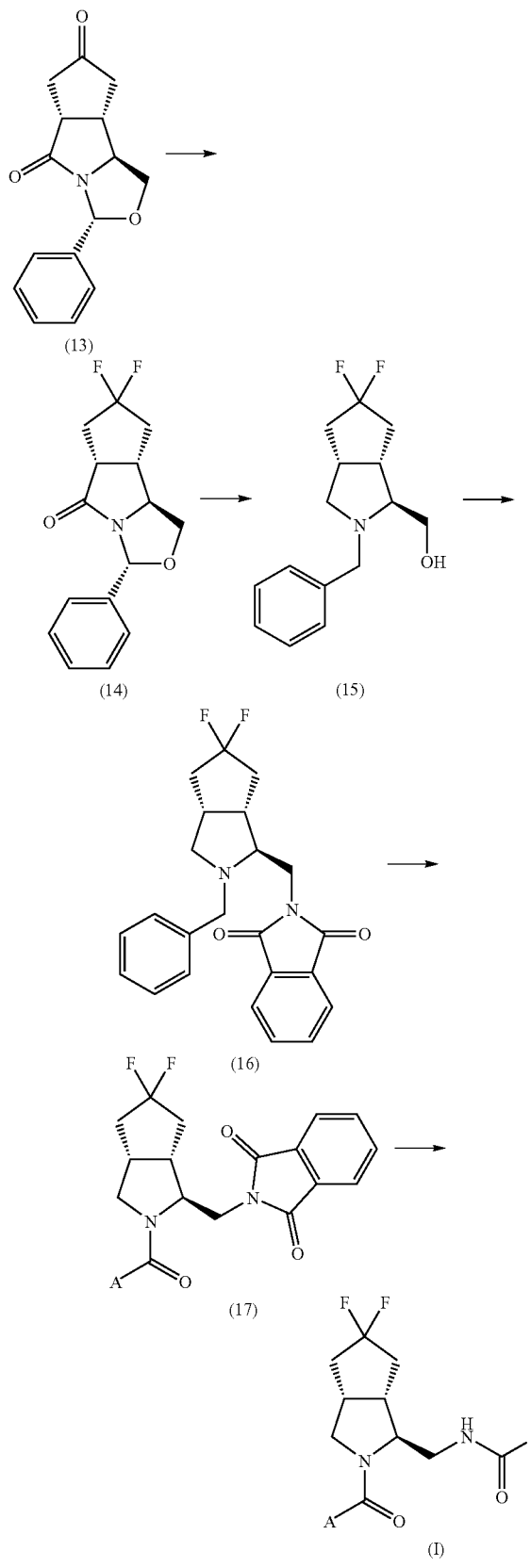

Fluorination of ketone (13) by reaction with DAST in a aprotic solvent such as DCM afforded intermediate (14). Reduction with lithium aluminium hydride in a aprotic solvent such as THF furnished the desired alcohol (15). Mitsunobu reaction with phthalimide in the presence of DEAD and triphenylphosphine in a aprotic solvent such as THF yielded the intermediate (16). Cleavage of the benzyl group by transfert hydrogenation with ammonium formate and Pd—C 10% in MeOH followed by coupling with a carboxylic acid A-COOH in the presence of a coupling reagent such as TBTU afforded intermediate (17). Cleavage of the phthalimide by reaction with hydrazine monohydrate in EtOH followed by coupling with a carboxylic acid $R^3$—COOH in the presence of a coupling reagent such as TBTU afforded the desired compounds of formula (I).

Preparation of Carboxylic Acids A-COOH

Acids of the formula A-COOH are commercially available or synthesized according to methods described below.

Carboxylic acid derivatives A-COOH wherein A represents a thiazole-4-yl derivative are commercially available or can be synthesised according to scheme 7.

Scheme 7: Synthesis of carboxylic acids A—COOH
wherein A represents a thiazole-4-yl derivative

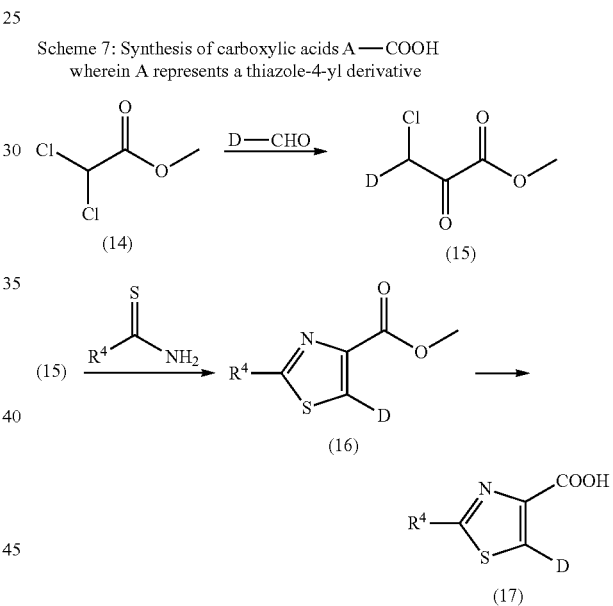

By reaction of methyl dichloroacetate (14) with an aldehyde of the formula D-CHO in the presence of a base such as KOtBu in an aprotic polar solvent such as THF at RT 3-chloro-2-oxo-propionic acid ester derivatives (15) are obtained. Compounds of structure (15) can be transformed by reaction with commercially available thioamides or thioureas $R^2$—C(S)—$NH_2$ at RT in solvents such as MeCN to provide thiazol-4-carboxylic acid ester derivatives (16). Saponification of the ester function using methods known in the art such as treatment with a base such as NaOH in a solvent such as MeOH provides the corresponding thiazol-4-carboxylic acid derivatives (17). Aldehydes of formula D-CHO are commercially available or well known in the art.

Carboxylic acid derivatives A-COOH wherein A represents a thiazole-5-yl derivative are commercially available or synthesised according to scheme 8.

Scheme 8: Synthesis of carboxylic acids A—COOH wherein A represents a thiazole-5-yl derivative

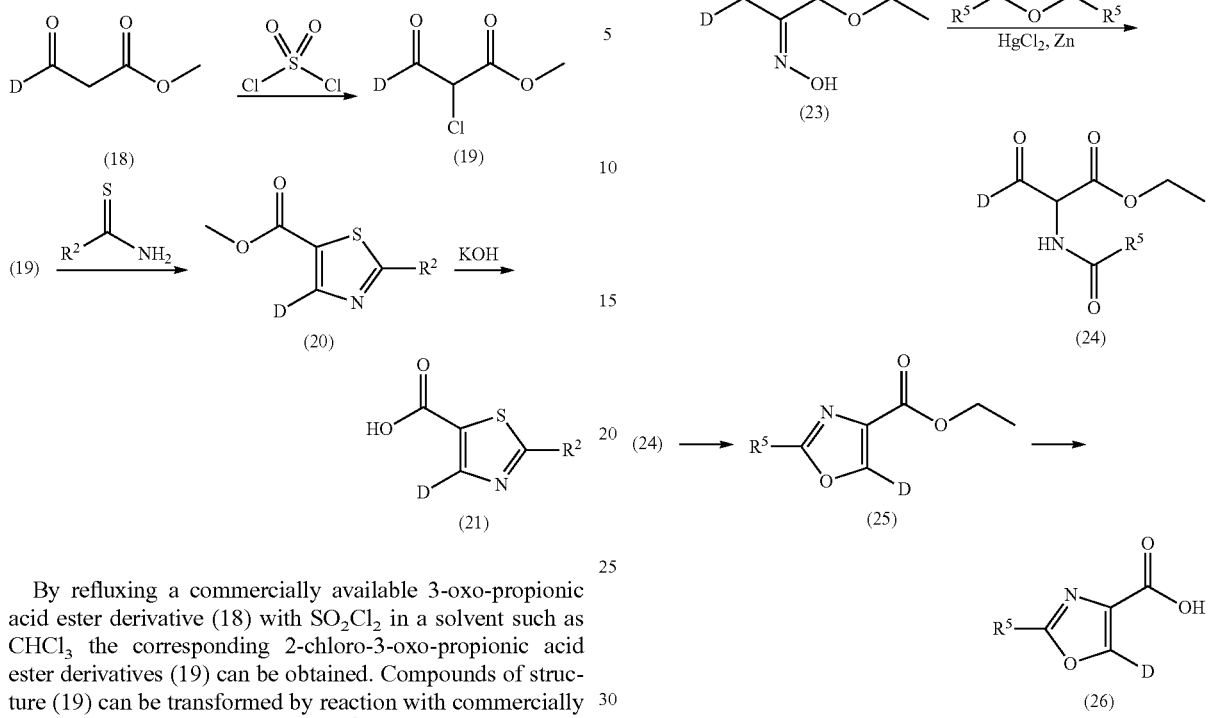

By refluxing a commercially available 3-oxo-propionic acid ester derivative (18) with SO$_2$Cl$_2$ in a solvent such as CHCl$_3$ the corresponding 2-chloro-3-oxo-propionic acid ester derivatives (19) can be obtained. Compounds of structure (19) can be transformed by reaction with commercially available thioamides or thioureas R$^2$—C(S)—NH$_2$ at reflux temperature in solvents such as THF in presence of a base such as NaHCO$_3$ to the corresponding thiazol-5-carboxylic acid ester derivatives (20). Saponification of the ester function using methods known in the art such as treatment with a base such as KOH in a solvent such as EtOH provides the corresponding thiazol-5-carboxylic acid derivatives (21).

Carboxylic acid derivatives A-COOH wherein A represents a oxazole-4-yl derivative which are commercially available or synthesised according to scheme 9.

By reaction of a commercially available 3-oxo-propionic acid ester derivative (22) with an aq. solution sodium nitrite in presence of an acid such as glacial acetic acid the corresponding oxime derivative (23) can be obtained. The 2-acetamido-3-oxo-propionic acid ester derivative (24) can be synthesized from compounds of structure (24) using a carboxylic acid anhydride such as acetic acid anhydride in presence of an acid such as glacial acetic acid and catalytic amounts of metal chlorides such as mercury chloride and zinc powder. Cyclization to the corresponding oxazole-4-carboxylic acid ester derivative (25) can be achieved under dehydrating conditions such as thionyl chloride in chloroform. Saponification of the ester function using methods known in the art such as treatment with a base such as NaOH in solvent mixtures such as EtOH/water provides the corresponding oxazole-4-carboxylic acid derivative (26).

Scheme 9: Synthesis of carboxylic acids A—COOH wherein A represents an oxazole-4-yl derivative

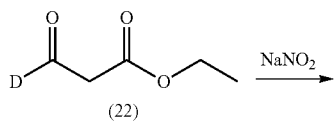

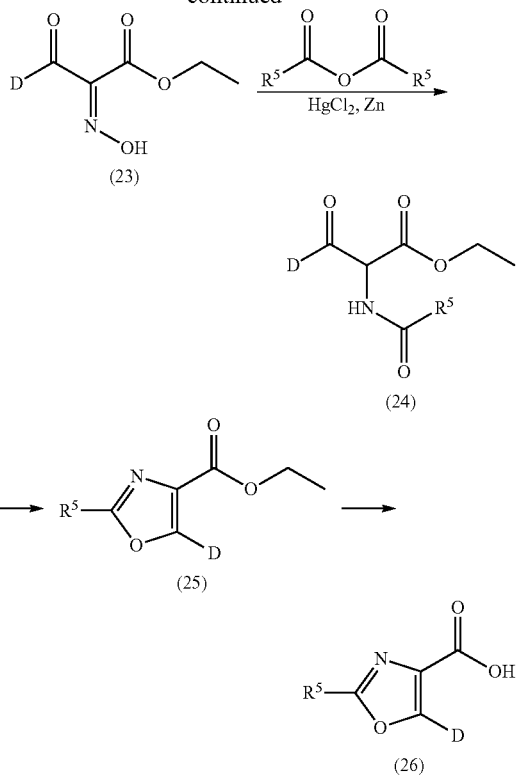

Carboxylic acid derivatives A-COOH wherein A represents a phenyl-2-yl derivative are commercially available or can be synthesised according to scheme 10.

Scheme 10: Synthesis of carboxylic acids A—COOH wherein A represents a phenyl-2-yl derivative

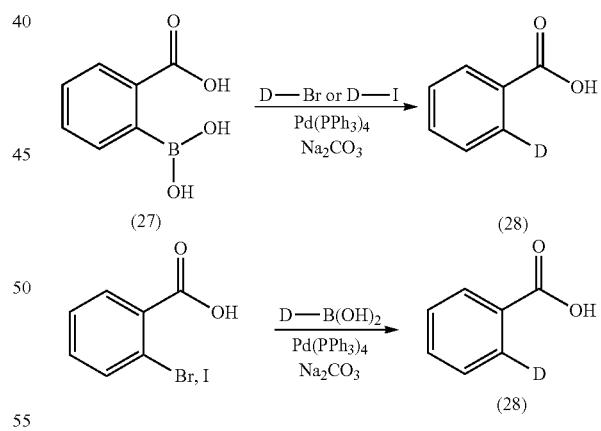

Reaction of commercially available (2-carboxyphenyl)-boronic acid derivatives (27) or esters thereof with commercially available aryl-bromides or aryl-iodides of formula D-Br or D-I in presence of a catalyst such as Pd(PPh$_3$)$_4$ and a base such as Na$_2$CO$_3$ under heating in a solvent such as toluene, dioxane, THF provides, after saponification, if needed, of the ester using well known methods, the corresponding phenyl-2-carboxylic acid derivatives (28). Alternatively, reaction of commercially available 2-bromo-, or 2-iodo-benzoic acid, or esters thereof, with commercially available boronic acid derivatives of formula D-B(OH)$_2$ using the conditions described before provides the corresponding phenyl-2-carboxylic acid derivatives (28).

Synthesis of Carboxylic Acids R³—COOH

Carboxylic acids of formula R³—COOH are commercially available or well known in the art (Lit. e.g. WO2001/96302; T. Eicher, S. Hauptmann "The chemistry of Heterocycles: Structure, Reactions, Syntheses, and Applications", 2nd Edition 2003, Wiley, ISBN 978-3-527-30720-3).

Carboxylic acid derivatives R³—COOH which represent an imidazo[2,1-b]thiazole-2-carboxylic acid or an imidazo[2,1-b]thiazole-5-carboxylic acid derivative are commercially available or can be synthesised according to scheme 11.

Pathway A: By reaction of 2-chloro-3-oxo-butyric acid methyl ester (29) with thiourea the amino-thiazole (30) can be obtained. Transformation to ester (31) can be accomplished with bromoacetaldehyde, which can be generated in-situ from bromoacetaldehyde diethylacetal under acidic conditions. After saponification with bases such as NaOH the desired acid (32) can be obtained.

Pathway B: By heating a compound of structure (33) with N,N-dimethylformamide dimethylacetal in a solvent such as toluene formamidine derivatives (34) can be obtained. They can be alkylated with ethyl bromoacetate yielding the respective thiazolium bromide (35), which can be cyclised with strong bases such as DBU to the ester (36). Saponification of the ester function using methods known in the art such as treatment with a base such as NaOH in a solvent such as EtOH/water provides the corresponding imidazo[2,1-b]thiazole-5-carboxylic acid derivatives (37). In scheme 11 preferably $R^a$ and $R^b$ independently represent hydrogen or methyl.

Scheme 11: Synthesis of carboxylic acids R³—COOH represent an imidazo[2,1-b]thiazole-2-carboxylic acid or an imidazo[2,1-b]thiazole-5-carboxylic acid derivative Pathway A

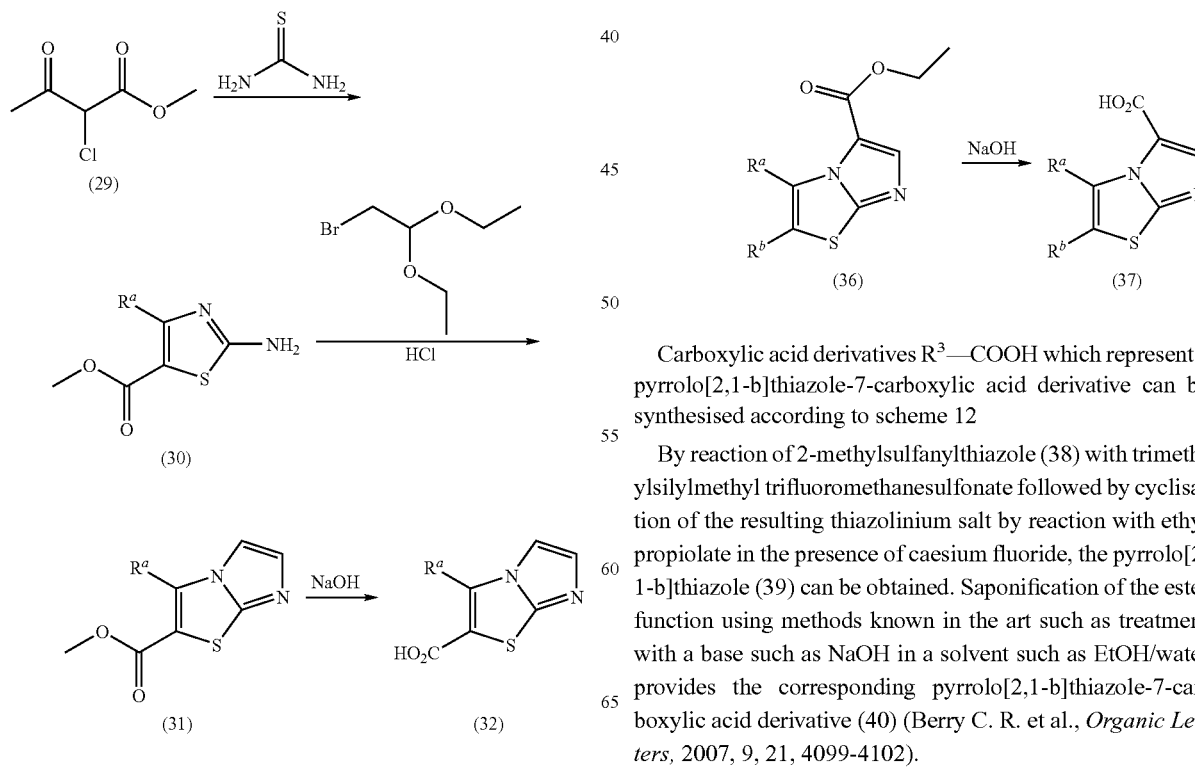

Pathway B

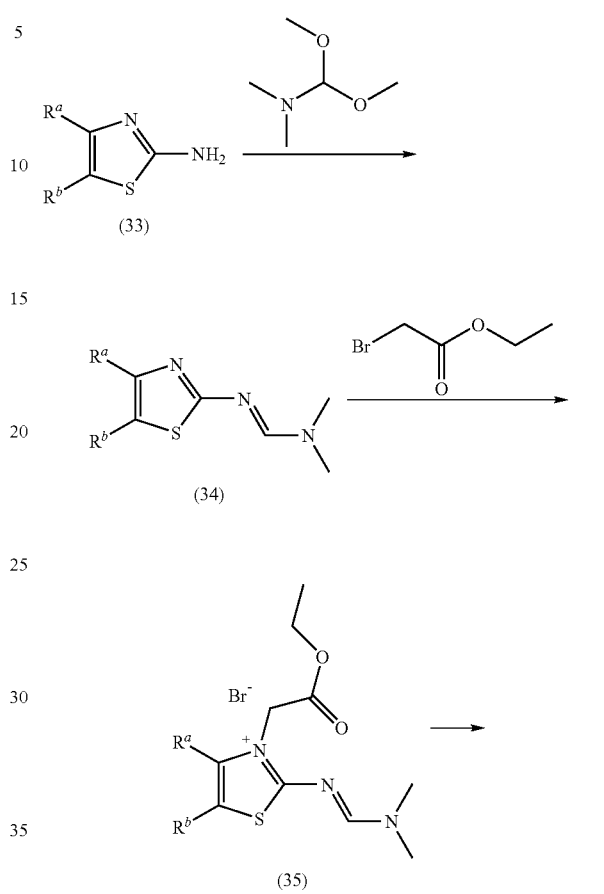

Carboxylic acid derivatives R³—COOH which represent a pyrrolo[2,1-b]thiazole-7-carboxylic acid derivative can be synthesised according to scheme 12

By reaction of 2-methylsulfanylthiazole (38) with trimethylsilylmethyl trifluoromethanesulfonate followed by cyclisation of the resulting thiazolinium salt by reaction with ethyl propiolate in the presence of caesium fluoride, the pyrrolo[2,1-b]thiazole (39) can be obtained. Saponification of the ester function using methods known in the art such as treatment with a base such as NaOH in a solvent such as EtOH/water provides the corresponding pyrrolo[2,1-b]thiazole-7-carboxylic acid derivative (40) (Berry C. R. et al., *Organic Letters*, 2007, 9, 21, 4099-4102).

Scheme 12: Synthesis of carboxylic acids $R^3$—COOH which represent a pyrrolo[2,1-b]thiazole-7-carboxylic acid derivative

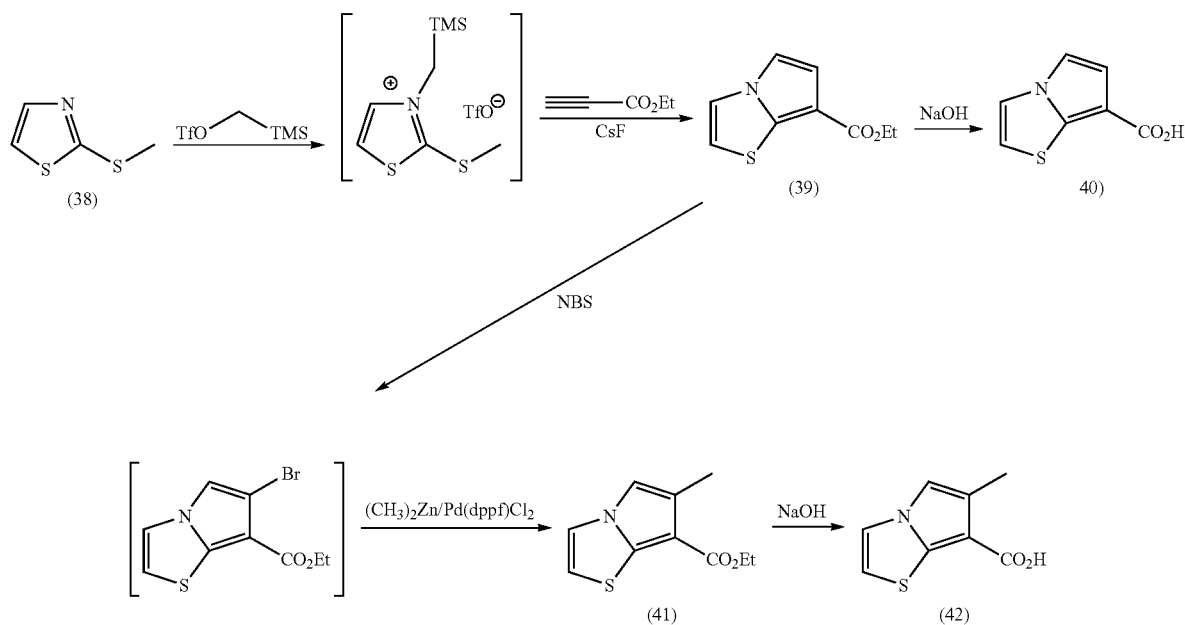

Bromination of (39) by reaction with NBS followed by methylation of the resulting crude ethyl 6-bromo-pyrrolo[2,1-b]thiazole-7-carboxylate by reaction with dimethylzinc in the presence of a palladium catalyst such as Pd(dppf)Cl$_2$ gave the ester (41). Saponification of the ester function using methods known in the art such as treatment with a base such as NaOH in a solvent such as EtOH/water provides the corresponding 6-methyl-pyrrolo[2,1-b]thiazole-7-carboxylic acid derivative (42).

Carboxylic acid derivatives $R^3$—COOH which represent a benzothiazole-7-carboxylic acid derivative can be synthesised according to the literature according to scheme 13.

Scheme 13: Synthesis of carboxylic acids $R^3$—COOH which represent a benzothiazole-7-carboxylic acid derivative

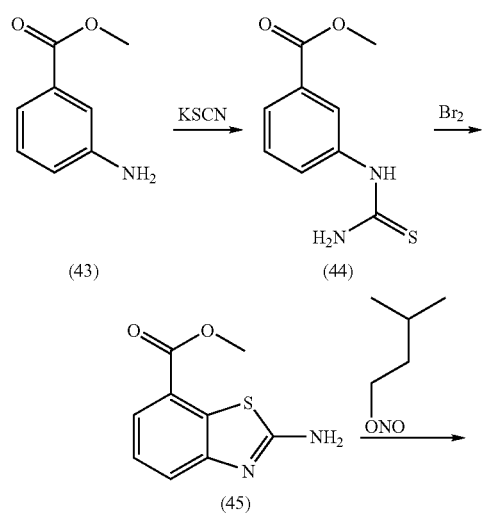

-continued

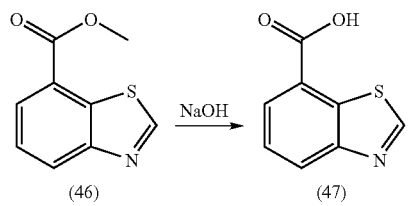

By reaction of methyl 3-aminobenzoate (43) with potassium thiocyanate in the presence of sulfuric acid and crown-ether 18-C-6, the thiourea (44) can be obtained. Cyclisation by reaction with bromine in acetic acid provides the 2-aminobenzothiazole derivative (45). Cleavage of the amino group by reaction with isoamyl nitrite furnishes the ester (46) (WO2005/092890). Saponification of the ester function using methods known in the art such as treatment with a base such as NaOH in a solvent such as MeOH/water provides the corresponding benzothiazole-7-carboxylic acid derivative (47).

Carboxylic acid derivatives $R^3$—COOH which represent a benzofuran-4-carboxylic acid derivative can be synthesised according to the literature according to schemes 14 and 15.

Scheme 14: Synthesis of carboxylic acids R³—COOH which represent a 3-methylbenzofuran and a 2,3-dimethylbenzofuran-4-carboxylic acid derivatives

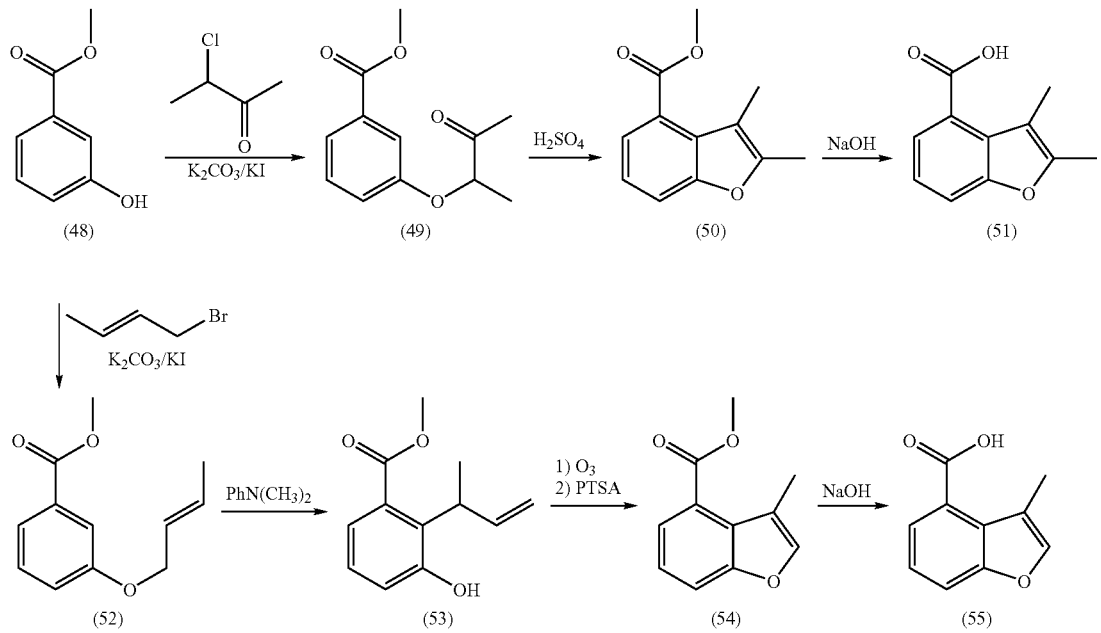

By reaction of methyl 3-hydroxybenzoate (48) with 3-chloro-2-butanone, the ester (49) can be obtained. Cyclisation with sulfuric acid provides the 2,3-dimethylbenzofuran derivative (50) (Kawase Y. et al, *Bulletin of the Chemical Sociaty of Japan*, 1967, 40, 5, 1224-1231. Saponification of the ester function using methods known in the art such as treatment with a base such as NaOH in a solvent such as MeOH/water provides the corresponding 2,3-dimethylbenzofuran-4-carboxylic acid derivative (51). On the other hand, reaction of methyl 3-hydroxybenzoate (58) with crotyl bromide furnishes the ester (52) which after reaction in N,N-dimethylaniline provides the ester (53). Ozonolysis followed by reaction with PTSA gives the 3-methylbenzofuran derivative (54) (Mohamadi F. et al, *Journal of Medicinal Chemistry*, 1994, 37, 232-239 and EP58906). Saponification of the ester function using methods known in the art such as treatment with a base such as NaOH in a solvent such as MeOH/water provides the corresponding 3-methylbenzofuran-4-carboxylic acid derivative (55).

Scheme 15: Synthesis of carboxylic acids R¹—COOH which represent a 2-methylbenzofuran-4-carboxylic acid derivative

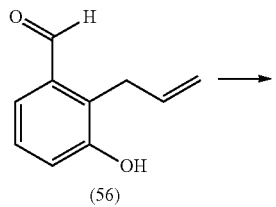

-continued

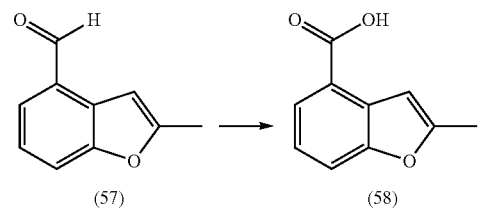

By cyclisation of 2-allyl-3-hydroxybenzaldehyde (56) with a palladium catalyst such as bis(acetonitrile)dichloropalladium in the presence of 1,4-benzoquinone and LiCl, the 2-methylbenzofuran carbaldehyde (57) can be obtained (Danheiser R. L. et al, *Organic Letters*, 2005, 7, 18, 3905-3908). Oxidation of the aldehyde function with sodium chlorite in the presence of a scavenger such as 2-methyl-2-butene furnishes the corresponding 2-methylbenzofuran-4-carboxylic acid (58).

Whenever the compounds of formula (I) are obtained in the form of mixtures of enantiomers, the enantiomers can be separated using methods known to the one skilled in the art: e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm) or AD-H (5 µm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min.

EXPERIMENTAL SECTION

Examples

| Abbreviations (as used herein): | |
|---|---|
| aq. | aqueous |
| anh. | anhydrous |
| Boc | tert.-butoxycarbonyl |
| Boc$_2$O | di-tert.-butyl dicarbonate |
| BSA | bovine serum albumine |
| CHO | chinese hamster ovary |
| DAST | diethylaminosulfur trifluoride |
| DBU | 1,8-diazabicyclo[5.4.0]undec-7-ene |
| DCM | dichloromethane |
| DEAD | diethyl azodicarboxylate |
| dppf | diphenylphosphinoferrocene |
| DIPEA | diisopropylethylamine |
| DMF | N,N-dimethylformamide |
| DMSO | dimethylsulfoxide |
| dppf | 1,1'-bis(diphenylphosphanyl)ferrocene |
| EA | ethyl acetate |
| eq | equivalent(s) |
| ES | electron spray |
| Et | ethyl |
| ether | diethylether |
| EtOH | ethanol |
| FC | flash chromatography |
| FCS | foatal calf serum |
| FLIPR | fluorescent imaging plate reader |
| h | hour(s) |
| HATU | (O-(7-azabenzotriazol-1-yl)-1,1,3,3-tetramethyl-uronium hexafluorphoshate |
| HBSS | Hank's balanced salt solution |
| HEPES | 4-(2-hydroxyethyl)-piperazine-1-ethanesulfonic acid |
| HPLC | high performance liquid chromatography |
| KOtBu | potassium tert. butoxide |
| LAH | lithium aluminum hydride |
| LC | liquid chromatography |
| M | molar(ity) |
| Me | methyl |
| MeCN | acetonitrile |
| MeOH | methanol |
| min | minute(s) |
| M.S. | molecular sieve |
| MS | mass spectroscopy |
| NaBH(OAc)$_3$ | sodium triacetoxyborohydride |
| NBS | N-bromosuccinimide |
| org. | organic |
| Ph | phenyl |
| prep. | Preparative |
| PTSA | p-toluenesulfonic acid |
| PyBOP | (benzotriazole-1-yloxy)-tripyrrolidinophosphonium-hexafluorophosphate |
| RT | room temperature |
| sat. | saturated |
| sec. | secundary |
| t$_R$ | retention time |
| TBTU | O-benzotriazol-1-yl-N,N,N',N'-tetramethyluronium tetrafluoroborate |
| tert. | tertiary |
| TFA | trifluoroacetic acid |
| Tf | trifluoromethanesulfonyl |
| THF | tetrahydrofuran |
| TMS | trimethylsilyl |

I-Chemistry

All temperatures are stated in ° C. Compounds are characterized by $^1$H-NMR (300 MHz: Varian Oxford or 400 MHz: Bruker Avance); chemical shifts are given in ppm relative to the solvent used; multiplicities: s=singlet, d=doublet, t=triplet; q=quartett, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, using the following conditions: acidic: eluent A: MeCN, eluent B: TFA in water (0.4 mL/L), 5% to 95% CH$_3$CN), t$_R$ is given in min; by TLC (TLC-plates from Merck, Silica gel 60 F$_{254}$); or by melting point. Compounds are purified by column chromatography (FC) on silica gel or by preparative HPLC (column: X-terra RP18, 50×19 mm, 5 µm, gradient: 10-95% MeCN in water containing 0.5% of formic acid). Racemates can be separated into their enantiomers by preparative HPLC.

The following examples illustrate the preparation of pharmacologically active compounds of the invention but do not at all limit the scope thereof.

Preparation of Precursors and Intermediates:

A.1 Synthesis of thiazole-carboxylic acid derivatives

A.1.1 Synthesis of 3-chloro-2-oxo-propionic ester derivatives (general procedure)

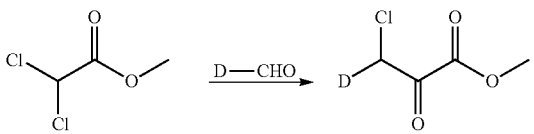

A solution of the respective aldehyde D-CHO (338 mmol, 1.0 eq) and methyl dichloroacetate (338 mmol, 1.0 eq) in THF (100 mL) is added dropwise to a cold (−60° C.) suspension of KOtBu (335 mmol, 1.0 eq) in THF (420 mL). After 4 h the mixture is allowed to reach RT, stirred over night and concentrated in vacuo. DCM and ice-cold water are added, the layers are separated and the aqueous layer is extracted twice with DCM. The combined org. layers are washed with ice-cold water and brine, dried over MgSO$_4$ and concentrated in vacuo to give the corresponding 3-chloro-2-oxo-propionic acid methyl ester derivative which is used without further purification.

3-Chloro-2-oxo-3-phenyl-propionic acid methyl ester prepared by reaction of benzaldehyde with methyl dichloroacetate.

3-Chloro-2-oxo-3-m-tolyl-propionic acid methyl ester prepared by reaction of 3-methyl-benzaldehyde with methyl dichloroacetate.

3-Chloro-2-oxo-3-p-tolyl-propionic acid methyl ester prepared by reaction of 4-methyl-benzaldehyde with methyl dichloroacetate.

3-Chloro-3-(4-ethyl-phenyl)-2-oxo-propionic acid methyl ester prepared by reaction of 4-ethyl-benzaldehyde with methyl dichloroacetate.

3-Chloro-3-(3-fluoro-phenyl)-2-oxo-propionic acid methyl ester prepared by reaction of 3-fluoro-benzaldehyde with methyl dichloroacetate.

3-Chloro-3-(4-fluoro-phenyl)-2-oxo-propionic acid methyl ester prepared by reaction of 4-fluoro-benzaldehyde with methyl dichloroacetate.

3-Chloro-2-oxo-3-(3-trifluoromethyl-phenyl)-propionic acid methyl ester prepared by reaction of 3-trifluoromethyl-benzaldehyde with methyl dichloro-acetate.

3-Chloro-2-oxo-3-(4-trifluoromethyl-phenyl)-propionic acid methyl ester prepared by reaction of 4-trifluoromethyl-benzaldehyde with methyl dichloro-acetate.

3-Chloro-3-(3-chloro-phenyl)-2-oxo-propionic acid methyl ester prepared by reaction of 3-chloro-benzaldehyde with methyl dichloro-acetate.

3-Chloro-3-(4-chloro-phenyl)-2-oxo-propionic acid methyl ester prepared by reaction of 4-chloro-benzaldehyde with methyl dichloro-acetate.

3-Chloro-3-(3-methoxy-phenyl)-2-oxo-propionic acid methyl ester prepared by reaction of 3-methoxy-benzaldehyde with methyl dichloro-acetate.

3-Chloro-3-(4-methoxy-phenyl)-2-oxo-propionic acid methyl ester prepared by reaction of 4-methoxy-benzaldehyde with methyl dichloroacetate.

3-Chloro-3-(3,4-dimethyl-phenyl)-2-oxo-propionic acid methyl ester prepared by reaction of 3,4-dimethyl-benzaldehyde with methyl dichloro-acetate.

3-Chloro-3-(3,4-difluoro-phenyl)-2-oxo-propionic acid methyl ester prepared by reaction of 3,4-difluoro-benzaldehyde with methyl dichloroacetate.

A.1.2 Synthesis of 2-methyl-thiazole-4-carboxylic acid methyl ester derivatives (general procedure)

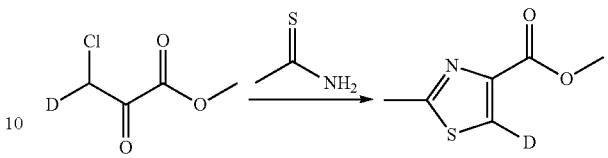

A solution of thioacetamide (132 mmol, 1.0 eq) in MeCN (250 mL) is added to a mixture of the respective 3-chloro-2-oxo-propionic acid methyl ester derivative (132 mmol, 1.0 eq) and molecular sieves (4 Å, 12 g) in MeCN (60 mL). After stirring for 5 h the mixture is cooled in an ice-bath and the obtained precipitate is filtered off. The residue is washed with cold MeCN, dried, dissolved in MeOH (280 mL) and stirred at 50° C. for 6 h. The solvents are removed in vacuo to give the corresponding 2-methyl-thiazole-4-carboxylic acid methyl ester derivatives.

5-Phenyl-2-methyl-thiazole-4-carboxylic acid methyl ester prepared by reaction of 3-chloro-3-phenyl-2-oxo-propionic acid methyl ester with thioacetamide. LC-MS: $t_R$=0.88 min; $[M+H]^+$=234.23.

2-Methyl-5-m-tolyl-thiazole-4-carboxylic acid methyl ester prepared by reaction of 3-chloro-2-oxo-3-m-tolyl-propionic acid methyl ester with thioacetamide. LC-MS: $t_R$=0.94 min; $[M+H]^+$=248.0.

2-Methyl-5-p-tolyl-thiazole-4-carboxylic acid methyl ester prepared by reaction of 3-chloro-2-oxo-3-p-tolyl-propionic acid methyl ester with thioacetamide. LC-MS: $t_R$=0.93 min; $[M+H]^+$=248.02.

5-(4-Ethyl-phenyl)-2-methyl-thiazole-4-carboxylic acid methyl ester prepared by reaction of 3-chloro-3-(4-ethyl-phenyl)-2-oxo-propionic acid methyl ester with thioacetamide. LC-MS: $t_R$=0.98 min; $[M+H]^+$=262.1.

5-(3-Fluoro-phenyl)-2-methyl-thiazole-4-carboxylic acid methyl ester prepared by reaction of 3-chloro-3-(3-fluoro-phenyl)-2-oxo-propionic acid methyl ester with thioacetamide. LC-MS: $t_R$=0.91 min; $[M+H]^+$=252.1.

5-(4-Fluoro-phenyl)-2-methyl-thiazole-4-carboxylic acid methyl ester prepared by reaction of 3-chloro-3-(4-fluoro-phenyl)-2-oxo-propionic acid methyl ester with thioacetamide. $^1$H-NMR (CDCl$_3$): δ=2.75 (s, 3H); 3.84 (s, 3H); 7.10 (m, 2H); 7.47 (m, 2H).

2-Methyl-5-(3-trifluoromethyl-phenyl)-thiazole-4-carboxylic acid methyl ester prepared by reaction of 3-chloro-3-(3-trifluoromethyl-phenyl)-2-oxo-propionic acid methyl ester with thioacetamide. LC-MS: $t_R$=0.99 min; $[M+H]^+$=301.99.

2-Methyl-5-(4-trifluoromethyl-phenyl)-thiazole-4-carboxylic acid methyl ester prepared by reaction of 3-chloro-3-(4-trifluoromethyl-phenyl)-2-oxo-propionic acid methyl ester with thioacetamide. LC-MS: $t_R$=0.99 min; $[M+H]^+$=301.99.

5-(3-Chloro-phenyl)-2-methyl-thiazole-4-carboxylic acid methyl ester prepared by reaction of 3-chloro-3-(3-chloro-phenyl)-2-oxo-propionic acid methyl ester with thioacetamide. LC-MS: $t_R$=0.95 min; $[M+H]^+$=268.0.

5-(4-Chloro-phenyl)-2-methyl-thiazole-4-carboxylic acid methyl ester prepared by reaction of 3-chloro-3-(4-chloro-phenyl)-2-oxo-propionic acid methyl ester with thioacetamide. LC-MS: $t_R$=0.94 min; $[M+H]^+$=267

5-(3-Methoxy-phenyl)-2-methyl-thiazole-4-carboxylic acid methyl ester prepared by reaction of 3-chloro-3-(3-methoxy-phenyl)-2-oxo-propionic acid methyl ester with thioacetamide. LC-MS: $t_R$=0.90 min; $[M+H]^+$=263.87.

5-(4-Methoxy-phenyl)-2-methyl-thiazole-4-carboxylic acid methyl ester prepared by reaction of 3-chloro-3-(4-methoxy-phenyl)-2-oxo-propionic acid methyl ester with thioacetamide. LC-MS: $t_R$=0.90 min; $[M+H]^+$=263.93.

2-Methyl-5-(3,4-dimethyl-phenyl)-thiazole-4-carboxylic acid methyl ester prepared by reaction of 3-chloro-3-(3,4-dimethyl-phenyl)-2-oxo-propionic acid methyl ester with thioacetamide. LC-MS: $t_R$=0.96 min; $[M+H]^+$=262.34.

2-Methyl-5-(3,4-difluoro-phenyl)-thiazole-4-carboxylic acid methyl ester prepared by reaction of 3-chloro-3-(3,4-difluoro-phenyl)-2-oxo-propionic acid methyl ester with thioacetamide. LC-MS: $t_R$=0.92 min; $[M+H]^+$=270.29.

A.1.3 Synthesis of 2-amino-thiazole-4-carboxylic acid methyl ester derivatives (general procedure)

A solution of the respective 3-chloro-2-oxo-propionic acid methyl ester derivative (22.1 mmol, 1.0 eq) in acetone (25 mL) is added to a suspension of thiourea (22.1 mmol, 1.0 eq) in acetone (45 mL). The mixture is heated to 57° C. (bath temperature), stirred for 24 h and concentrated to half of the volume. The obtained suspension is filtered and the residue is washed with acetone. After drying the desired amino-thiazole derivative is obtained as a solid.

2-Amino-5-m-tolyl-thiazole-4-carboxylic acid methyl ester prepared by reaction of 3-chloro-2-oxo-3-m-tolyl-propionic acid methyl ester with thiourea. LC-MS: $t_R$=0.78 min; $[M+H]^+$=249.0.

2-Amino-5-(3-fluoro-phenyl)-thiazole-4-carboxylic acid methyl ester prepared by reaction of 3-chloro-3-(3-fluoro-phenyl)-2-oxo-propionic acid methyl ester with thiourea. LC-MS: $t_R$=0.78 min; $[M+H]^+$=252.9.

2-Amino-5-(4-fluoro-phenyl)-thiazole-4-carboxylic acid methyl ester prepared by reaction of 3-chloro-3-(4-fluoro-phenyl)-2-oxo-propionic acid methyl ester with thiourea. LC-MS: $t_R$=0.75 min; $[M+H]^+$=253.

2-Amino-5-phenyl-thiazole-4-carboxylic acid methyl ester prepared by reaction of 3-chloro-3-phenyl-2-oxo-propionic acid methyl ester with thiourea. LC-MS: $t_R$=0.77 min; $[M+H]^+$=235.

A.1.4 Synthesis of thiazole-4-carboxylic acid derivatives (general procedure)

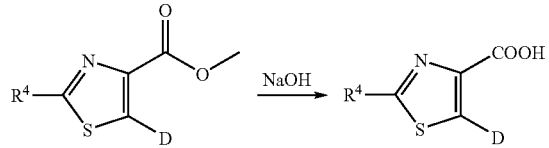

A solution of the respective thiazole-4-carboxylic acid methyl ester (96.2 mmol) in a mixture of THF (150 mL) and MeOH (50 mL) is treated with 1M aq. NaOH (192 mL). After stirring for 3 h a white suspension is formed and the org. volatiles are removed in vacuo. The remaining mixture is diluted with water (100 mL), cooled in an ice-bath and acidified (pH=3-4) by addition of 1M aq. HCl. The suspension is filtered and the residue is washed with cold water. After drying the corresponding thiazole-4-carboxylic acid derivative is obtained.

2-Methyl-5-phenyl-thiazole-4-carboxylic acid prepared by saponification of 2-methyl-5-phenyl-thiazole-4-carboxylic acid methyl ester. LC-MS: $t_R$=0.78 min; $[M+H]^+$=220.01.

2-Methyl-5-m-tolyl-thiazole-4-carboxylic acid prepared by saponification of 2-methyl-5-m-tolyl-thiazole-4-carboxylic acid methyl ester. LC-MS: $t_R$=0.83 min; $[M+H]^+$=234.0.

2-Methyl-5-p-tolyl-thiazole-4-carboxylic acid prepared by saponification of 2-methyl-5-p-tolyl-thiazole-4-carboxylic acid methyl ester. LC-MS: $t_R$=0.83 min; [M+H]$^+$=234.0.

5-(4-Ethyl-phenyl)-2-methyl-thiazole-4-carboxylic acid prepared by saponification of 5-(4-ethyl-phenyl)-2-methyl-thiazole-4-carboxylic acid methyl ester. LC-MS: $t_R$=0.88 min; [M+H]$^+$=248.0.

5-(3-Fluoro-phenyl)-2-methyl-thiazole-4-carboxylic acid prepared by saponification of 5-(3-fluoro-phenyl)-2-methyl-thiazole-4-carboxylic acid methyl ester. LC-MS: $t_R$=0.82 min; [M+H]$^+$=238.1.

5-(4-Fluoro-phenyl)-2-methyl-thiazole-4-carboxylic acid prepared by saponification of 5-(4-fluoro-phenyl)-2-methyl-thiazole-4-carboxylic acid methyl ester. $^1$H-NMR (DMSO-d$_6$): δ=2.67 (s, 3H); 7.27 (m, 2H); 7.53 (m, 2H); 12.89 (br.s, 1H).

5-(3-Chloro-phenyl)-2-methyl-thiazole-4-carboxylic acid prepared by saponification of 5-(3-chloro-phenyl)-2-methyl-thiazole-4-carboxylic acid methyl ester. LC-MS: $t_R$=0.84 min; [M+H]$^+$=254.0.

5-(4-Chloro-phenyl)-2-methyl-thiazole-4-carboxylic acid prepared by saponification of 5-(4-chloro-phenyl)-2-methyl-thiazole-4-carboxylic acid methyl ester. LC-MS: $t_R$=0.85 min; [M+H]$^+$=253.

2-Methyl-5-(3-trifluoromethyl-phenyl)-thiazole-4-carboxylic acid prepared by saponification of 2-methyl-5-(3-trifluoromethyl-phenyl)-thiazole-4-carboxylic acid methyl ester. LC-MS: $t_R$=0.88 min; [M+H]$^+$=287.99.

2-Methyl-5-(4-trifluoromethyl-phenyl)-thiazole-4-carboxylic acid prepared by saponification of 2-methyl-5-(4-trifluoromethyl-phenyl)-thiazole-4-carboxylic acid methyl ester. LC-MS: $t_R$=0.90 min; [M+H]$^+$=287.99.

2-Methyl-5-(3-methoxy-phenyl)-thiazole-4-carboxylic acid prepared by saponification of 2-methyl-5-(3-methoxy-phenyl)thiazole-4-carboxylic acid methyl ester. LC-MS: $t_R$=0.80 min; [M+H]$^+$=250.04.

2-Methyl-5-(4-methoxy-phenyl)-thiazole-4-carboxylic acid prepared by saponification of 2-methyl-5-(4-methoxy-phenyl)thiazole-4-carboxylic acid methyl ester. LC-MS: $t_R$=0.80 min; [M+H]$^+$=250.04.

2-Methyl-5-(3,4-dimethyl-phenyl)-thiazole-4-carboxylic acid prepared by saponification of 2-methyl-5-(3,4-dimethyl-phenyl)thiazole-4-carboxylic acid methyl ester. LC-MS: $t_R$=0.97 min; [M+H]$^+$=382.38.

2-Methyl-5-(3,4-difluoro-phenyl)-thiazole-4-carboxylic acid prepared by saponification of 2-methyl-5-(3,4-difluoro-phenyl)-thiazole-4-carboxylic acid methyl ester. LC-MS: $t_R$=0.82 min; [M+H]$^+$=256.25.

2-Amino-5-m-tolyl-thiazole-4-carboxylic acid prepared by saponification of 2-amino-5-m-tolyl-thiazole-4-carboxylic acid methyl ester. LC-MS: $t_R$=0.65 min; [M+H]$^+$=235.0.

2-Amino-5-(3-fluoro-phenyl)-thiazole-4-carboxylic acid prepared by saponification of 2-amino-5-(3-fluoro-phenyl)-thiazole-4-carboxylic acid methyl ester. LC-MS: $t_R$=0.62 min; [M+H]$^+$=239.1.

2-Amino-5-(4-fluoro-phenyl)-thiazole-4-carboxylic acid prepared by saponification of 2-amino-5-(4-fluoro-phenyl)-thiazole-4-carboxylic acid methyl ester. LC-MS: $t_R$=0.61 min; [M+H]$^+$=239.

2-Amino-5-phenyl-thiazole-4-carboxylic acid prepared by saponification of 2-amino-5-phenyl-thiazole-4-carboxylic acid methyl ester. LC-MS: $t_R$=0.63 min; [M+H]$^+$=221.

A.2 Synthesis of (1S,2S,5R)-2-aminomethyl-3-aza-bicyclo[3.3.0]-octane-3-carboxylic acid tert.-butyl ester

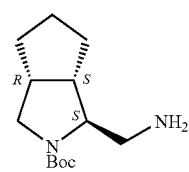

A.2.1 Synthesis of (1S,2S,5R)-2-hydroxymethyl-3-aza-bicyclo[3.3.0]-octane-3-carboxylic acid tert.-butyl ester A mixture of (1S,2S,5R)-3-benzyl-2-hydroxymethyl-3-aza-bicyclo[3.3.0]-octane (synthesized according to WO2003/062265) (350 mg), Pd—C (50% H₂O) (300 mg), Boc₂O (494 mg, 1.5 eq) in EA (14 mL) was stirred under hydrogen (1 bar) for 16 h. After filtration through celite and removal of the solvents the title compound was obtained as a yellow oil.

¹H-NMR (CDCl₃): δ=1.45 (s, 9H); 1.55-1.85 (m, 5H); 2.15 (m, 1H); 2.55 (m, 1H); 3.25-3.75 (m, 5H); 4.6 (m, 1H).

A.2.2 Synthesis of (1S,2S,5R)-2-formyl-3-aza-bicyclo[3.3.0]-octane-3-carboxylic acid tert.-butyl ester To a cold (−60° C.) solution of oxalyl chloride (0.14 mL, 1.2 eq) in dry DCM (3.7 mL) was added dropwise a solution of DMSO (0.215 mL, 2.2 eq) in dry DCM (2.9 mL) within 4 min. After 10 min, was added dropwise (1S,2S,5R)-2-hydroxymethyl-3-aza-bicyclo[3.3.0]-octane-3-carboxylic acid tert.-butyl ester (330 mg) in dry DCM (1.7 mL) during 5 min. After 2 min a white suspension was formed. Stirring was continued 30 min at −55° C., then DIPEA (1.17 mL, 5 eq) (which was dried over 3A M.S.) was added during 3-4 min. The reaction mixture was allowed to come to RT, diluted with water and extracted with DCM. The combined org. extracts were washed with citric acid (5%), brine, dried over anh. MgSO₄, filtered and evaporated to yield the title compound as an oil which was used for the next step without further purification.

¹H-NMR (CDCl₃): δ=1.45-1.95 (m, 15H); 2.65 (s, 2H); 3.25-3.55 (m, 3H); 9.45 (s, 1H).

A.2.3 Synthesis of (1S,2S,5R)-2-(benzylamino-methyl)-3-aza-bicyclo[3.3.0]-octane-3-carboxylic acid tert.-butyl ester Benzylamine (0.263 mL, 1.75 eq) was added to a solution of (1S,2S,5R)-2-formyl-3-aza-bicyclo[3.3.0]-octane-3-carboxylic acid tert.-butyl ester (330 mg, 1 eq) in chloroform (10 mL). After 15 min the mixture was treated with NaBH(OAc)₃ (292.25 mg, 1 eq), stirred for 2 h and poured into a sat. aq NaHCO₃ solution. The layers were separated and the aqueous layer was extracted twice with chloroform. The combined org. extracts were washed with sat. NaHCO₃ solution, dried over anh. MgSO₄, filtered and concentrated in vacuo to give a crude yellow oil. FC (EA/n-heptane: 3/7 to 7/3) gave the title compound as a colourless oil LC-MS: t_R=0.86 min; [M+H]⁺=331.

A.2.4 Synthesis of (1S,2S,5R)-2-aminomethyl-3-aza-bicyclo[3.3.0]-octane-3-carboxylic acid tert.-butyl ester A solution of (1S,2S,5R)-2-(benzylamino-methyl)-3-aza-bicyclo[3.3.0]-octane-3-carboxylic acid tert.-butyl ester (354 mg) in EtOH (17 mL) was treated with Pd/C 10% (141 mg) and stirred under hydrogen (1 bar) for 16 h. After filtration through celite and removal of the solvents the title compound was obtained as an oil which was used without further purification.

¹H-NMR (CDCl₃): δ=1.25-1.95 (m, 13H); 2.35-2.85 (m, 5H); 3.25-3.65 (m, 4H).

A.3 Synthesis of (1S,2S,5R)-2-aminomethyl-7-methyl-3-aza-bicyclo[3.3.0]-octane-3-carboxylic acid tert.-butyl ester

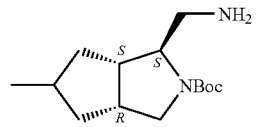

A.3.1 Synthesis of (1R,3aS,3bS,6aR)-5-methyl-1-phenyl-hexahydro-2-oxa-7a-aza-cyclopenta[a]pentalen-7-one

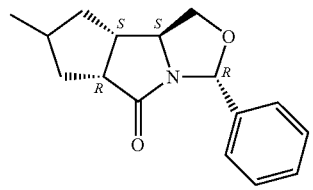

A solution of (1R,3aS,3bS,6aR)-5-methyl-1-phenyl-3a,3b,6,6a-tetrahydro-3H-2-oxa-7a-aza-cyclopenta[a]pentalen-7-one (Jao E. et al Tetrahedron Letters, 2003, 44, 5033-5035) (2.34 g) in EtOH (23 mL) was treated with Pd/C 10% (456 mg) and stirred under hydrogen (1 bar) for 1.5 h. After filtration through celite and removal of the solvents the title compound was obtained as an oil, which was used without further purification.

¹H-NMR (CDCl₃): δ=1.05-1.35 (m, 5H); 2.05-2.75 (m, 4H); 3.15-3.85 (m, 3H); 4.35 (s, 1H); 6.45 (s, 1H); 7.3-7.5 (m, 5H).

A.3.2 Synthesis of (1S,2S,5R)-3-benzyl-2-hydroxymethyl-7-methyl-3-aza-bicyclo[3.3.0]-octane To a cold (0° C.) solution of (1R,3aS,3bS,6aR)-5-methyl-1-phenyl-hexahydro-2-oxa-7a-aza-cyclopenta[a]pentalen-7-one (470 mg) in anh. THF (7 mL) was added LAH (160 mg, 2.3 eq) in small portion. The mixture then refluxed for 6 h before cooled to 0° C. To the reaction mixture were carefully added water (0.3 mL), aqueous NaOH solution (15%) (0.9 mL) and water (0.3 mL). The resulting solid was removed by filtration and the filtrate was concentrated in to yield a crude oil. FC (DCM/MeOH: 97/3 to 93/7) gave the title compound as a colourless oil.

LC-MS: t_R=0.69 min; [M+H]⁺=246.

A.3.3 Synthesis of (1S,2S,5R)-2-hydroxymethyl-7-methyl-3-aza-bicyclo[3.3.0]-octane-3-carboxylic acid tert.-butyl ester A mixture of (1S,2S,5R)-3-benzyl-2-hydroxymethyl-7-methyl-3-aza-bicyclo[3.3.0]-octane (342 mg), Pd—C (50% H₂O) (277 mg), Boc₂O (456 mg, 1.5 eq) in EA (13 mL) was stirred under hydrogen (1 bar) for 16 h. After filtration through celite and removal of the solvents the title compound was obtained as a yellow oil.

¹H-NMR (CDCl₃): δ=1.05 (m, 3H), 1.45 (s, 9H); 2.05-2.55 (m, 6H); 3.25-3.75 (m, 5H); 4.45 (m, 1H).

A.3.4 Synthesis of (1S,2S,5R)-2-formyl-7-methyl-3-aza-bicyclo[3.3.0]-octane-3-carboxylic acid tert.-butyl ester To a cold (−60° C.) solution of oxalyl chloride (0.081 mL, 1.2 eq) in dry DCM (2.2 mL) was added dropwise a solution of DMSO (0.13 mL, 2.2 eq) in dry DCM (1.7 mL) within 4 min. After 10 min, was added dropwise (1S,2S,5R)-2-hydroxymethyl-7-methyl-3-aza-bicyclo[3.3.0]-octane-3-carboxylic acid tert.-butyl ester (206 mg) in dry DCM (1.2 mL) during 5 min. After 2 min a white suspension was formed. Stirring was continued 30 min at −55° C., then DIPEA (0.690 mL, 5 eq) (which was dried over 3A M.S.) was added during 3-4 min. The reaction mixture was allowed to come to RT, diluted with water and extracted with DCM. The combined org. extracts were washed with citric acid (5%), brine, dried over anh. MgSO$_4$, filtered and evaporated to yield the title compound as an oil, which was used for the next step without further purification.

$^1$H-NMR (CDCl$_3$): δ=1.05 (m, 3H), 1.25-1.35 (m, 2H); 1.45 (d, 9H); 1.95-2.25 (m, 3H); 2.55 (m, 2H); 3.25-4.15 (m, 3H); 9.45 (s, 1H).

A.3.5 Synthesis of (1S,2S,5R)-2-(benzylamino-methyl)-7-methyl-3-aza-bicyclo[3.3.0]-octane-3-carboxylic acid tert.-butyl ester Benzylamine (0.155 mL, 1.75 eq) was added to a solution of (1S,2S,5R)-2-formyl-7-methyl-3-aza-bicyclo[3.3.0]-octane-3-carboxylic acid tert.-butyl ester (206 mg, 1 eq) in chloroform (6 mL). After 15 min the mixture was treated with NaBH(OAc)$_3$ (173 mg, 1 eq), and stirred for 16 h. The reaction mixture was poured into a sat. aq. NaHCO$_3$ solution. The layers were separated and the aq. layer was extracted twice with chloroform. The combined org. extracts were washed with sat. NaHCO$_3$ solution, dried over anh. MgSO$_4$, filtered and concentrated in vacuo to give a crude yellow oil. FC (EA/n-heptane: 3/7 to 7/3) gave the title compound as a colourless oil LC-MS: $t_R$=0.89 min; [M+H]$^+$=345.

A.3.6 Synthesis of (1S,2S,5R)-2-aminomethyl-7-methyl-3-aza-bicyclo[3.3.0]-octane-3-carboxylic acid tert.-butyl ester A solution of (1S,2S,5R)-2-(benzylamino-methyl)-7-methyl-3-aza-bicyclo[3.3.0]-octane-3-carboxylic acid tert.-butyl ester (264 mg) in EtOH (12 mL) was treated with Pd/C 10% (100 mg) and stirred under hydrogen (1 bar) for 16 h. After filtration through celite and removal of the solvents the title compound was obtained as a colourless oil which was used without further purification.

$^1$H-NMR (CDCl$_3$): δ=0.95 (m, 3H); 1.35 (m, 2H); 1.45 (s, 9H); 1.85-2.45 (m, 8H); 3.25-3.75 (m, 2H).

A.4 Synthesis of 3-acyl-substituted (1S,2S,5R)-2-(amino-methyl)-3-aza-bicyclo[3.3.0]-octane derivatives

A.4.1 Synthesis of (1S,2S,5R)-2-[(2,2,2-trifluoro-acetylamino)-methyl]-7-methyl-3-aza-bicyclo[3.3.0]-octane-3-carboxylic acid tert.-butyl ester Ethyl trifluoroacetate (0.7 mL, 1.4 eq) was added to a solution of (1S,2S,5R)-2-aminomethyl-7-methyl-3-aza-bicyclo[3.3.0]-octane-3-carboxylic acid tert.-butyl ester (1.1 g) in dry THF (14 mL). The reaction mixture was stirred at RT for 1 h. Solvent and excess ethyl trifluoroacetate were evaporated in vacuo. The resulting product was then used for the next step without purification LC-MS: $t_R$=1.04 min; [M+H]$^+$=351.

A.4.2 Synthesis of N-[(1S,2S,5R)-7-methyl-3-aza-bicyclo[3.3.0]oct-2-ylmethyl]-2,2,2-trifluoro-acetamide To a cold (0° C.) solution of (1S,2S,5R)-2-[(2,2,2-trifluoro-acetylamino)-methyl]-7-methyl-3-aza-bicyclo[3.3.0]-octane-3-carboxylic acid tert.-butyl ester (1.51 g) in DCM (13 mL) was slowly added TFA (3.31 mL, 10 eq). The reaction mixture was allowed to warm at RT and stirred overnight. Solvent and excess of TFA were removed in vacuo and the product was used for the next step without further purification.

LC-MS: $t_R$=0.69 min; [M+H]$^+$=251.

A.4.3 Synthesis of 2,2,2-trifluoro-N-[(1S,2S,5R)-3-(2-methyl-5-m-tolyl-thiazole-4-carbonyl)-7-methyl-3-aza-bicyclo[3.3.0]oct-2-ylmethyl]-acetamide A solution of 2-methyl-5-m-tolyl-thiazole-4-carboxylic acid (1 g, 1 eq), DIPEA (3.7 mL, eq) and TBTU (1.4 g, 1 eq) in dry DMF (15 mL) was stirred at RT for 15 min. Then was added a solution of N-[(1S,2S,5R)-7-methyl-3-aza-bicyclo[3.3.0]oct-2-ylmethyl]-2,2,2-trifluoro-acetamide (1.082 g, 1 eq) in dry DMF (15 mL). The resulting reaction mixture was stirred for 16 h, poured into water and diluted with EA. The org. phase was washed with a sat. aq. NaHCO$_3$ solution, brine, dried over anh. MgSO$_4$, filtered and concentrated to yield a crude yellow solid. FC (EA/n-heptane: 3/7 to 7/3) gave the title compound as a white solid.

LC-MS: $t_R$=1.06 min; [M+H]$^+$=466.

A.4.4 Synthesis of [(1S,2S,5R)-2-aminomethyl-7-methyl-3-aza-bicyclo[3.3.0]oct-3-yl]-(2-methyl-5-m-tolyl-thiazol-4-yl)-methanone

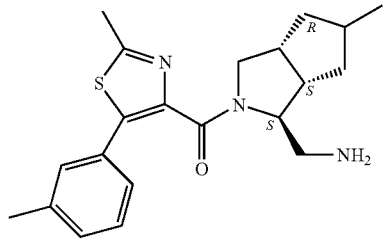

2,2,2-trifluoro-N-[(1S,2S,5R)-3-(2-methyl-5-m-tolyl-thiazole-4-carbonyl)-7-methyl-3-aza-bicyclo[3.3.0]oct-2-ylmethyl]-acetamide (1.96 g) was dissolved in MeOH (20 mL) and a sat. aq. K$_2$CO$_3$ solution was added (20 mL). The reaction mixture was stirred overnight at RT. Ether was added to the reaction mixture and the org. layer was extracted with aq. HCl (25%) and aq. HCl (1M). The org. phase was discarded and the aq. layers were basified with aq. 30% NaOH and then extracted with DCM. The combined org. extracts were washed with a sat. aq. NaHCO$_3$ solution, dried over anh. MgSO$_4$, filtered and concentrated to yield the title compound as a light orange oil which was used without further purification.

LC-MS: $t_R$=0.82 min; [M+H]$^+$=370.

A.5 Synthesis of (1S,2S,5R)-2-(acylamino-methyl)-3-aza-bicyclo[3.3.0]-octane derivatives

A.5.1 Synthesis of (1S,2S,5R)-2-(acylamino-methyl)-3-aza-bicyclo[3.3.0]-octane-3-carboxylic acid tert.-butyl ester derivatives (general procedure)

To a solution of the respective carboxylic acid $R^3$—COOH (1 eq) in DMF (0.2 mmol/0.5 mL) are added successively DIPEA (5 eq) and TBTU (1 eq). The reaction mixture is stirred for 15 min. at RT and then is added a solution of (1S,2S,5R)-1-aminomethyl-3-aza-bicyclo[3.3.0]-octane-3-carboxylic acid tert.-butyl ester derivative (1 eq) in DMF (0.5 mL). The stirring at RT is continued for 16 h, the reaction mixture is poured into water and diluted with EA. The org. phase is washed with sat. NaHCO$_3$ solution and water. After drying over anh. MgSO$_4$ and removal of solvents in vacuo the desired compounds are obtained which are used without further purification.

(1S,2S,5R)-2-{[(3,4-Dihydro-benzo[1,4]dioxine-5-carbonyl)-amino]-methyl}-3-aza-bicyclo[3.3.0]octane-3-carboxylic acid tert.-butyl ester

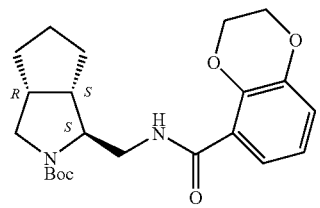

prepared by reaction of (1S,2S,5R)-1-aminomethyl-3-aza-bicyclo[3.3.0]-octane-3-carboxylic acid tert.-butyl ester with commercially available 2,3-dihydro-benzo[1,4]dioxine-5-carboxylic acid.

LC-MS: $t_R$=1.00 min; [M+H]$^+$=403.

(1S,2S,5R)-2-{[(6-Methyl-imidazo[2,1-b]thiazole-5-carbonyl)-amino]-methyl}-3-aza-bicyclo[3.3.0]octane-3-carboxylic acid tert.-butyl ester

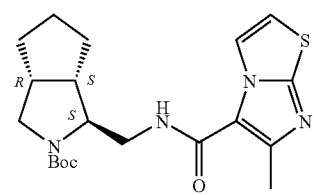

prepared by reaction of (1S,2S,5R)-1-aminomethyl-3-aza-bicyclo[3.3.0]-octane-3-carboxylic acid tert.-butyl ester with commercially available 6-methyl-imidazo[2,1-b]thiazole-5-carboxylic acid.

LC-MS: $t_R$=0.89 min; [M+H]$^+$=405.

(1S,2S,5R)-2-{[(Benzo[d]isoxazole-3-carbonyl)-amino]-methyl}-3-aza-bicyclo[3.3.0]octane-3-carboxylic acid tert.-butyl ester

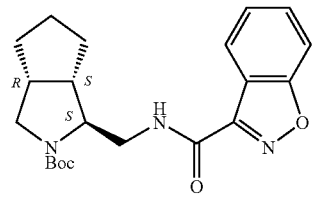

prepared by reaction of (1S,2S,5R)-1-aminomethyl-3-aza-bicyclo[3.3.0]-octane-3-carboxylic acid tert.-butyl ester with commercially available benzo[d]isoxazole-3-carboxylic acid.

LC-MS: $t_R$=1.03 min; [M+H]$^+$=386.

(1S,2S,5R)-2-{[Imidazo[2,1-b]thiazole-5-carbonyl)-amino]-methyl}-3-aza-bicyclo[3.3.0]octane-3-carboxylic acid tert.-butyl ester

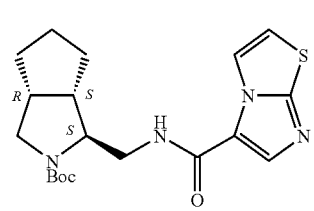

prepared by reaction of (1S,2S,5R)-1-aminomethyl-3-aza-bicyclo[3.3.0]-octane-3-carboxylic acid tert.-butyl ester with imidazo[2,1-b]thiazole-5-carboxylic acid which was synthesised by saponification of the corresponding ethyl ester derivative (WO1995/029922) with NaOH in a mixture water/EtOH.

LC-MS: $t_R$=0.90 min; [M+H]$^+$=391.

(1S,2S,5R)-2-{[(Benzo[d]isothiazole-3-carbonyl)-amino]-methyl}-3-aza-bicyclo[3.3.0]octane-3-carboxylic acid tert.-butyl ester

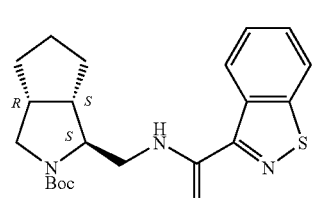

prepared by reaction of (1S,2S,5R)-1-aminomethyl-3-aza-bicyclo[3.3.0]-octane-3-carboxylic acid tert.-butyl ester with benzo[d]isothiazole-3-carboxylic acid (WO2004/029050).

LC-MS: $t_R$=1.08 min; [M+H]$^+$=402.

(1S,2S,5R)-2-{[6-Methyl-(imidazo[2,1-b]thiazole-5-carbonyl)-amino]-methyl}-7-methyl-3-aza-bicyclo[3.3.0]octane-3-carboxylic acid tert.-butyl ester

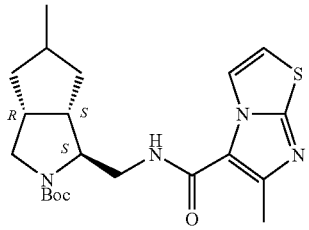

prepared by reaction of (1S,2S,5R)-2-aminomethyl-7-methyl-3-aza-bicyclo[3.3.0]-octane-3-carboxylic acid tert.-butyl ester with commercially available 6-methyl-imidazo[2,1-b]thiazole-5-carboxylic acid.

LC-MS: $t_R$=0.93 min; [M+H]$^+$=419.

(1S,2S,5R)-2-{[(3,4-Dihydro-benzo[1,4]dioxine-5-carbonyl)-amino]-methyl}-7-methyl-3-aza-bicyclo[3.3.0]octane-3-carboxylic acid tert.-butyl ester

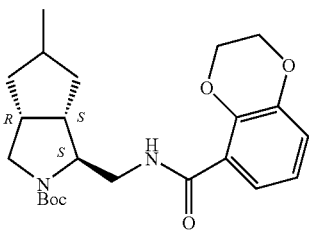

prepared by reaction of (1S,2S,5R)-1-aminomethyl-7-methyl-3-aza-bicyclo[3.3.0]-octane-3-carboxylic acid tert.-butyl ester with commercially available 2,3-dihydro-benzo[1,4]dioxine-5-carboxylic acid.

LC-MS: $t_R$=1.03 min; [M+H]$^+$=417.

(1S,2S,5R)-2-{[(Benzo[d]isoxazole-3-carbonyl)-amino]-methyl}-7-methyl-3-aza-bicyclo[3.3.0]octane-3-carboxylic acid tert.-butyl ester

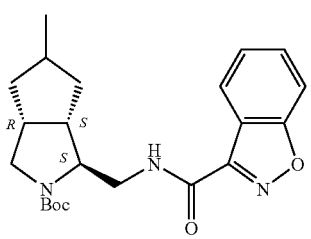

prepared by reaction of (1S,2S,5R)-1-aminomethyl-7-methyl-3-aza-bicyclo[3.3.0]-octane-3-carboxylic acid tert.-butyl ester with commercially available benzo[d]isoxazole-3-carboxylic acid.

LC-MS: $t_R$=1.06 min; [M]$^+$=399.

(1S,2S,5R)-2-{[(Imidazo[2,1-b]thiazole-5-carbonyl)-amino]-methyl}-7-methyl-3-aza-bicyclo[3.3.0]octane-3-carboxylic acid tert.-butyl ester

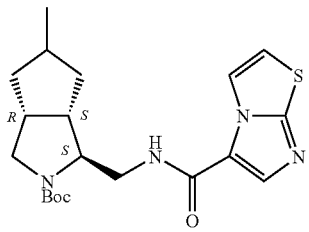

prepared by reaction of (1S,2S,5R)-1-aminomethyl-7-methyl-3-aza-bicyclo[3.3.0]-octane-3-carboxylic acid tert.-butyl ester with imidazo[2,1-b]thiazole-5-carboxylic acid which was synthesised by saponification of the corresponding ethyl ester derivative (WO1995/029922) with NaOH in a mixture water/EtOH.

LC-MS: $t_R$=0.94 min; [M+H]$^+$=405.

(1S,2S,5R)-2-{[(Benzo[d]isothiazole-3-carbonyl)-amino]-methyl}-7-methyl-3-aza-bicyclo[3.3.0]octane-3-carboxylic acid tert.-butyl ester

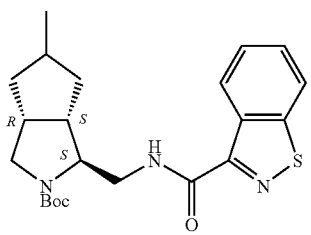

prepared by reaction of (1S,2S,5R)-1-aminomethyl-7-methyl-3-aza-bicyclo[3.3.0]-octane-3-carboxylic acid tert.-butyl ester with benzo[d]isothiazole-3-carboxylic acid (WO2004/029050).

LC-MS: $t_R$=1.11 min; [M+H]$^+$=416.

(1S,2S,5R)-2-{[Imidazo[2,1-b]thiazole-6-carbonyl)-amino]-methyl}-7-methyl-3-aza-bicyclo[3.3.0]octane-3-carboxylic acid tert.-butyl ester

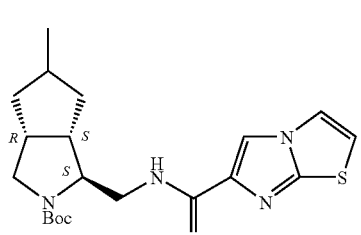

prepared by reaction of (1S,2S,5R)-1-aminomethyl-7-methyl-3-aza-bicyclo[3.3.0]-octane-3-carboxylic acid tert.-butyl ester with commercially available imidazo[2,1-b]thiazole-6-carboxylic acid.

LC-MS: $t_R$=0.98 min; [M+H]$^+$=405.

(1S,2S,5R)-2-{[(1-Methyl-1H-indazole-3-carbonyl)-amino]-methyl}-7-methyl-3-aza-bicyclo[3.3.0]octane-3-carboxylic acid tert.-butyl ester

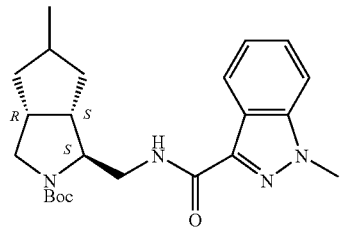

prepared by reaction of (1S,2S,5R)-1-aminomethyl-7-methyl-3-aza-bicyclo[3.3.0]-octane-3-carboxylic acid tert.-butyl ester with commercially available 1-methyl-1H-indazole-3-carboxylic acid.

LC-MS: $t_R$=1.07 min; [M]$^+$=528.

(1S,2S,5R)-2-{[(3,5-Dimethyl-isoxazole-4-carbonyl)-amino]-methyl}-7-methyl-3-aza-bicyclo[3.3.0]octane-3-carboxylic acid tert.-butyl ester

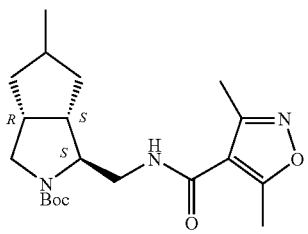

prepared by reaction of (1S,2S,5R)-1-aminomethyl-7-methyl-3-aza-bicyclo[3.3.0]-octane-3-carboxylic acid tert.-butyl ester with commercially available 3,5-dimethyl-oxazole-4-carboxylic acid.

LC-MS: $t_R$=0.99 min; [M+H]$^+$=378.

A.5.2 Deprotection of (1S,2S,5R)-2-(acylaminomethyl)-3-aza-bicyclo[3.3.0]-octane-3-carboxylic acid tert.-butyl ester derivatives (general procedure)

To a cold (0° C.) solution of (1S,2S,5R)-2-(acylaminomethyl)-3-aza-bicyclo[3.3.0]-octane-3-carboxylic acid tert.-butyl ester derivative in DCM (1 mL/0.2 mmol), is added slowly TFA (5 eq). The reaction mixture is allowed to stir at RT for 5 h and the mixture is concentrated in vacuo to give the respective deprotected product which is used without further purification.

3,4-Dihydro-benzo[1,4]dioxine-5-carboxylic acid-[(1S,2S,5R)-3-aza-bicyclo[3.3.0]oct-2-ylmethyl]-amide

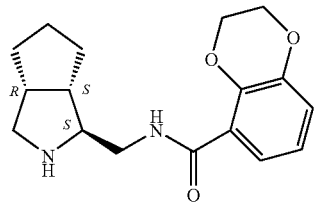

prepared by deprotection of (1S,2S,5R)-2-{[(3,4-dihydro-benzo[1,4]dioxine-5-carbonyl)-amino]-methyl}-3-aza-bicyclo[3.3.0]octane-3-carboxylic acid tert.-butyl ester.

LC-MS: $t_R$=0.68 min; [M+H]$^+$=303.

6-Methyl-imidazo[2,1-b]thiazole-5-carboxylic acid-[(1S,2S,5R)-3-aza-bicyclo[3.3.0]oct-2-ylmethyl]-amide

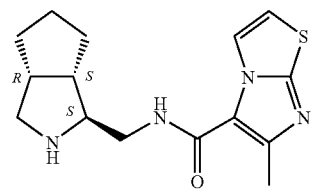

prepared by deprotection of (1S,2S,5R)-2-{[(6-methyl-imidazo[2,1-b]thiazole-5-carbonyl)-amino]-methyl}-3-aza-bicyclo[3.3.0]octane-3-carboxylic acid tert.-butyl ester.

LC-MS: $t_R$=0.56 min; [M+H]$^+$=305.

Benzo[d]isoxazole-3-carboxylic acid-[(1S,2S,5R)-3-aza-bicyclo[3.3.0]oct-2-ylmethyl]-amide

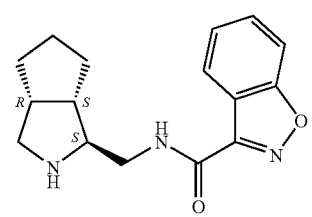

prepared by deprotection of (1S,2S,5R)-2-{[(benzo[d]isoxazole-3-carbonyl)-amino]-methyl}-3-aza-bicyclo[3.3.0]octane-3-carboxylic acid tert.-butyl ester.

LC-MS: $t_R$=0.67 min; [M+H]$^+$=286.

Imidazo[2,1-b]thiazole-5-carboxylic acid-[(1S,2S,5R)-3-aza-bicyclo[3.3.0]oct-2-ylmethyl]-amide

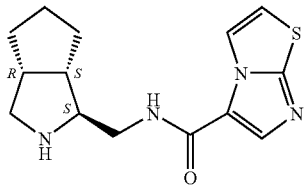

prepared by deprotection of (1S,2S,5R)-2-{[(imidazo[2,1-b]thiazole-5-carbonyl)-amino]-methyl}-3-aza-bicyclo[3.3.0]octane-3-carboxylic acid tert.-butyl ester.

LC-MS: $t_R$=0.57 min; [M+H]$^+$=291.

Benzo[d]isothiazole-3-carboxylic acid-[(1S,2S,5R)-3-aza-bicyclo[3.3.0]oct-2-ylmethyl]-amide

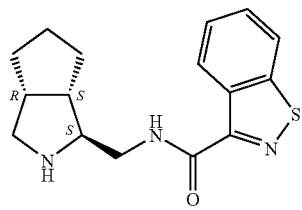

prepared by deprotection of (1S,2S,5R)-2-{[(benzo[d]isothiazole-3-carbonyl)-amino]-methyl}-3-aza-bicyclo[3.3.0]octane-3-carboxylic acid tert.-butyl ester.

LC-MS: $t_R$=0.72 min; [M+H]$^+$=302.

6-Methyl-imidazo[2,1-b]thiazole-5-carboxylic acid-[(1S,2S,5R)-7-methyl-3-aza-bicyclo[3.3.0]oct-2-ylmethyl]-amide

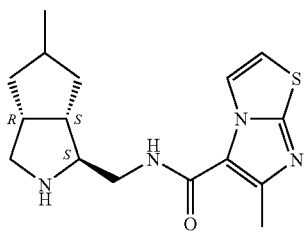

prepared by deprotection of (1S,2S,5R)-2-{[(6-methyl-imidazo[2,1-b]thiazole-5-carbonyl)-amino]-methyl}-7-methyl-3-aza-bicyclo[3.3.0]octane-3-carboxylic acid tert.-butyl ester.

LC-MS: $t_R$=0.62 min; [M+H]$^+$=319.

3,4-Dihydro-benzo[1,4]dioxine-5-carboxylic acid-[(1S,2S,5R)-7-methyl-3-aza-bicyclo[3.3.0]oct-2-ylmethyl]-amide

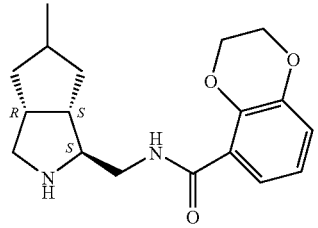

prepared by deprotection of (1S,2S,5R)-2-{[(3,4-dihydro-benzo[1,4]dioxine-5-carbonyl)-amino]-methyl}-7-methyl-3-aza-bicyclo[3.3.0]octane-3-carboxylic acid tert.-butyl ester.

LC-MS: $t_R$=0.72 min; [M+H]$^+$=317.

Benzo[d]isoxazole-3-carboxylic acid-[(1S,2S,5R)-7-methyl-3-aza-bicyclo[3.3.0]oct-2-ylmethyl]-amide

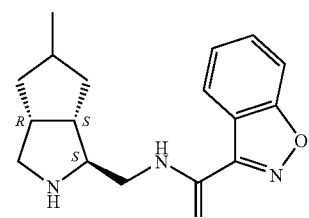

prepared by deprotection of (1S,2S,5R)-2-{[(benzo[d]isoxazole-3-carbonyl)-amino]-methyl}-7-methyl-3-aza-bicyclo[3.3.0]octane-3-carboxylic acid tert.-butyl ester LC-MS: $t_R$=0.72 min; [M+H]$^+$=300.

Imidazo[2,1-b]thiazole-5-carboxylic acid-[(1S,2S,5R)-7-methyl-3-aza-bicyclo[3.3.0]oct-2-ylmethyl]-amide

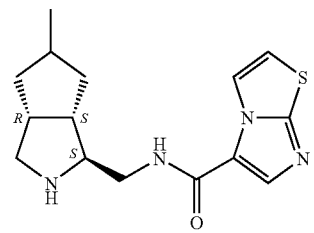

prepared by deprotection of (1S,2S,5R)-2-{[(imidazo[2,1-b]thiazole-5-carbonyl)-amino]-methyl}-7-methyl-3-aza-bicyclo[3.3.0]octane-3-carboxylic acid tert.-butyl ester.

LC-MS: $t_R$=0.63 min; [M+H]$^+$=305.

51

Benzo[d]isothiazole-3-carboxylic acid-[(1S,2S,5R)-7-methyl-3-aza-bicyclo[3.3.0]oct-2-ylmethyl]-amide

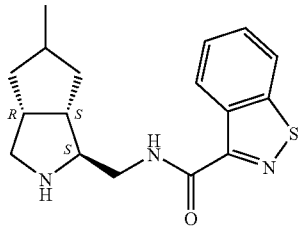

prepared by deprotection of (1S,2S,5R)-2-{[(benzo[d]isothiazole-3-carbonyl)-amino]-methyl}-7-methyl-3-aza-bicyclo[3.3.0]octane-3-carboxylic acid tert.-butyl ester.

LC-MS: $t_R$=0.77 min; $[M+H]^+$=316.

Imidazo[2,1-b]thiazole-6-carboxylic acid-[(1S,2S,5R)-7-methyl-3-aza-bicyclo[3.3.0]oct-2-ylmethyl]-amide

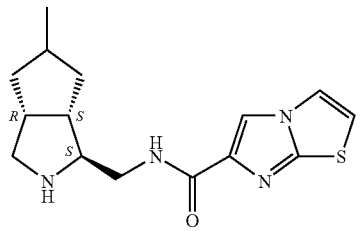

prepared by deprotection of (1S,2S,5R)-2-{[(imidazo[2,1-b]thiazole-6-carbonyl)-amino]-methyl}-7-methyl-3-aza-bicyclo[3.3.0]octane-3-carboxylic acid tert.-butyl ester.

LC-MS: $t_R$=0.64 min; $[M+H]^+$=305.

1-Methyl-1H-indazole-3-carboxylic acid-[(1S,2S,5R)-7-methyl-3-aza-bicyclo[3.3.0]oct-2-ylmethyl]-amide

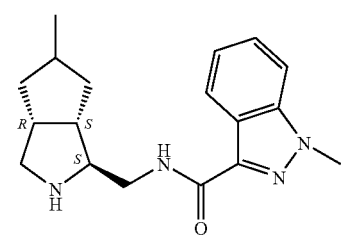

prepared by deprotection of (1S,2S,5R)-2-{[(1-methyl-1H-indazole-3-carbonyl)-amino]-methyl}-7-methyl-3-aza-bicyclo[3.3.0]octane-3-carboxylic acid tert.-butyl ester.

LC-MS: $t_R$=0.74 min; $[M+H]^+$=313.

52

3,5-Dimethyl-isoxazole-4-carboxylic acid-[(1S,2S,5R)-7-methyl-3-aza-bicyclo[3.3.0]oct-2-ylmethyl]-amide

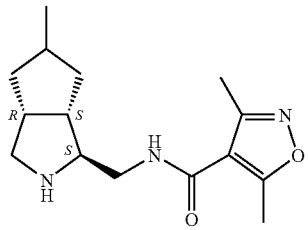

prepared by deprotection of (1S,2S,5R)-2-{[(3,5-dimethyl-oxazole-4-carbonyl)-amino]-methyl}-7-methyl-3-aza-bicyclo[3.3.0]octane-3-carboxylic acid tert.-butyl ester.

LC-MS: $t_R$=0.63 min; $[M+H]^+$=278.

A.6 Synthesis of (1S,2S,5R)-(2-aminomethyl-7,7-difluoro-3-aza-bicyclo[3.3.0]-oct-3-yl)-(2-methyl-5-m-tolyl-thiazol-4-yl)-methanone

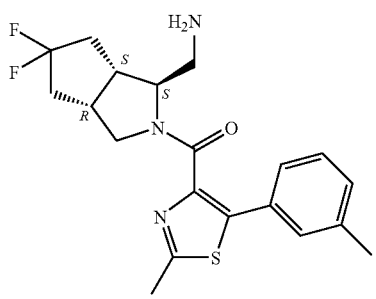

A.6.1 Synthesis of (1S,2S,5R)-2-(3-benzyl-7,7-difluoro-3-azabicyclo[3.3.0]oct-2-ylmethyl)-isoindole-1,3-dione To a cold solution of triphenylphosphine (1.8 g) in dry THF (90 mL) was added dropwise DEAD 40% in toluene (3.15 mL). Then was added successively phthalimide (1.01 g) and a solution of (3-benzyl-7,7-difluoro-3-azabicyclo[3.3.0]oct-2-yl)-methanol (WO03/062265) (1.83 g) in dry THF (10 mL). The reaction mixture was stirred at RT overnight, diluted with EA, washed with water. The organic phase was washed with sat. NaHCO$_3$ solution, dried (MgSO$_4$), filtered and concentrated to yield a crude oil. FC (n-heptane/EA: 7/3 to 1/1) gave 1.73 g (64%) of the title compound as a white solid. LC-MS: $t_R$=0.87 min; $[M+H]^+$=397.47.

A.6.2 Synthesis of (1S,2S,5R)-2-(7,7-difluoro-3-azabicyclo[3.3.0]oct-2-ylmethyl)-isoindole-1,3-dione To a suspension of (1S,2S,5R)-2-(3-benzyl-7,7-difluoro-3-azabicyclo[3.3.0]oct-2-ylmethyl)-isoindole-1,3-dione (1.73 g), Pd—C 10% (1.7 g) in dry MeOH (146 mL) was added ammonium formate (1.38 g). The reaction mixture was stirred at reflux for 16 h, cooled to RT and filtered over a pad of celite. The filtrate was concentrated in vacuo, partitioned between DCM/water. The aqueous phase was concentrated to yield 0.8 g (60%) of the title compound as a white solid LC-MS: $t_R$=0.66 min; $[M+H]^+$=306.92.

A.6.3 Synthesis of (1S,2S,5R)-2-[3-(2-methyl-5-m-tolyl-thiazole-4-carbonyl)-7,7-difluoro-3-azabicyclo[3.3.0]oct-2-ylmethyl]-isoindole-1,3-dione A mixture of 2-methyl-5-m-tolyl-thiazole-4-carboxylic acid (208 mg), (1S,2S,5R)-2-(7,7-difluoro-3-azabicyclo[3.3.0]oct-2-ylmethyl)-isoindole-1,3-dione (273 mg), DIPEA (0.41 mL) in dry DMF (6 mL) was stirred at RT for 4 h. The reaction mixture was directly purified by preparative HPLC to give the title compound (130 mg, 28%) as an oil. LC-MS: $t_R$=1.02 min; [M+H]$^+$=521.99

A.6.4 Synthesis of (1S,2S,5R)-(2-aminomethyl-7,7-difluoro-3-aza-bicyclo[3.3.0]-oct-3-yl)-(2-methyl-5-m-tolyl-thiazol-4-yl)-methanone A mixture of (1S,2S,5R)-2-[3-(2-methyl-5-m-tolyl-thiazole-4-carbonyl)-7,7-difluoro-3-azabicyclo[3.3.0]oct-2-ylmethyl)-isoindole-1,3-dione (130 mg), hydrazine monohydrate (0.078 mL) in EtOH (10 mL) was stirred at reflux for 1 h 45. After cooling to RT, the reaction mixture was concentrated in vacuo, dissolved in DCM, washed twice with water, brine, dried (MgSO$_4$), filtered and concentrated to yield the title compound (90 mg, 92%) as a colorless oil which was used for the next step without further purification. LC-MS: $t_R$=0.79 min; [M+H]$^+$=392

Preparation of Examples

General Procedure I

To a solution of the respective carboxylic acid derivative A-COOH (1 eq) in DMF (0.6 mL/0.2 mmol) are added successively DIPEA (5 eq) and TBTU (1 eq). The reaction mixture is stirred at RT for 15 min and then a solution of the respective (1S,2S,5R)-2-(acylamino-methyl)-3-aza-bicyclo[3.3.0]-octane derivative (Intermediate A.5, 1 eq) in DMF (0.6 mL/0.2 mmol) is added. The mixture is stirred over night and purified by prep. HPLC to give the respective final compounds.

The compounds of the following examples have been prepared using general procedure I.

Example 1

2,3-Dihydro-benzo[1,4]dioxine-5-carboxylic acid-(1S,2S,5R)-[3-(2-methyl-5-m-tolyl-thiazole-4-carbonyl)-3-aza-bicyclo[3.3.0]oct-2-ylmethyl]-amide prepared by reaction of 3,4-dihydro-benzo[1,4]dioxine-5-carboxylic acid-[(1S,2S,5R)-3-aza-bicyclo[3.3.0]oct-2-ylmethyl]-amide with 2-methyl-5-m-tolyl-thiazole-4-carboxylic acid.
LC-MS: $t_R$=1.03 min; [M+H]$^+$=518.

Example 2

6-Methyl-imidazo[2,1-b]thiazole-5-carboxylic acid-(1S,2S,5R)-[3-(2-methyl-5-m-tolyl-thiazole-4-carbonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 2-methyl-5-m-tolyl-thiazole-4-carboxylic acid.
LC-MS: $t_R$=0.91 min; [M+H]$^+$=520.

Example 3

6-Methyl-imidazo[2,1-b]thiazole-5-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 2-methyl-5-m-tolyl-thiazole-4-carboxylic acid.
LC-MS: $t_R$=0.95 min; [M+H]$^+$=534.

Example 4

2,3-Dihydro-benzo[1,4]dioxine-5-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of 3,4-dihydro-benzo[1,4]dioxine-5-carboxylic acid-[(1S,2S,5R)-7-methyl-3-aza-bicyclo[3.3.0]oct-2-ylmethyl]-amide with 2-methyl-5-m-tolyl-thiazole-4-carboxylic acid.
LC-MS: $t_R$=1.06 min; [M+H]$^+$=532.

Example 5

1-Methyl-indazole-3-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of 1-methyl-1H-indazole-3-carboxylic acid-[(1S,2S,5R)-7-methyl-3-aza-bicyclo[3.3.0]oct-2-ylmethyl]-amide with 2-methyl-5-m-tolyl-thiazole-4-carboxylic acid.
LC-MS: $t_R$=1.07 min; [M+H]$^+$=528.

Example 6

3,5-Dimethyl-isoxazole-4-carboxylic acid-(1S,2S,5R)-[7-methyl-3-(2-methyl-5-m-tolyl-thiazole-4-carbonyl)-3-aza-bicyclo[3.3.0]-2-ylmethyl]-amide prepared by reaction of 3,5-dimethyl-isoxazole-4-carboxylic acid-[(1S,2S,5R)-7-methyl-3-aza-bicyclo[3.3.0]oct-2-ylmethyl]-amide with 2-methyl-5-m-tolyl-thiazole-4-carboxylic acid.
LC-MS: $t_R$=1.03 min; [M+H]$^+$=493.

Example 7

Benzo[d]isoxazole-3-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of benzo[d]isoxazole-3-carboxylic acid-[(1S,2S,5R)-7-methyl-3-aza-bicyclo[3.3.0]oct-2-ylmethyl]-amide with 2-methyl-5-m-tolyl-thiazole-4-carboxylic acid.
LC-MS: $t_R$=1.07 min; [M+H]$^+$=515.

Example 8

Benzo[d]isoxazole-3-carboxylic acid-(1S,2S,5R)-[3-(2-methyl-5-m-tolyl-thiazole-4-carbonyl)-3-aza-bicyclo[3.3.0]oct-2-ylmethyl]-amide prepared by reaction of benzo[d]isoxazole-3-carboxylic acid-[(1S,2S,5R)-3-aza-bicyclo[3.3.0]oct-2-ylmethyl]-amide with 2-methyl-5-m-tolyl-thiazole-4-carboxylic acid.
LC-MS: $t_R$=1.04 min; [M+H]$^+$=501.

Example 9

Benzo[d]isothiazole-3-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of benzo[d]isothiazole-3-carboxylic acid-[(1S,2S,5R)-7-methyl-3-aza-bicyclo[3.3.0]oct-2-ylmethyl]-amide with 2-methyl-5-m-tolyl-thiazole-4-carboxylic acid.
LC-MS: $t_R$=1.12 min; [M+H]$^+$=531.

Example 10

Benzo[d]isothiazole-3-carboxylic acid-(1S,2S,5R)-[3-(2-methyl-5-m-tolyl-thiazole-4-carbonyl)-3-aza-bicyclo[3.3.0]oct-2-ylmethyl]-amide prepared by reaction of benzo[d]isothiazole-3-carboxylic acid-[(1S,2S,5R)-3-aza-bicyclo[3.3.0]oct-2-ylmethyl]-amide with 2-methyl-5-m-tolyl-thiazole-4-carboxylic acid.
LC-MS: $t_R$=1.08 min; [M+H]$^+$=517.

Example 11

Imidazo[2,1-b]thiazole-5-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of with imidazo[2,1-b]thiazole-5-carboxylic acid-[(1S,2S,5R)-7-methyl-3-aza-bicyclo[3.3.0]oct-2-ylmethyl]-amide 2-methyl-5-m-tolyl-thiazole-4-carboxylic acid.
LC-MS: $t_R$=0.95 min; [M+H]$^+$=520.

Example 12

Imidazo[2,1-b]thiazole-5-carboxylic acid-(1S,2S,5R)-[3-(2-methyl-5-m-tolyl-thiazole-4-carbonyl)-3-aza-bicyclo[3.3.0]oct-2-ylmethyl]-amide prepared by reaction of imidazo[2,1-b]thiazole-5-carboxylic acid-[(1S,2S,5R)-3-aza-bicyclo[3.3.0]oct-2-ylmethyl]-amide with 2-methyl-5-m-tolyl-thiazole-4-carboxylic acid.
LC-MS: $t_R$=0.92 min; [M+H]$^+$=506.

Example 13

Imidazo[2,1-b]thiazole-6-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of imidazo[2,1-b]thiazole-6-carboxylic acid-[(1S,2S,5R)-7-methyl-3-aza-bicyclo[3.3.0]oct-2-ylmethyl]-amide with 2-methyl-5-m-tolyl-thiazole-4-carboxylic acid.
LC-MS: $t_R$=0.98 min; [M+H]$^+$=520.

Preparation of Examples

General Procedure II

To a solution of the respective carboxylic acid derivative R$^3$—COOH (1 eq) in DMF (0.6 mL/0.2 mmol) are added successively DIPEA (5 eq) and TBTU (1 eq). The reaction mixture is stirred for 15 min. and then a solution of the respective 3-acyl-substituted (1S,2S,5R)-2-(amino-methyl)-3-aza-bicyclo[3.3.0]-octane derivative (Intermediate A.4, 1 eq) or (1S,2S,5R)-(2-aminomethyl-7,7-difluoro-3-aza-bicyclo[3.3.0]-oct-3-yl)-(2-methyl-5-m-tolyl-thiazol-4-yl)-methanone (intermediate A.6, 1 eq) in DMF (0.6 mL/0.2 mmol) is added. The mixture is stirred over night and purified by prep. HPLC to give the respective final compounds.

The compounds of the following examples have been prepared using general procedure II.

Example 14

(1S,2S,5R)-3-Bromo-N-[7-methyl-3-(2-methyl-5-m-tolyl-thiazole-4-carbonyl)-3-aza-bicyclo[3.3.0]oct-2-ylmethyl]-benzamide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 3-bromo-benzoic acid.
LC-MS: $t_R$=1.08 min; [M+H]$^+$=554.

Example 15

(1S,2S,5R)-3-Chloro-N-[7-methyl-3-(2-methyl-5-m-tolyl-thiazole-4-carbonyl)-3-aza-bicyclo[3.3.0]oct-2-ylmethyl]-benzamide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 3-chloro-benzoic acid.
LC-MS: $t_R$=1.14 min; [M+H]$^+$=509.

Example 16

(1S,2S,5R)-3-Fluoro-N-[7-methyl-3-(2-methyl-5-m-tolyl-thiazole-4-carbonyl)-3-aza-bicyclo[3.3.0]oct-2-ylmethyl]-benzamide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 3-fluoro-benzoic acid.
LC-MS: $t_R$=1.12 min; [M+H]$^+$=492.

Example 17

(1S,2S,5R)-3-Methoxy-N-[7-methyl-3-(2-methyl-5-m-tolyl-thiazole-4-carbonyl)-3-aza-bicyclo[3.3.0]oct-2-ylmethyl]-benzamide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 3-methoxy-benzoic acid.
LC-MS: $t_R$=1.11 min; [M+H]$^+$=504.

Example 18

(1S,2S,5R)—N-[7-Methyl-3-(2-methyl-5-m-tolyl-thiazole-4-carbonyl)-3-aza-bicyclo[3.3.0]oct-2-ylmethyl]-3-trifluoromethyl-benzamide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 3-(trifluoromethyl)-benzoic acid acid.
LC-MS: $t_R$=1.15 min; [M+H]$^+$=542.

Example 19

(1S,2S,5R)-3-Methyl-N-[7-methyl-3-(2-methyl-5-m-tolyl-thiazole-4-carbonyl)-3-aza-bicyclo[3.3.0]oct-2-ylmethyl]-benzamide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 3-methyl-benzoic acid.
LC-MS: $t_R$=1.11 min; [M+H]$^+$=488.

Example 20

(1S,2S,5R)—N-[7-Methyl-3-(2-methyl-5-m-tolyl-thiazole-4-carbonyl)-3-aza-bicyclo[3.3.0]oct-2-ylmethyl]-3-trifluoromethoxy-benzamide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 3-(trifluoromethoxy)-benzoic acid
LC-MS: $t_R$=1.17 min; [M+H]$^+$=558.

Example 21

6-Trifluoromethyl-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 6-trifluoromethyl-pyridine-2-carboxylic acid.
LC-MS: $t_R$=1.14 min; [M+H]$^+$=543.

Example 22

6-Methyl-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 6-methyl-pyridine-2-carboxylic acid.
LC-MS: $t_R$=1.14 min; [M+H]$^+$=489.

Example 23

6-Methoxy-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 6-methoxy-pyridine-2-carboxylic acid.
LC-MS: $t_R$=1.13 min; [M+H]$^+$=505.

Example 24

4-Bromo-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 4-bromo-pyridine-2-carboxylic acid.
LC-MS: $t_R$=1.12 min; [M+H]$^+$=555.

Example 25

4-Chloro-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 4-chloro-pyridine-2-carboxylic acid.
LC-MS: $t_R$=1.11 min; [M+H]$^+$=509.

Example 26

4-Methyl-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 4-methyl-pyridine-2-carboxylic acid.
LC-MS: $t_R$=1.07 min; [M+H]$^+$=489.

Example 27

(1S,2S,5R)-5-Bromo-N-[7-Methyl-3-(2-methyl-5-m-tolyl-thiazole-4-carbonyl)-3-aza-bicyclo[3.3.0]oct-2-ylmethyl]-nicotinamide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 5-bromo-nicotinic acid.
LC-MS: $t_R$=1.12 min; [M+H]$^+$=555.

Example 28

(1S,2S,5R)-5-Chloro-N-[7-Methyl-3-(2-methyl-5-m-tolyl-thiazole-4-carbonyl)-3-aza-bicyclo[3.3.0]oct-2-ylmethyl]-nicotinamide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 5-chloro-nicotinic acid.
LC-MS: $t_R$=1.11 min; [M+H]$^+$=509.

Example 29

(1S,2S,5R)-5-Methyl-N-[7-Methyl-3-(2-methyl-5-m-tolyl-thiazole-4-carbonyl)-3-aza-bicyclo[3.3.0]oct-2-ylmethyl]-nicotinamide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 5-methyl-nicotinic acid.
LC-MS: $t_R$=0.94 min; [M+H]$^+$=489.

Example 30

Benzofuran-4-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with benzofuran-4-carboxylic acid (M. A. Eissenstat et al. *J. Med. Chem.* 1995, 38, 3094-3105).
LC-MS: $t_R$=1.12 min; [M+H]$^+$=514.

Example 31

2-Methyl-benzofuran-4-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 2-methyl-benzofuran-4-carboxylic acid which was synthesised by saponification of the corresponding methyl ester derivative (Ishikawa T. et al. *Heterocycles* 1994, 39, 1, 371-380) with NaOH in a mixture water/MeOH.
LC-MS: $t_R$=1.14 min; [M+H]$^+$=528.

Example 32

2-Methyl-benzoxazole-4-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide prepared by reaction of [(1S,2S,5R)-2-aminomethyl-7-methyl-3-aza-bicyclo[3.3.0]oct-3-yl]-(2-methyl-5-m-tolyl-thiazol-4-yl)-methanone with 2-methyl-benzoxazole-4-carboxylic acid which was synthesised by saponification of the corresponding methyl ester derivative (Goldstein S et al. *J. of Heterocyclic. Chem.* 1990, 27, 2, 335-336) with NaOH in a mixture water/MeOH.
LC-MS: $t_R$=1.12 min; [M+H]$^+$=529.

Preparation of Examples

General Procedure I

The compounds of the following examples have been prepared using general procedure I described above.

Example 33

6-Methyl-imidazo[2,1-b]thiazole-5-carboxylic acid-(1S,2S,5R)-{3-[5-(3-methoxy-phenyl)-2-methyl-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 5-(3-methoxy-phenyl)-2-methyl-thiazole-4-carboxylic acid.
LC-MS: $t_R$=0.88 min; [M+H]$^+$=536.

Example 34

6-Methyl-imidazo[2,1-b]thiazole-5-carboxylic acid-(1S,2S,5R)-{3-[5-(3-methoxy-phenyl)-2-methyl-thiazole-4-carbonyl]-7-methyl-3-aza-bicyclo[3.3.0]oct-2-ylmethyl}-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 5-(3-methoxy-phenyl)-2-methyl-thiazole-4-carboxylic acid.
LC-MS: $t_R$=0.92 min; [M+H]$^+$=550.

Example 35

6-Methyl-imidazo[2,1-b]thiazole-5-carboxylic acid-(1S,2S,5R)-{3-[2-methyl-5-(3-trifluoromethyl-phenyl)-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 2-methyl-5-(3-trifluoromethyl-phenyl)-thiazole-4-carboxylic acid.
LC-MS: $t_R$=0.94 min; [M+H]$^+$=574.

Example 36

6-Methyl-imidazo[2,1-b]thiazole-5-carboxylic acid-(1S,2S,5R)-{7-methyl-3-[2-methyl-5-(3-trifluoromethyl-phenyl)-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 2-methyl-5-(3-trifluoromethyl-phenyl)thiazole-4-carboxylic acid.
LC-MS: $t_R$=0.97 min; [M+H]$^+$=588.

Example 37

6-Methyl-imidazo[2,1-b]thiazole-5-carboxylic acid-(1S,2S,5R)-{3-[5-(3-fluoro-phenyl)-2-methyl-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 5-(3-fluoro-phenyl)-2-methyl-thiazole-4-carboxylic acid.
LC-MS: $t_R$=0.89 min; [M+H]$^+$=524.

Example 38

6-Methyl-imidazo[2,1-b]thiazole-5-carboxylic acid-(1S,2S,5R)-{3-[5-(3-fluoro-phenyl)-2-methyl-thiazole-4-carbonyl]-7-methyl-3-aza-bicyclo[3.3.0]oct-2-ylmethyl}-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 5-(3-fluoro-phenyl)-2-methyl-thiazole-4-carboxylic acid.
LC-MS: $t_R$=0.93 min; [M+H]$^+$=538.

Example 39

6-Methyl-imidazo[2,1-b]thiazole-5-carboxylic acid-(1S,2S,5R)-[7-methyl-3-(2-methyl-5-p-tolyl-thiazole-4-carbonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 2-methyl-5-p-tolyl-thiazole-4-carboxylic acid.

LC-MS: $t_R$=0.96 min; [M+H]$^+$=534.

Example 40

6-Methyl-imidazo[2,1-b]thiazole-5-carboxylic acid-(1S,2S,5R)-[3-(2-methyl-5-p-tolyl-thiazole-4-carbonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 2-methyl-5-p-tolyl-thiazole-4-carboxylic acid.

LC-MS: $t_R$=0.91 min; [M+H]$^+$=520.

Example 41

6-Methyl-imidazo[2,1-b]thiazole-5-carboxylic acid-(1S,2S,5R)-{3-[5-(3-chloro-phenyl)-2-methyl-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 5-(3-chloro-phenyl)-2-methyl-thiazole-4-carboxylic acid.

LC-MS: $t_R$=0.92 min; [M+H]$^+$=540.

Example 42

6-Methyl-imidazo[2,1-b]thiazole-5-carboxylic acid-(1S,2S,5R)-{3-[5-(3-chloro-phenyl)-2-methyl-thiazole-4-carbonyl]-7-methyl-3-aza-bicyclo[3.3.0]oct-2-ylmethyl}-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 5-(3-chloro-phenyl)-2-methyl-thiazole-4-carboxylic acid.

LC-MS: $t_R$=0.95 min; [M+H]$^+$=554.

Example 43

6-Methyl-imidazo[2,1-b]thiazole-5-carboxylic acid-(1S,2S,5R)-{3-[5-(4-methoxy-phenyl)-2-methyl-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 5-(4-methoxy-phenyl)-2-methyl-thiazole-4-carboxylic acid.

LC-MS: $t_R$=0.88 min; [M+H]$^+$=536.

Example 44

6-Methyl-imidazo[2,1-b]thiazole-5-carboxylic acid-(1S,2S,5R)-{3-[5-(4-methoxy-phenyl)-2-methyl-thiazole-4-carbonyl]-7-methyl-3-aza-bicyclo[3.3.0]oct-2-ylmethyl}-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 5-(4-methoxy-phenyl)-2-methyl-thiazole-4-carboxylic acid.

LC-MS: $t_R$=0.91 min; [M+H]$^+$=550.

Example 45

6-Methyl-imidazo[2,1-b]thiazole-5-carboxylic acid-(1S,2S,5R)-{3-[5-(4-ethyl-phenyl)-2-methyl-thiazole-4-carbonyl]-7-methyl-3-aza-bicyclo[3.3.0]oct-2-ylmethyl}-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 5-(4-ethyl-phenyl)-2-methyl-thiazole-4-carboxylic acid.

LC-MS: $t_R$=0.99 min; [M+H]$^+$=548.

Example 46

6-Methyl-imidazo[2,1-b]thiazole-5-carboxylic acid-(1S,2S,5R)-{7-methyl-3-[2-methyl-5-(4-trifluoromethyl-phenyl)-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 2-methyl-5-(4-trifluoromethyl-phenyl)thiazole-4-carboxylic acid.

LC-MS: $t_R$=0.98 min; [M+H]$^+$=588.

Example 47

6-Methyl-imidazo[2,1-b]thiazole-5-carboxylic acid-(1S,2S,5R)-{3-[5-(4-fluoro-phenyl)-2-methyl-thiazole-4-carbonyl]-7-methyl-3-aza-bicyclo[3.3.0]oct-2-ylmethyl}-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 5-(4-fluoro-phenyl)-2-methyl-thiazole-4-carboxylic acid.

LC-MS: $t_R$=0.93 min; [M+H]$^+$=538.

Example 48

6-Methyl-imidazo[2,1-b]thiazole-5-carboxylic acid-(1S,2S,5R)-{7-methyl-3-[2-methyl-5-phenyl-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 2-methyl-5-phenyl-thiazole-4-carboxylic acid.

LC-MS: $t_R$=0.92 min; [M+H]$^+$=520.

Example 49

6-Methyl-imidazo[2,1-b]thiazole-5-carboxylic acid-
(1S,2S,5R)-{3-[5-(3,4-dimethyl-phenyl)-2-methyl-
thiazole-4-carbonyl]-7-methyl-3-aza-bicyclo[3.3.0]
oct-2-ylmethyl}-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 5-(3,4-dimethyl-phenyl)-2-methyl-thiazole-4-carboxylic acid.
LC-MS: $t_R$=0.98 min; [M+H]$^+$=548.

Example 50

6-Methyl-imidazo[2,1-b]thiazole-5-carboxylic acid-
(1S,2S,5R)-{3-[5-(3,4-dimethyl-phenyl)-2-methyl-
thiazole-4-carbonyl]-3-aza-bicyclo[3.3.0]oct-2-ylm-
ethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 5-(3,4-dimethyl-phenyl)-2-methyl-thiazole-4-carboxylic acid.
LC-MS: $t_R$=0.94 min; [M+H]$^+$=534.

Example 51

6-Methyl-imidazo[2,1-b]thiazole-5-carboxylic acid-
(1S,2S,5R)-{3-[5-(3,4-difluoro-phenyl)-2-methyl-
thiazole-4-carbonyl]-7-methyl-3-aza-bicyclo[3.3.0]
oct-2-ylmethyl}-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 5-(3,4-difluoro-phenyl)-2-methyl-thiazole-4-carboxylic acid.
LC-MS: $t_R$=0.94 min; [M+H]$^+$=556.

Example 52

6-Methyl-imidazo[2,1-b]thiazole-5-carboxylic acid-
(1S,2S,5R)-{3-[5-(3,4-difluoro-phenyl)-2-methyl-
thiazole-4-carbonyl]-3-aza-bicyclo[3.3.0]oct-2-ylm-
ethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 5-(3,4-difluoro-phenyl)-2-methyl-thiazole-4-carboxylic acid.
LC-MS: $t_R$=0.90 min; [M+H]$^+$=542.

Example 53

6-Methyl-imidazo[2,1-b]thiazole-5-carboxylic acid-
(1S,2S,5R)-[3-(2-amino-5-phenyl-thiazole-4-carbo-
nyl)-7-methyl-3-aza-bicyclo[3.3.0]oct-2-ylmethyl]-
amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 2-amino-5-phenyl-thiazole-4-carboxylic acid.
LC-MS: $t_R$=0.84 min; [M+H]$^+$=521.

Example 54

6-Methyl-imidazo[2,1-b]thiazole-5-carboxylic acid-
(1S,2S,5R)-[3-(biphenyl-2-carbonyl)-7-methyl-3-
aza-bicyclo[3.3.0]oct-2-ylmethyl]-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with commercially available biphenyl-2-carboxylic acid.
LC-MS: $t_R$=0.96 and 1.01 min; [M+H]$^+$=499.

Example 55

6-Methyl-imidazo[2,1-b]thiazole-5-carboxylic acid-
(1S,2S,5R)-[7-methyl-3-(3'-methyl-biphenyl-2-car-
bonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with commercially available 3'-methyl-biphenyl-2-carboxylic acid.
LC-MS: $t_R$=0.98 and 1.04 min; [M+H]$^+$=512.

Example 56

6-Methyl-imidazo[2,1-b]thiazole-5-carboxylic acid-
(1S,2S,5R)-[7-methyl-3-(4'-methyl-biphenyl-2-car-
bonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with commercially available 4'-methyl-biphenyl-2-carboxylic acid.
LC-MS: $t_R$=0.99 and 1.05 min; [M+H]$^+$=512.

Example 57

6-Methyl-imidazo[2,1-b]thiazole-5-carboxylic acid-
(1S,2S,5R)-[7-methyl-3-(4'-fluoro-biphenyl-2-carbo-
nyl)-3-aza-bicyclo[3.3.0]oct-2-ylmethyl]-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with commercially available 4'-fluoro-biphenyl-2-carboxylic acid.
LC-MS: $t_R$=0.96 and 1.01 min; [M+H]$^+$=517.

Example 58

6-Methyl-imidazo[2,1-b]thiazole-5-carboxylic acid-
(1S,2S,5R)-[7-methyl-3-(3'-methoxy-biphenyl-2-
carbonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with commercially available 3'-methoxy-biphenyl-2-carboxylic acid.
LC-MS: $t_R$=0.95 and 1.01 min; [M+H]$^+$=529.

Example 59

6-Methyl-imidazo[2,1-b]thiazole-5-carboxylic acid-(1S,2S,5R)-[7-methyl-3-(4'-chloro-biphenyl-2-carbonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with commercially available 4'-chloro-biphenyl-2-carboxylic acid.
LC-MS: $t_R$=1.00 and 1.05 min; $[M+H]^+$=533.

Example 60

6-Methyl-imidazo[2,1-b]thiazole-5-carboxylic acid-(1S,2S,5R)-[3-(biphenyl-2-carbonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-3-aza-bicyclo[3.3.0]oct-2-ylmethyl]-amide with commercially available biphenyl-2-carboxylic acid.
LC-MS: $t_R$=0.94 min; $[M+H]^+$=485.

Example 61

6-Methyl-imidazo[2,1-b]thiazole-5-carboxylic acid-(1S,2S,5R)-[3-(4'-fluoro-biphenyl-2-carbonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-3-aza-bicyclo[3.3.0]oct-2-ylmethyl]-amide with commercially available 4'-fluoro-biphenyl-2-carboxylic acid.
LC-MS: $t_R$=0.94 min; $[M+H]^+$=485.

Example 62

6-Methyl-imidazo[2,1-b]thiazole-5-carboxylic acid-(1S,2S,5R)-[3-(3'-methyl-biphenyl-2-carbonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-3-aza-bicyclo[3.3.0]oct-2-ylmethyl]-amide with commercially available 3'-methyl-biphenyl-2-carboxylic acid.
LC-MS: $t_R$=0.97 min.; $[M+H]^+$=499.

Example 63

6-Methyl-imidazo[2,1-b]thiazole-5-carboxylic acid-(1S,2S,5R)-[3-(3'-methoxy-biphenyl-2-carbonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-3-aza-bicyclo[3.3.0]oct-2-ylmethyl]-amide with commercially available 3'-methoxy-biphenyl-2-carboxylic acid.
LC-MS: $t_R$=0.94 and 1.01 min; $[M+H]^+$=515.

Example 64

6-Methyl-imidazo[2,1-b]thiazole-5-carboxylic acid-(1S,2S,5R)-[3-(2-methyl-5-phenyl-thiazole-4-carbonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-3-aza-bicyclo[3.3.0]oct-2-ylmethyl]-amide with commercially available 2-methyl-5-phenyl-thiazole-4-carboxylic acid.
LC-MS: $t_R$=0.88 min; $[M+H]^+$=506.

Example 65

6-Methyl-imidazo[2,1-b]thiazole-5-carboxylic acid-(1S,2S,5R)-{3-[5-(4-fluoro-phenyl)-2-methyl-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 5-(4-fluoro-phenyl)-2-methyl-thiazole-4-carboxylic acid.
LC-MS: $t_R$=0.89 min; $[M+H]^+$=524.

Example 66

6-Methyl-imidazo[2,1-b]thiazole-5-carboxylic acid-(1S,2S,5R)-{3-[5-(4-ethyl-phenyl)-2-methyl-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 5-(4-ethyl-phenyl)-2-methyl-thiazole-4-carboxylic acid.
LC-MS: $t_R$=0.95 min; $[M+H]^+$=534.

Example 67

6-Methyl-imidazo[2,1-b]thiazole-5-carboxylic acid-(1S,2S,5R)-{3-[5-(4-chloro-phenyl)-2-methyl-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 5-(4-chloro-phenyl)-2-methyl-thiazole-4-carboxylic acid.
LC-MS: $t_R$=0.92 min; $[M+H]^+$=540.

Example 68

6-Methyl-imidazo[2,1-b]thiazole-5-carboxylic acid-(1S,2S,5R)-{3-[2-methyl-5-(4-trifluoromethyl-phenyl)-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 2-methyl-5-(4-trifluoromethyl-phenyl)-thiazole-4-carboxylic acid.
LC-MS: $t_R$=0.95 min; $[M+H]^+$=574.

Example 69

6-Methyl-imidazo[2,1-b]thiazole-5-carboxylic acid-(1S,2S,5R)-{3-[2-amino-5-(3-methyl-phenyl)-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 2-amino-5-(3-methyl-phenyl)-thiazole-4-carboxylic acid.
LC-MS: $t_R$=0.83 min; $[M+H]^+$=521.

Example 70

6-Methyl-imidazo[2,1-b]thiazole-5-carboxylic acid-(1S,2S,5R)-{3-[2-amino-5-(3-fluoro-phenyl)-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 2-amino-5-(3-fluoro-phenyl)-thiazole-4-carboxylic acid.
LC-MS: $t_R$=0.82 min; [M+H]$^+$=525.

Example 71

6-Methyl-imidazo[2,1-b]thiazole-5-carboxylic acid-(1S,2S,5R)-[3-(2-amino-5-phenyl-thiazole-4-carbonyl)-3-aza-bicyclo[3.3.0]oct-2-ylmethyl]-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 2-amino-5-phenyl-thiazole-4-carboxylic acid.
LC-MS: $t_R$=0.80 min; [M+H]$^+$=507.

Example 72

6-Methyl-imidazo[2,1-b]thiazole-5-carboxylic acid-(1S,2S,5R)-{7-methyl-3-[2-amino-5-(3-methyl-phenyl)-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-7-methyl-3-aza-bicyclo[3.3.0]oct-2-ylmethyl]-amide with 2-amino-5-(3-methyl-phenyl)-thiazole-4-carboxylic acid.
LC-MS: $t_R$=0.86 min; [M+H]$^+$=535.

Example 73

6-Methyl-imidazo[2,1-b]thiazole-5-carboxylic acid-(1S,2S,5R)-{7-methyl-3-[2-amino-5-(4-fluoro-phenyl)-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 2-amino-5-(4-fluoro-phenyl)-thiazole-4-carboxylic acid.
LC-MS: $t_R$=0.85 min; [M+H]$^+$=539.

Example 74

6-Methyl-imidazo[2,1-b]thiazole-5-carboxylic acid-(1S,2S,5R)-{7-methyl-3-[2-amino-5-(3-fluoro-phenyl)-thiazole-4-carbonyl]-3-aza-bicyclo[3.3.0]oct-2-ylmethyl}-amide prepared by reaction of 6-methyl-imidazo[2,1-b]thiazole-5-carboxylic acid-[(1S,2S,5R)-3-aza-bicyclo[3.3.0]oct-2-ylmethyl]-amide with 2-amino-5-(3-fluoro-phenyl)-thiazole-4-carboxylic acid.
LC-MS: $t_R$=0.86 min; [M+H]$^+$=539.

Example 75

Imidazo[2,1-b]thiazole-6-carboxylic acid-(1S,2S,5R)-[3-(2-methyl-5-m-tolyl-thiazole-4-carbonyl)-3-aza-bicyclo[3.3.0]oct-2-ylmethyl]-amide prepared by reaction of imidazo[2,1-b]thiazole-6-carboxylic acid-[(1S,2S,5R)-3-aza-bicyclo[3.3.0]oct-2-ylmethyl]-amide with 2-methyl-5-m-tolyl-thiazole-4-carboxylic acid.
LC-MS: $t_R$=0.95 min; [M+H]$^+$=506.

Preparation of Examples

General Procedure II

The compound of the following example has been prepared using general procedure II described above.

Example 76

(1S,2S,5R)-2-Methyl-N-[7-Methyl-3-(2-methyl-5-m-tolyl-thiazole-4-carbonyl)-3-aza-bicyclo[3.3.0]oct-2-ylmethyl]-isonicotinamide prepared by reaction of [(1S,2S,5R)-2-aminomethyl-7-methyl-3-aza-bicyclo[3.3.0]oct-2-yl]-(2-methyl-5-m-tolyl-thiazol-4-yl)-methanone with 2-methyl-isonicotinic acid.
LC-MS: $t_R$=0.90 min; [M+H]$^+$=489.

Example 77

2-Methyl-benzofuran-4-carboxylic acid-(1S,2S,5R)-[7,7-difluoro-3-(2-methyl-5-m-tolyl-thiazole-4-carbonyl)-3-aza-bicyclo[3.3.0]oct-3-ylmethyl]-amide prepared by reaction of (1S,2S,5R)-(2-aminomethyl-7,7-difluoro-3-aza-bicyclo[3.3.0]-oct-3-yl)-(2-methyl-5-m-tolyl-thiazol-4-yl)-methanone with 2-methyl-benzofuran-4-carboxylic acid (prepared according to scheme 15).
LC-MS: $t_R$=1.05 min; [M+H]$^+$=550.09

Example 78

3-Methyl-benzofuran-4-carboxylic acid-(1S,2S,5R)-[7,7-difluoro-3-(2-methyl-5-m-tolyl-thiazole-4-carbonyl)-3-aza-bicyclo[3.3.0]oct-3-ylmethyl]-amide prepared by reaction of (1S,2S,5R)-(2-aminomethyl-7,7-difluoro-3-aza-bicyclo[3.3.0]-oct-3-yl)-(2-methyl-5-m-tolyl-thiazol-4-yl)-methanone with 3-methyl-benzofuran-4-carboxylic acid (prepared according to scheme 14).
LC-MS: $t_R$=1.03 min; [M+H]$^+$=550.05

Example 79

2,3-Dihydro-benzofuran-4-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide prepared by reaction of (1S,2S,5R)-(2-aminomethyl-7,7-difluoro-3-aza-bicyclo[3.3.0]-oct-3-yl)-(2-methyl-5-m-tolyl-thiazol-4-yl)-methanone with 2,3-dihydro-benzofuran-4-carboxylic acid.
LC-MS: $t_R$=1.01 min; [M+H]$^+$=537.99

Example 80

2,3-Dihydro-benzo[1,4]dioxine-5-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide prepared by reaction of (1S,2S,5R)-(2-aminomethyl-7,7-difluoro-3-aza-bicyclo[3.3.0]-oct-3-yl)-(2-methyl-5-m-tolyl-thiazol-4-yl)-methanone with 2,3-dihydro-benzo[1,4]dioxine-5-carboxylic acid.

LC-MS: $t_R$=1.00 min; [M+H]$^+$=553.97

Example 81

Benzothiazole-7-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide prepared by reaction of (1S,2S,5R)-(2-aminomethyl-7,7-difluoro-3-aza-bicyclo[3.3.0]-oct-3-yl)-(2-methyl-5-m-tolyl-thiazol-4-yl)-methanone with benzothiazole-7-carboxylic acid (prepared according to scheme 13).

LC-MS: $t_R$=1.02 min; [M+H]$^+$=553.07

Example 82

6-Methyl-pyrrolo[2,1-b]thiazole-7-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide prepared by reaction of (1S,2S,5R)-(2-aminomethyl-7,7-difluoro-3-aza-bicyclo[3.3.0]-oct-3-yl)-(2-methyl-5-m-tolyl-thiazol-4-yl)-methanone with 6-methyl-pyrrolo[2,1-b]thiazole-7-carboxylic acid (prepared according to scheme 12).

LC-MS: $t_R$=0.99 min; [M+H]$^+$=554.86

Example 83

Imidazo[1,2-a]pyridine-3-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide prepared by reaction of (1S,2S,5R)-(2-aminomethyl-7,7-difluoro-3-aza-bicyclo[3.3.0]-oct-3-yl)-(2-methyl-5-m-tolyl-thiazol-4-yl)-methanone with imidazo[1,2-a]pyridine-3-carboxylic acid.

LC-MS: $t_R$=0.89 min; [M+H]$^+$=536.06

Example 84

1-Methyl-1H-indazole-3-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide prepared by reaction of (1S,2S,5R)-(2-aminomethyl-7,7-difluoro-3-aza-bicyclo[3.3.0]-oct-3-yl)-(2-methyl-5-m-tolyl-thiazol-4-yl)-methanone with 1-methyl-1H-indazole-3-carboxylic acid.

LC-MS: $t_R$=1.02 min; [M+H]$^+$=550.12

Example 85

6-Methyl-imidazo[2,1-b]-thiazole-5-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide prepared by reaction of (1S,2S,5R)-(2-aminomethyl-7,7-difluoro-3-aza-bicyclo[3.3.0]-oct-3-yl)-(2-methyl-5-m-tolyl-thiazol-4-yl)-methanone with 6-methyl-imidazo[2,1-b]thiazole-5-carboxylic acid.

LC-MS: $t_R$=0.89 min; [M+H]$^+$=556.04

II. Biological Assays

In Vitro Assay

The orexin receptor antagonistic activity of the compounds of formula (I) is determined in accordance with the following experimental method.

Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% heat inactivated fetal calf serum (FCS). The cells are seeded at 20,000 cells/well into 384-well black clear bottom sterile plates (Greiner). The seeded plates are incubated overnight at 37° C. in 5% $CO_2$.

Human orexin-A as an agonist is prepared as 1 mM stock solution in MeOH:water (1:1), diluted in HBSS containing 0.1% bovine serum albumin (BSA), $NaHCO_3$: 0.375 g/l and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), $NaHCO_3$: 0.375 g/l and 20 mM HEPES. On the day of the assay, 50 µl of staining buffer (HBSS containing 1% FCS, 20 mM HEPES, $NaHCO_3$: 0.375 g/l, 5 mM probenecid (Sigma) and 3 µM of the fluorescent calcium indicator fluo-4 AM (1 mM stock solution in DMSO, containing 10% pluronic) is added to each well. The 384-well cell-plates are incubated for 50 min at 37° C. in 5% $CO_2$ followed by equilibration at rt for 30-120 min before measurement.

Within the Fluorescent Imaging Plate Reader (FLIPR2 or FLIPR Tetra, Molecular Devices), antagonists are added to the plate in a volume of 10 Owen, incubated for 10 min and finally 10 µl/well of agonist is added. Fluorescence is measured for each well at 1 second intervals, and the height of each fluorescence peak is compared to the height of the fluorescence peak induced by 3 nM orexin-A with vehicle in place of antagonist. For each antagonist, the $IC_{50}$ value (the concentration of compound needed to inhibit 50% of the agonistic response) is determined. With the FLIPR Tetra, non-optimized and optimized conditions were used. Optimized conditions were achieved by adjustment of pipetting speed and cell splitting regime. The calculated $IC_{50}$ values of the compounds may fluctuate depending on the daily cellular assay performance. Fluctuations of this kind are known to those skilled in the art.

Antagonistic activities ($IC_{50}$ values) of all exemplified compounds are in the range of 2-1640 nM with respect to the $OX_1$ receptor and in the range of 3-2516 nM with respect to the $OX_2$ receptor. Antagonistic activities of selected compounds are displayed in Table 1.

TABLE 1

| Compound of Example | OX$_1$ IC$_{50}$ (nM) | OX$_2$ IC$_{50}$ (nM) |
| --- | --- | --- |
| 6 | 59 | 114 |
| 7 | 12 | 13 |
| 11 | 7 | 9 |
| 19 | 77 | 47 |
| 25 | 24 | 48 |
| 33 | 8[1] | 17[1] |
| 36 | 44[1] | 262[1] |
| 51 | 33[1] | 94[1] |
| 60 | 16[1] | 21[1] |
| 70 | 17[1] | 20[1] |
| 79 | 8[2] | 20[2] |
| 81 | 6[2] | 10[2] |
| 85 | 7[2] | 18[2] |

Values in table 1 are measured using FLIPR2 or using
[1]FLIPR Tetra, non-optimized conditions;
[2]FLIPR Tetra, optimized conditions.

The invention claimed is:
1. A compound of the formula (I)

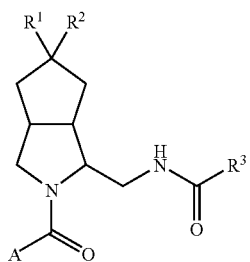
(I)

wherein
R$^1$ represents hydrogen, (C$_{1-4}$)alkyl or fluorine;
R$^2$ represents hydrogen, (C$_{1-4}$)alkyl or fluorine;
R$^3$ represents aryl, which is unsubstituted, mono-, di-, or tri-substituted, wherein the substituents are independently selected from the group consisting of (C$_{1-4}$)alkyl, (C$_{1-4}$)alkoxy, trifluoromethyl, trifluoromethoxy, and halogen;
or heteroaryl, which is unsubstituted, mono-, di-, or tri-substituted, wherein the substituents are independently selected from the group consisting of (C$_{1-4}$)alkyl, (C$_{1-4}$)alkoxy, halogen, and trifluoromethyl;
A represents

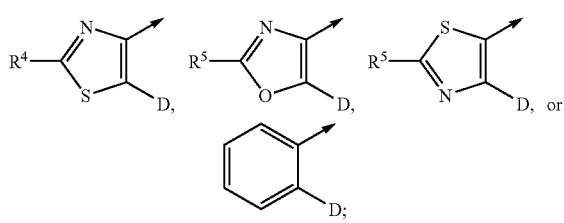

R$^4$ represents (C$_{1-4}$)alkyl, or —NR$^6$R$^7$;
R$^5$ represents (C$_{1-4}$)alkyl;
R$^6$ represents hydrogen, or (C$_{1-4}$)alkyl;
R$^7$ represents hydrogen, or (C$_{1-4}$)alkyl; and
D represents aryl, which is unsubstituted, mono-, di-, or tri-substituted, wherein the substituents are independently selected from the group consisting of (C$_{1-4}$)alkyl, (C$_{1-4}$)alkoxy, trifluoromethyl, and halogen;
or a salt of such a compound, wherein the compound of formula (I) may be present as mixture of stereoisomers or as pure stereoisomer.
2. The compound of formula (I) according to claim 1, wherein
R$^1$ represents hydrogen, or (C$_{1-4}$)alkyl; and
R$^2$ represents hydrogen, or (C$_{1-4}$)alkyl;
or a salt of such a compound.
3. The compound of formula (I) according to claim 1, wherein
A represents

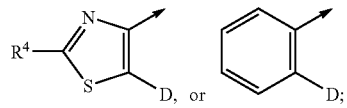

or a salt of such a compound.
4. The compound of formula (I) according to claim 1, wherein
R$^4$ represents methyl, or —NH$_2$;
or a salt of such a compound.
5. The compound according to claim 1, wherein
D represents phenyl, which is unsubstituted, mono-, di-, or tri-substituted, wherein the substituents are independently selected from the group consisting of (C$_{1-4}$)alkyl, (C$_{1-4}$)alkoxy, trifluoromethyl, and halogen;
or a salt of such a compound.
6. The compound according to claim 1, wherein
R$^3$ represents phenyl, which is unsubstituted, mono-, di-, or tri-substituted, wherein the substituents are independently selected from the group consisting of (C$_{1-4}$)alkyl, (C$_{1-4}$)alkoxy, trifluoromethyl, trifluoromethoxy, and halogen; 2,3-dihydro-benzofuranyl; benzo[1,3]dioxolyl; 2,3-dihydro-benzo[1,4]dioxinyl; 4H-benzo[1,3]dioxinyl; or an isoxazolyl, a pyridyl, an indazolyl, a benzofuranyl, a benzoxazolyl, a benzisoxazolyl, a benzoisothiazolyl, or an imidazo[2,1-b]thiazolyl group, wherein said groups are unsubstituted, mono-, di-, or tri-substituted, wherein the substituents are independently selected from the group consisting of (C$_{1-4}$)alkyl, (C$_{1-4}$)alkoxy, halogen, and trifluoromethyl;
or a salt of such a compound.
7. The compound according to claim 1 selected from the group consisting of
2,3-Dihydro-benzo[1,4]dioxine-5-carboxylic acid-(1S,2S,5R)-[3-(2-methyl-5-m-tolyl-thiazole-4-carbonyl)-3-aza-bicyclo[3.3.0]oct-2-ylmethyl]-amide;
Benzo[d]isothiazole-3-carboxylic acid-(1S,2S,5R)-[3-(2-methyl-5-m-tolyl-thiazole-4-carbonyl)-3-aza-bicyclo[3.3.0]oct-2-ylmethyl]-amide;
(1S,2S,5R)-3-Bromo-N-[7-methyl-3-(2-methyl-5-m-tolyl-thiazole-4-carbonyl)-3-aza-bicyclo[3.3.0]oct-2-ylmethyl]-benzamide;
(1S,2S,5R)-3-Chloro-N-[7-methyl-3-(2-methyl-5-m-tolyl-thiazole-4-carbonyl)-3-aza-bicyclo[3.3.0]oct-2-ylmethyl]-benzamide;
(1S,2S,5R)-3-Fluoro-N-[7-methyl-3-(2-methyl-5-m-tolyl-thiazole-4-carbonyl)-3-aza-bicyclo[3.3.0]oct-2-ylmethyl]-benzamide;
(1S,2S,5R)-3-Methoxy-N-[7-methyl-3-(2-methyl-5-m-tolyl-thiazole-4-carbonyl)-3-aza-bicyclo[3.3.0]oct-2-ylmethyl]-benzamide;
(1S,2S,5R)—N-[7-methyl-3-(2-methyl-5-m-tolyl-thiazole-4-carbonyl)-3-aza-bicyclo[3.3.0]oct-2-ylmethyl]-3-trifluoromethyl-benzamide;

(1S,2S,5R)-3-Methyl-N-[7-methyl-3-(2-methyl-5-m-tolyl-thiazole-4-carbonyl)-3-aza-bicyclo[3.3.0]oct-2-ylmethyl]-benzamide;
(1S,2S,5R)—N-[7-methyl-3-(2-methyl-5-m-tolyl-thiazole-4-carbonyl)-3-aza-bicyclo[3.3.0]oct-2-ylmethyl]-3-trifluoromethoxy-benzamide;
6-Trifluoromethyl-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
6-Methoxy-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
4-Bromo-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
4-Chloro-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
4-Methyl-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
(1S,2S,5R)-5-Bromo-N-[7-methyl-3-(2-methyl-5-m-tolyl-thiazole-4-carbonyl)-3-aza-bicyclo[3.3.0]oct-2-ylmethyl]-nicotinamide;
(1S,2S,5R)-5-Chloro-N-[7-methyl-3-(2-methyl-5-m-tolyl-thiazole-4-carbonyl)-3-aza-bicyclo[3.3.0]oct-2-ylmethyl]-nicotinamide;
(1S,2S,5R)-5-Methyl-N-[7-methyl-3-(2-methyl-5-m-tolyl-thiazole-4-carbonyl)-3-aza-bicyclo[3.3.0]oct-2-ylmethyl]-nicotinamide;
Benzofuran-4-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
2-Methyl-benzofuran-4-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
2-Methyl-benzoxazole-4-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
2,3-Dihydro-benzo[1,4]dioxine-5-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
1-Methyl-indazole-3-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
3,5-Dimethyl-isoxazole-4-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
Benzo[d]isoxazole-3-carboxylic acid-(1S,2S,5R)-[7-methyl-3-(2-methyl-5-m-tolyl-thiazole-4-carbonyl)-3-aza-bicyclo[3.3.0]oct-2-ylmethy]-amide;
(1S,2S,5R)-2-Methyl-N-[7-methyl-3-(2-methyl-5-m-tolyl-thiazole-4-carbonyl)-3-aza-bicyclo[3.3.0]oct-2-ylmethyl]-isonicotinamide;
Benzo[d]isoxazole-3-carboxylic acid-(1S,2S,5R)-[3-(2-methyl-5-m-tolyl-thiazole-4-carbonyl)-3-aza-bicyclo[3.3.0]oct-2-ylmethyl]-amide; and
Benzo[d]isothiazole-3-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
or a salt of such a compound.

8. A pharmaceutical composition containing, as active principle, a compound of formula (I) according to claim 1, or a pharmaceutically acceptable salt thereof, and at least one therapeutically inert excipient.

9. The pharmaceutical composition according to claim 8 which further comprises a pharmaceutically acceptable carrier material.

10. A method for the treatment of diseases selected from the group consisting of all types of sleep disorders, of stress-related syndromes, of psychoactive substance use, abuse, seeking and reinstatement, and of eating or drinking disorders comprising administering to a subject a pharmaceutically active amount of a compound according to claim 1 in free base form or pharmaceutically acceptable salt form.

11. The compound of formula (I) according to claim 1, wherein the configuration of the 3-aza-bicyclo[3.3.0]octane moiety is such that the —CH$_2$—NH—CO—R$^3$ substituent and the cyclopentane ring of the 3-aza-bicyclo[3.3.0]octane moiety are in trans relation;

or a salt thereof.

12. The compound of formula (I) according to claim 1, which is also a compound of formula (I$_{E1}$); wherein the absolute configuration of the carbon center of the 3-aza-bicyclo[3.3.0]octane moiety to which the —CH$_2$—NH—CO—R$^3$ group is attached is (2S):

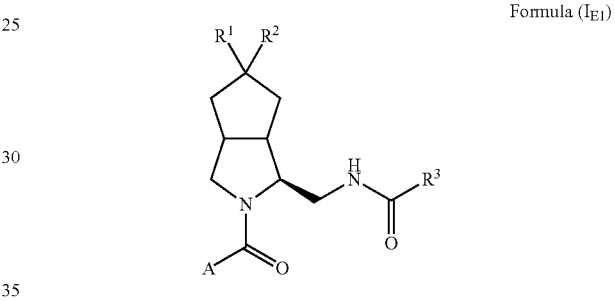

Formula (I$_{E1}$)

or a salt thereof.

13. The compound of formula (I) according to claim 11, wherein the absolute configuration is as depicted in formula (I$_{E2}$)

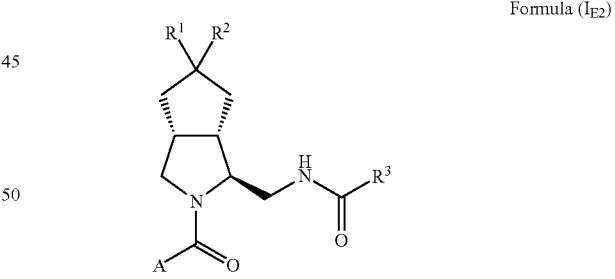

Formula (I$_{E2}$)

or a salt thereof.

14. The compound according to claim 1 selected from the group consisting of:
Imidazo[2,1-b]thiazole-5-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
Imidazo[2,1-b]thiazole-5-carboxylic acid-(1S,2S,5R)-[3-(2-methyl-5-m-tolyl-thiazole-4-carbonyl)-3-aza-bicyclo[3.3.0]oct-2-ylmethyl]-amide;
Imidazo[2,1-b]thiazole-6-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;

6-Methyl-imidazo[2,1-b]thiazole-5-carboxylic acid-(1S, 2S,5R)-[3-(2-methyl-5-m-tolyl-thiazole-4-carbonyl)-3-aza-bicyclo[3.3.0]oct-2-ylmethyl]-amide;
6-Methyl-pyridine-2-carboxylic acid-(1S,2S,5R)-[7-methyl-3-(2-methyl-5-m-tolyl-thiazole-4-carbonyl)-3-aza-bicyclo[3.3.0]oct-2-ylmethyl]-amide;
6-Methyl-imidazo[2,1-b]thiazole-5-carboxylic acid-(1S, 2S,5R)-[7-methyl-3-(2-methyl-5-m-tolyl-thiazole-4-carbonyl)-3-aza-bicyclo[3.3.0]oct-2-ylmethyl]-amide;
6-Methyl-imidazo[2,1-b]thiazole-5-carboxylic acid-(1S, 2S,5R)-{3-[5-(3-methoxy-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-{3-[5-(3-methoxy-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S, 2S,5R)-{3-[2-methyl-5-(3-trifluoromethyl-phenyl)-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-{7-methyl-3-[2-methyl-5-(3-trifluoromethyl-phenyl)-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-{3-[5-(3-fluoro-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-{3-[5-(3-fluoro-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S, 2S,5R)-[7-methyl-3-(2-methyl-5-p-tolyl-thiazole-4-carbonyl)-3-aza-bicyclo[3.3.0]oct-2-ylmethyl]-amide;
6-Methyl-imidazo[2,1-b]thiazole-5-carboxylic acid-(1S, 2S,5R)-[3-(2-methyl-5-p-tolyl-thiazole-4-carbonyl)-3-aza-bicyclo[3.3.0]oct-2-ylmethyl]-amide;
6-Methyl-imidazo[2,1-b]thiazole-5-carboxylic acid-(1S, 2S,5R)-{3-[5-(3-chloro-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-{3-[5-(3-chloro-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S, 2S,5R)-{3-[5-(4-methoxy-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-{3-[5-(4-methoxy-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S, 2S,5R)-{3-[5-(4-ethyl-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S, 2S,5R)-{7-methyl-3-[2-methyl-5-(4-trifluoromethyl-phenyl)-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-{3-[5-(4-fluoro-phenyl)-2-methyl-thiazole-4-carbonyl]-7-methyl-3-aza-bicyclo[3.3.0]oct-2-ylmethyl}-amide;
6-Methyl-imidazo[2,1-b]-thiazole-5-carboxylic acid-(1S, 2S,5R)-{7-methyl-3-[2-methyl-5-phenyl-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-{3-[5-(3,4-dimethyl-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S, 2S,5R)-{3-[5-(3,4-dimethyl-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-{3-[5-(3,4-difluoro-phenyl)-2-methyl-thiazole-4-carbonyl]-7-methyl-3-aza-bicyclo[3.3.0]oct-2-ylmethyl}-amide;
6-Methyl-imidazo[2,1-b]thiazole-5-carboxylic acid-(1S, 2S,5R)-{3-[5-(3,4-difluoro-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-[3-(2-amino-5-phenyl-thiazole-4-carbonyl)-7-methyl-3-aza-bicyclo[3.3.0]oct-2-ylmethyl]-amide;
6-Methyl-imidazo[2,1-b]thiazole-5-carboxylic acid-(1S, 2S,5R)-[3-(biphenyl-2-carbonyl)-7-methyl-3-aza-bicyclo[3.3.0]oct-2-ylmethyl]-amide;
6-Methyl-imidazo[2,1-b]thiazole-5-carboxylic acid-(1S, 2S,5R)-[7-methyl-3-(3'-methyl-biphenyl-2-carbonyl)-3-aza-bicyclo[3.3.0]oct-2-ylmethyl]-amide;
6-Methyl-imidazo[2,1-b]-thiazole-5-carboxylic acid-(1S, 2S,5R)-[7-methyl-3-(4'-methyl-biphenyl-2-carbonyl)-3-aza-bicyclo[3.3.0]oct-2-ylmethyl]-amide;
6-Methyl-imidazo[2,1-b]-thiazole-5-carboxylic acid-(1S, 2S,5R)-[7-methyl-3-(4'-fluoro-biphenyl-2-carbonyl)-3-aza-bicyclo[3.3.0]oct-2-ylmethyl]-amide;
6-Methyl-imidazo[2,1-b]-thiazole-5-carboxylic acid-(1S, 2S,5R)-[7-methyl-3-(3'-methoxy-biphenyl-2-carbonyl)-3-aza-bicyclo[3.3.0]oct-2-ylmethyl]-amide;
6-Methyl-imidazo[2,1-b]-thiazole-5-carboxylic acid-(1S, 2S,5R)-[7-methyl-3-(4'-chloro-biphenyl-2-carbonyl)-3-aza-bicyclo[3.3.0]oct-2-ylmethyl]-amide;
6-Methyl-imidazo[2,1-b]thiazole-5-carboxylic acid-(1S, 2S,5R)-[3-(biphenyl-2-carbonyl)-3-aza-bicyclo[3.3.0]oct-2-ylmethyl]-amide;
6-Methyl-imidazo[2,1-b]-thiazole-5-carboxylic acid-(1S, 2S,5R)-[3-(4'-fluoro-biphenyl-2-carbonyl)-3-aza-bicyclo[3.3.0]oct-2-ylmethyl]-amide;
6-Methyl-imidazo[2,1-b]-thiazole-5-carboxylic acid-(1S, 2S,5R)-[3-(3'-methyl-biphenyl-2-carbonyl)-3-aza-bicyclo[3.3.0]oct-2-ylmethyl]-amide;
6-Methyl-imidazo[2,1-b]-thiazole-5-carboxylic acid-(1S, 2S,5R)-[3-(3'-methoxy-biphenyl-2-carbonyl)-3-aza-bicyclo[3.3.0]oct-2-ylmethyl]-amide;
6-Methyl-imidazo[2,1-b]-thiazole-5-carboxylic acid-(1S, 2S,5R)-[3-(2-methyl-5-phenyl-thiazole-4-carbonyl)-3-aza-bicyclo[3.3.0]oct-2-ylmethyl]-amide;
6-Methyl-imidazo[2,1-b]thiazole-5-carboxylic acid-(1S, 2S,5R)-{3-[5-(4-fluoro-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-{3-[5-(4-ethyl-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-{3-[5-(4-chloro-phenyl)-2-methyl-thiazole-4-carbonyl]-3-aza-bicyclo[3.3.0]oct-2-ylmethyl}-amide;
6-Methyl-imidazo[2,1-b]thiazole-5-carboxylic acid-(1S, 2S,5R)-{3-[2-methyl-5-(4-trifluoromethyl-phenyl)-thiazole-4-carbonyl]-3-aza-bicyclo[3.3.0]oct-2-ylmethyl}-amide;

6-Methyl-imidazo[2,1-b]thiazole-5-carboxylic acid-(1S,2S,5R)-{3-[2-amino-5-(3-methyl-phenyl)-thiazole-4-carbonyl]-3-aza-bicyclo[3.3.0]oct-2-ylmethyl}-amide;

6-Methyl-imidazo[2,1-b]thiazole-5-carboxylic acid-(1S,2S,5R)-{3-[2-amino-5-(3-fluoro-phenyl)-thiazole-4-carbonyl]-3-aza-bicyclo[3.3.0]oct-2-ylmethyl}-amide;

6-Methyl-imidazo[2,1-b]thiazole-5-carboxylic acid-(1S,2S,5R)-[3-(2-amino-5-phenyl-thiazole-4-carbonyl)-3-aza-bicyclo[3.3.0]oct-2-ylmethyl]-amide;

6-Methyl-imidazo[2,1-b]thiazole-5-carboxylic acid-(1S,2S,5R)-{7-methyl-3-[2-amino-5-(3-methyl-phenyl)-thiazole-4-carbonyl]-3-aza-bicyclo[3.3.0]oct-2-ylmethyl}-amide;

6-Methyl-imidazo[2,1-b]thiazole-5-carboxylic acid-(1S,2S,5R)-{7-methyl-3-[2-amino-5-(4-fluoro-phenyl)-thiazole-4-carbonyl]-3-aza-bicyclo[3.3.0]oct-2-ylmethyl}-amide;

6-Methyl-imidazo[2,1-b]thiazole-5-carboxylic acid-(1S,2S,5R)-{7-methyl-3-[2-amino-5-(3-fluoro-phenyl)-thiazole-4-carbonyl]-3-aza-bicyclo[3.3.0]oct-2-ylmethyl}-amide; and Imidazo[2,1-b]thiazole-6-carboxylic acid-(1S,2S,5R)-[3-(2-methyl-5-m-tolyl-thiazole-4-carbonyl)-3-aza-bicyclo[3.3.0]oct-2-ylmethyl]-amide;

or a salt of such a compound.

15. The compound according to claim 1 selected from the group consisting of:

2-Methyl-benzofuran-4-carboxylic acid-(1S,2S,5R)-[7,7-difluoro-3-(2-methyl-5-m-tolyl-thiazole-4-carbonyl)-3-aza-bicyclo[3.3.0]oct-3-ylmethyl]-amide;

3-Methyl-benzofuran-4-carboxylic acid-(1S,2S,5R)-[7,7-difluoro-3-(2-methyl-5-m-tolyl-thiazole-4-carbonyl)-3-aza-bicyclo[3.3.0]oct-3-ylmethyl]-amide;

2,3-Dihydro-benzofuran-4-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide;

2,3-Dihydro-benzo[1,4]dioxine-5-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide;

Benzothiazole-7-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide;

6-Methyl-pyrrolo[2,1-b]thiazole-7-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide;

Imidazo[1,2-a]pyridine-3-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide;

1-Methyl-indazole-3-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide; and 6-Methyl-imidazo[2,1-b]-thiazole-5-carboxylic acid-(1S,2S,5R)-[7,7-difluoro-3-(2-methyl-5-m-tolyl-thiazole-4-carbonyl)-3-aza-bicyclo[3.3.0]oct-2-ylmethyl]-amide;

or a salt of such a compound.

\* \* \* \* \*